(12) United States Patent
Miyazaki

(10) Patent No.: US 8,247,612 B2
(45) Date of Patent: *Aug. 21, 2012

(54) ORGANIC SULFUR COMPOUND AND ITS USE FOR CONTROLLING HARMFUL ARTHROPOD

(75) Inventor: Hiroyuki Miyazaki, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 268 days.

This patent is subject to a terminal disclaimer.

(21) Appl. No.: 12/600,629

(22) PCT Filed: May 16, 2008

(86) PCT No.: PCT/JP2008/059491
§ 371 (c)(1),
(2), (4) Date: Nov. 17, 2009

(87) PCT Pub. No.: WO2008/143332
PCT Pub. Date: Nov. 27, 2008

(65) Prior Publication Data
US 2010/0160430 A1   Jun. 24, 2010

(30) Foreign Application Priority Data
May 18, 2007   (JP) .................. 2007-132612

(51) Int. Cl.
*C07C 317/04* (2006.01)
*C07C 317/44* (2006.01)
*C07C 317/28* (2006.01)
*C07C 233/04* (2006.01)
*C07C 255/04* (2006.01)

(52) U.S. Cl. ............ 568/31; 568/35; 564/209; 558/303

(58) Field of Classification Search ............ 568/31, 568/35; 564/209; 558/303
See application file for complete search history.

(56) References Cited

U.S. PATENT DOCUMENTS

| | | |
|---|---|---|
| 3,513,172 A | 5/1970 | Brokke et al. |
| 3,654,293 A | 4/1972 | Brokke |
| 3,666,818 A | 5/1972 | Brokke |
| 3,692,912 A | 9/1972 | Brokke |
| 3,697,536 A | 10/1972 | Brokke |
| 3,700,646 A | 10/1972 | Anello et al. |
| 3,780,050 A | 12/1973 | Brokke et al. |
| 3,891,662 A | 6/1975 | Brokke |
| 5,807,899 A | 9/1998 | Bohlmann et al. |
| 6,288,051 B1 | 9/2001 | Bittler et al. |
| 8,017,656 B2 * | 9/2011 | Miyazaki .............. 514/628 |
| 2003/0229050 A1 | 12/2003 | Lahm et al. |
| 2010/0152289 A1 * | 6/2010 | Miyazaki .............. 514/513 |
| 2010/0160434 A1 | 6/2010 | Miyazaki |

FOREIGN PATENT DOCUMENTS

| | | |
|---|---|---|
| EP | 0134200 A1 | 3/1985 |
| FR | 2516920 A1 | 5/1983 |
| FR | 2619811 A1 | 3/1989 |
| JP | 2004-91785 A | 3/2004 |
| JP | 2004-130306 A | 4/2004 |
| JP | 2005-179321 A | 7/2005 |
| WO | WO 98/07740 A1 | 2/1998 |
| WO | WO 98/25916 A1 | 6/1998 |
| WO | WO 99/33855 A1 | 7/1999 |
| WO | WO 99/42109 A1 | 8/1999 |
| WO | WO 00/03979 A1 | 1/2000 |
| WO | WO 02/40431 A2 | 5/2002 |
| WO | WO-2007/060839 A1 | 5/2007 |

OTHER PUBLICATIONS

Bellstein Registry Nos. 6215504, 6236294, 4325236, 6203175, 6212969, 8220992, 2009.

Benefice et al., "Reactivate Comparee des Perfluoroiodoalcanes (RFI) et des Perfluoroalcoyl-2 I0D0-1 Ethanes (RFCH2CH2I) en Presence de Couple Metal-Lique Zinc-Cuivre Dans un Solvant Dissociant Particulier: Le Sulfolane (RF=CnF2n+1=n pair)," Journal of Fluorine Chemistry, vol. 23, 1983, pp. 47-55.

Brace et al., "Oxidation chemistry of perfluoroalkyl-segmented thiols, disulfides, thiosulfinates and thiosulfonates. The role of the perfluoroalkyl group in searching out new chemistry," Journal of Fluorine Chemistry, vol. 105, 2000, pp. 11-23.

Calas et al., "Synthesis of terminally perfluorinated long-chain alkanethiols, sulfides and disulfides from the corresponding halides," Journal of Fluorine Chemistry, vol. 104, 2000, pp. 173-183.

Dieng et al., "Synthese et Application de Nouveaux Sulfures a Chaine perfluoree," Journal of Fluorine Chemistry, vol. 28, 1985, pp. 341-355.

Dieng et al., "Syntheses et Reactivate Des F-Alkyl Sulfures et Sulfones Actives," Journal of Fluorine Chemistry, vol. 28, 1985, pp. 425-440.

Faurote et al., "Some New Polyfluoroalkyl Halides, H(CF2)BCH2X, and the Reactions of H(CF2)BCH2I with Water, Sulfur and Selenium," New Polyfluoroalkyl Halides, 1956, pp. 4999-5001.

(Continued)

Primary Examiner — Jason M Nolan
(74) Attorney, Agent, or Firm — Birch, Stewart, Kolasch & Birch, LLP

(57) ABSTRACT

There is provided an organic sulfur compound having an excellent controlling effect on harmful arthropods represented by the formula (I): wherein, $R^1$ represents a C1-C5 haloalkyl group having at least one fluorine atom, $R^2$ represents a C1-C4 alkyl group optionally substituted with at least one halogen atom or the like, $R^3$ represents a hydrogen atom or the like, $R^4$ represents a cyano group or the like, $R^5$ represents a hydrogen atom or the like, m represents an integer of 1 to 4, and n represents 0, 1 or 2.

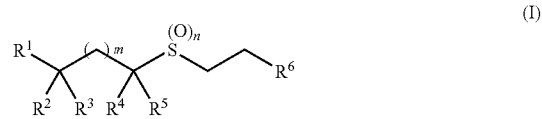

(I)

10 Claims, No Drawings

OTHER PUBLICATIONS

Fokin et al., "Some Properties of Fluorine-containing a,B-Unsaturated Sulfones," English Translation from Zhurnal Organicheskoi Khimii, vol. 22, No. 2, 1986, pp. 270-276.
Ilin et al., "Comparison of CF3-Substituted Ethylenic Compounds in Reactions with Chlorines of Sulfur," Zhurnal Vses. Khim. Ob-va im. D.I. Mendeleeva, vol. 28, No. 2, 1983, pp. 115-116, including 4-page English translation.
Mir et al., "Reactions of Hexafluoroacetone with Sulfur-Containing Compounds," Inorg. Chem., vol. 19, 1980, pp. 1510-1514.
Office Action in Australian Patent Application No. 2006317486 mailed Dec. 14, 2010.
Office Action in European Application No. 06832438.3 mailed Apr. 16, 2009.
Office Action in U.S. Appl. No. 12/094,255 mailed Dec. 8, 2010.
Office Action in U.S. Appl. No. 12/600,622 mailed Oct. 1, 2010.
Patani et al., "Bioisosterism: A Rational Approach in Drug Design," Chem. Rev., vol. 96, 1996, pp. 3147-3176.
Rocaboy et al., "Syntheses, oxidations, and palladium complexes of fluorous dialkyl sulfides: new precursors to highly active catalysts for the Suzuki coupling," Tetrahedron, vol. 58, 2002, pp. 4007-4014.
Sakamoto, "Fluoro Type Surfactants," XP-002415663, 2003.
Serdyuk et al., "Polyfluoroalkylthiotrifluoroacetylketenes," Russian Chemical Bulletin, International Edition, vol. 52, No. 8, 2003, pp. 1854-1858.
Serratrice et al., "Etude RMN Du13 C De Composes Fluoroaliphatiques et de Tensio-Actifs Non Ioniques Perfluoroalkyles," Journal of Fluorine Chemistry, vol. 25, 1984, pp. 275-288.
Shkurak et al., "Activated Addition of Sulfur Chlorides and Sulfenyl Chlorides to Hexafluorodimethylketene," pp. 1261-1268 and pp. 1371-1377, 1984.
Sodoyer et al., "Synthese de Nouvelles Sulfones F-Alkylees Saturees et a,B- Insaturees," Journal of Fluorine Chemistry, vol. 22, 1983, pp. 401-419.
Szonyi et al., "Fonctionnalisation Des Iodures de F-Alkyl -2 Ethane par Catalyze Par Transfert de Phase: Importance de Cette Technique en Serie F-Alkylee," Journal of Fluorine Chemistry, vol. 42, 1989, pp. 59-68, 1988.
Database WPI Week 200560; Thomson Scientific, London, GB; AN; 2005-585455; XP002493506.
International Preliminary Report on Patentability and Written Opinion dated Nov. 24, 2009 for Application No. PCT/JP2008/059491.
International Preliminary Report on Patentability and Written Opinion dated Nov. 24, 2009 for Application No. PCT/JP2008/059492.
International Preliminary Report on Patentability and Written Opinion dated Nov. 24, 2009 for Application No. PCT/JP2008/059498.
International Search Report dated Sep. 4, 2008 for Application No. PCT/JP2008/059491.
International Search Report dated Sep. 4, 2008 for Application No. PCT/JP2008/059492.
International Search Report dated Sep. 4, 2008 for Application No. PCT/JP2008/059498.

* cited by examiner

ORGANIC SULFUR COMPOUND AND ITS USE FOR CONTROLLING HARMFUL ARTHROPOD

TECHNICAL FIELD

The present invention relates to an organic sulfur compound and a use thereof for controlling harmful arthropods.

BACKGROUND ART

Hitherto, many pesticidal compositions for controlling harmful arthropods have been developed and used practically. Further, JP-A 2004-130306 discloses a certain fluorine-containing organic sulfur compound.

DISCLOSURE OF INVENTION

An object of the present invention is to provide a novel compound having an excellent controlling effect on harmful arthropods and its use.

The present inventors have intensively studied to find out a compound having an excellent controlling effect on harmful arthropods. As a result, they have found that an organic sulfur compound represented by the following formula (I) has an excellent controlling effect on harmful arthropods such as harmful insects and harmful mites. Thus, the present invention has been completed.

That is, the present invention provides:

(1) An organic sulfur compound represented by the formula (I):

$$R^1\underset{R^2\ R^3\ R^4\ R^5}{\overset{}{-}}(\ )_m\overset{(O)_n}{\underset{}{S}}-R^6 \quad (I)$$

wherein,
$R^1$ represents a C1-C5 haloalkyl group having at least one fluorine atom,
$R^2$ represents a C1-C4 alkyl group optionally substituted with at least one halogen atom, a C1-C4 alkoxy group optionally substituted with at least one halogen atom, or a C1-C4 alkylthio group optionally substituted with at least one halogen atom,
$R^3$ represents a hydrogen atom, a halogen atom or a C1-C4 alkyl group,
$R^4$ represents a cyano group, $C(=Q)OR^7$ or $C(=Q)N(R^8)_2$,
$R^5$ represents a hydrogen atom, a halogen atom or a C1-C4 alkyl group,
$R^6$ represents a C1-C5 fluoroalkyl group,
Q represents an oxygen atom or a sulfur atom,
$R^7$ represents a C1-C4 alkyl group,
$R^8$'s each independently represent a hydrogen atom or a C1-C4 alkyl group, or two $R^8$'s are bonded to each other at their terminals to form a C2-C7 alkylene group,
m represents an integer of 1 to 4, and
n represents 0, 1 or 2 (hereinafter, sometimes, referred to as the compound of the present invention);

(2) The organic sulfur compound according to the above (1), wherein n is 2;

(3) The organic sulfur compound according to the above (1) or (2), wherein Q is an oxygen atom;

(4) The organic sulfur compound according to the above (1) or (2), wherein $R^4$ is a cyano group;

(5) The organic sulfur compound according to the above (1) or (2), wherein $R^4$ is $C(=Q)N(R^8)_2$, and $R^8$'s are each independently a hydrogen atom or a C1-C4 alkyl group;

(6) The organic sulfur compound according to the above (1) or (2), wherein $R^4$ is $C(=Q)N(R^8)_2$ and $R^8$ is a hydrogen atom;

(7) The organic sulfur compound according to any one of the above (1) to (6), wherein $R^5$ is a halogen atom;

(8) The organic sulfur compound according to any one of the above (1) to (7), wherein m is 2;

(9) A pesticidal composition comprising the organic sulfur compound according to any one of the above (1) to (8) as an active ingredient;

(10) A method for controlling harmful arthropods comprising applying an effective amount of the organic sulfur compound according to any one of the above (1) to (8) to harmful arthropods or a place where harmful arthropods inhabit;

(11) A use of the organic sulfur compound according to any one of the above (1) to (8) for production of a pesticidal composition; and the like.

BEST MODE FOR CARRYING OUT THE INVENTION

In the present invention, the expression "C1-C4" or the like means the total number of carbon atoms constituting a substituent group.

Examples of the "C1-C5 haloalkyl group having at least one fluorine atom" represented by $R^1$ in the formula (I) include a C1-C2 haloalkyl group such as a fluoromethyl group, a difluoromethyl group, a trifluoromethyl group, a bromodifluoromethyl group, a chlorodifluoromethyl group, a 1-fluoroethyl group, a 1,1-difluoroethyl group, a 2-fluoroethyl group, a 2,2-difluoroethyl group, a 2,2,2-trifluoroethyl group, a 1,1,2,2-tetrafluoroethyl group and a 1,1,2,2,2-pentafluoroethyl group; a C3 haloalkyl group such as a 1-fluoropropyl group, a 1,1-difluoropropyl group, a 2-fluoropropyl group, a 2,2-difluoropropyl group, a 3-fluoropropyl group, a 3,3-difluoropropyl group, a 3,3,3-trifluoropropyl group, a 2,2,3,3,3-pentafluoropropyl group and a 1,1,2,2,3,3,3-heptafluoropropyl group; a C4 haloalkyl group such as a 1-fluorobutyl group, a 1,1-difluorobutyl group, a 2-fluorobutyl group, a 2,2-difluorobutyl group, a 3-fluorobutyl group, a 3,3-difluorobutyl group, a 4-fluorobutyl group, a 4,4-difluorobutyl group, a 4,4,4-trifluorobutyl group, a 3,3,4,4,4-pentafluorobutyl group, a 2,2,3,3,4,4,4-heptafluorobutyl group and a 1,1,2,2,3,3,4,4,4-nonafluorobutyl group; and a C5 haloalkyl group such as a 1-fluoropentyl group, a 1,1-difluoropentyl group, a 2-fluoropentyl group, a 2,2-difluoropentyl group, a 3-fluoropentyl group, a 3,3-difluoropentyl group, a 4-fluoropentyl group, a 4,4-difluoropentyl group, a 5-fluoropentyl group, a 5,5-difluoropentyl group, a 5,5,5-trifluoropentyl group, a 4,4,5,5,5-pentafluoropentyl group, a 3,3,4,4,5,5,5-heptafluoropentyl group, a 2,2,3,3,4,4,5,5,5-nonafluoropentyl group and a 1,1,2,2,3,3,4,4,5,5,5-undecafluoropentyl group.

Examples of the "C1-C5 fluoroalkyl group" represented by $R^6$ in the formula (I) include a C1-C2 fluoroalkyl group such as a fluoromethyl group, a difluoromethyl group, a trifluoromethyl group, a 1-fluoroethyl group, a 2-fluoroethyl group, a 1,1-difluoroethyl group, a 2,2-difluoroethyl group, a 2,2,2-trifluoroethyl group and a 1,1,2,2,2-pentafluoroethyl group; a C3 fluoroalkyl group such as a 1-fluoropropyl group, a 1,1-difluoropropyl group, a 2-fluoropropyl group, a 2,2-difluoropropyl group, a 3-fluoropropyl group, a 3,3-difluoropropyl group, a 3,3,3-trifluoropropyl group, a 1,1,2,2,3,3,3-heptafluoropropyl group, a 2,2,3,3,3-pentafluoropropyl group, a 2,2,2-trifluoro-(1-trifluoromethyl)ethyl group, a 1,2,2,2-tetrafluoro-(1-trifluoromethyl)ethyl group and a 2,2,3,3-tetrafluoropropyl group; a C4 fluoroalkyl group such as a 1-fluorobutyl group, a 1,1-difluorobutyl group, a 2-fluorobutyl group, a 2,2-difluorobutyl group, a 3-fluorobutyl group, a 3,3-difluorobutyl group, a 4-fluorobutyl group, a 4,4-difluorobutyl group, a 4,4,4-trifluorobutyl group, a 3,3,4,4,4-pentafluorobutyl group, a 2,2,3,4,4-pentafluorobutyl group and a 2,2,3,3,4,4,4-heptafluorobutyl group; a C5 fluoroalkyl group such as a 1-fluoropentyl group, a 1,1-difluoropentyl group, a 2-fluoropentyl group, a 2,2-difluoropentyl group, a 3-fluoropentyl group, a 3,3-difluoropentyl group, a 4-fluoropentyl group, a 4,4-difluoropentyl group, a 5-fluoropentyl group, a 5,5-difluoropentyl group, a 5,5,5-trifluoropentyl group, a 4,4,5,5,5-pentafluoropentyl group, a 3,3,4,4,5,5,5-heptafluoropentyl group, a 2,2,3,3,4,4,5,5-octafluoropentyl group and a 2,2,3,3,4,4,5,5,5-nonafluoropentyl group.

In the present invention, a preferred example of the "C1-C5 fluoroalkyl group" includes a group represented by the following formula:

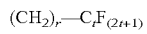

$(CH_2)_r-C_tF_{(2t+1)}$ wherein r represents an integer of 0 to 4 and t represents an integer of 1 to 3, provided that r+t is 5 or less.

Examples of the "C1-C4 alkyl group optionally substituted with at least one halogen atom" represented by $R^2$ in the formula (I) include a methyl group, an ethyl group, a propyl group, an isopropyl group, a butyl group, an isobutyl group, a tert-butyl group, a fluoromethyl group, a chloromethyl group, a bromomethyl group, a difluoromethyl group, a trifluoromethyl group and a trichloromethyl group.

Examples of the "C1-C4 alkoxy group optionally substituted with at least one halogen atom" represented by $R^2$ in the formula (I) include a methoxy group, an ethoxy group, a propoxy group, an isopropoxy group, a butoxy group, an isobutoxy group, a tert-butoxy group and a trifluoromethoxy group.

Examples of the "C1-C4 alkylthio group optionally substituted with at least one halogen atom" represented by $R^2$ in the formula (I) include a methylthio group, an ethylthio group, a propylthio group, an isopropylthio group, a butylthio group, an isobuthylthio group, a tert-buthylthio group and a trifluoromethylthio group.

Examples of the "C1-C4 alkyl group" represented by $R^3$ in the formula (I) include a methyl group, an ethyl group, a propyl group, an isopropyl group, a butyl group, an isobutyl group and a tert-butyl group.

Examples of the "C1-C4 alkyl group" represented by $R^5$ in the formula (I) include a methyl group, an ethyl group, a propyl group, an isopropyl group, a butyl group, an isobutyl group and a tert-butyl group.

Examples of the "C1-C4 alkyl group" represented by $R^7$ in the formula (I) include a methyl group, an ethyl group, a propyl group, an isopropyl group, a butyl group, an isobutyl group and a tert-butyl group.

Examples of the "C1-C4 alkyl group" represented by $R^8$ in the formula (I) include a methyl group, an ethyl group, a propyl group, an isopropyl group, a butyl group, an isobutyl group and a tert-butyl group.

Examples of the "C2-C7 alkylene group" formed by bonding of two $R^8$'s at their terminals include an ethylene group, a trimethylene group, a tetramethylene group and a hexamethylene group.

Examples of a group represented by $N(R^6)_2$ include acyclic amino groups such as amino group, a methylamino group, an ethylamino group, a propylamino group, a 2-propylamino group, a butylamino group, an isobutylamino group, a tert-butylamino group and a dimethylamino group; and cyclic amino groups such as 1-aziridino group, a 1-azetidinyl group, a 1-pyrrolidinyl group and a piperidino group.

Specific examples of the compound of the present invention include:

an organic sulfur compound represented by the formula (I) wherein n is 2;

an organic sulfur compound represented by the formula (I) wherein Q is an oxygen atom;

an organic sulfur compound represented by the formula (I) wherein $R^4$ is a cyano group;

an organic sulfur compound represented by the formula (I) wherein $R^4$ is $C(=Q)OR^7$ or $C(=Q)N(R^8)_2$;

an organic sulfur compound represented by the formula (I) wherein $R^4$ is $C(=Q)N(R^8)_2$ and $R^8$'s are each independently a hydrogen atom or a C1-C4 alkyl group;

an organic sulfur compound represented by the formula (I) wherein $R^4$ is $C(=Q)N(R^8)_2$ and $R^8$ is a hydrogen atom;

an organic sulfur compound represented by the formula (I) wherein m is 2;

an organic sulfur compound represented by the formula (I) wherein $R^1$ is a trifluoromethyl group, a 1,1,2,2,2-pentafluoroethyl group or a 1,1,2,2,3,3,3-heptafluoropropyl group;

an organic sulfur compound represented by the formula (I) wherein $R^1$ is a trifluoromethyl group;

an organic sulfur compound represented by the formula (I) wherein $R^1$ is a 1,1,2,2,2-pentafluoroethyl group;

an organic sulfur compound represented by the formula (I) wherein $R^1$ is a 1,1,2,2,3,3,3-heptafluoropropyl group;

an organic sulfur compound represented by the formula (I) wherein $R^2$ is a methyl group, an ethyl group, a propyl group, an isopropyl group, a tert-butyl group, a methoxy group or a methylthio group;

an organic sulfur compound represented by the formula (I) wherein $R^2$ is a methyl group, an ethyl group, a methoxy group or a methylthio group;

an organic sulfur compound represented by the formula (I) wherein $R^2$ is a methyl group;

an organic sulfur compound represented by the formula (I) wherein $R^2$ is an ethyl group;

an organic sulfur compound represented by the formula (I) wherein $R^2$ is a propyl group;

an organic sulfur compound represented by the formula (I) wherein $R^2$ is an isopropyl group;

an organic sulfur compound represented by the formula (I) wherein $R^2$ is a tert-butyl group;

an organic sulfur compound represented by the formula (I) wherein $R^2$ is a methoxy group;

an organic sulfur compound represented by the formula (I) wherein $R^2$ is a methylthio group;

an organic sulfur compound represented by the formula (I) wherein $R^3$ is a hydrogen atom or a methyl group;

an organic sulfur compound represented by the formula (I) wherein $R^3$ is a hydrogen atom;

an organic sulfur compound represented by the formula (I) wherein $R^3$ is a methyl group;

an organic sulfur compound represented by the formula (I) wherein $R^5$ is a hydrogen atom;

an organic sulfur compound represented by the formula (I) wherein $R^5$ is a halogen atom;

an organic sulfur compound represented by the formula (I) wherein $R^5$ is a fluorine atom or a chlorine atom;

an organic sulfur compound represented by the formula (I) wherein $R^5$ is a methyl group;

an organic sulfur compound represented by the formula (I) wherein $R^6$ is a group represented by the formula:

$$(CH_2)_r\text{—}C_tF_{(2t+1)}$$

wherein r represents an integer of 0 to 4 and t represents an integer of 1 to 3, provided that r+t is 5 or less;

an organic sulfur compound represented by the formula (I) wherein $R^6$ is a C1-C3 fluoroalkyl group;

an organic sulfur compound represented by the formula (I) wherein $R^6$ is a trifluoromethyl group, a 1,1,2,2,2-pentafluoroethyl group, a 2,2,2-trifluoroethyl group or a 1,1,2,2,3,3,3-heptafluoropropyl group;

an organic sulfur compound represented by the formula (I) wherein $R^6$ is a trifluoromethyl group;

an organic sulfur compound represented by the formula (I) wherein $R^6$ is a 1,1,2,2,2-pentafluoroethyl group;

an organic sulfur compound represented by the formula (I) wherein $R^6$ is a 2,2,2-trifluoroethyl group;

an organic sulfur compound represented by the formula (I) wherein $R^6$ is a 1,1,2,2,3,3,3-heptafluoropropyl group;

an organic sulfur compound represented by the formula (I) wherein $R^2$ is a methyl group, an ethyl group, a propyl group, an isopropyl group, a tert-butyl group, a methoxy group or a methylthio group, and $R^3$ is a hydrogen atom or a methyl group;

an organic sulfur compound represented by the formula (I) wherein $R^2$ is a methyl group, an ethyl group, a methoxy group or a methylthio group, and $R^3$ is a hydrogen atom or a methyl group;

an organic sulfur compound represented by the formula (I) wherein $R^2$ is a methyl group, an ethyl group, a propyl group, an isopropyl group, a tert-butyl group, a methoxy group or a methylthio group, and $R^3$ is a hydrogen atom;

an organic sulfur compound represented by the formula (I) wherein $R^2$ is a methyl group, an ethyl group, a methoxy group or a methylthio group, and $R^3$ is a hydrogen atom;

an organic sulfur compound represented by the formula (I) wherein $R^2$ is a methyl group, an ethyl group, a propyl group, an isopropyl group or a tert-butyl group, and $R^3$ is a hydrogen atom;

an organic sulfur compound represented by the formula (I) wherein $R^2$ is a methyl group or an ethyl group, and $R^3$ is a hydrogen atom;

an organic sulfur compound represented by the formula (I) wherein $R^2$ is a methoxy group or a methylthio group, and $R^3$ is a hydrogen atom;

an organic sulfur compound represented by the formula (I) wherein Q is an oxygen atom and $R^5$ is a hydrogen atom;

an organic sulfur compound represented by the formula (I) wherein Q is an oxygen atom and $R^5$ is a halogen atom;

an organic sulfur compound represented by the formula (I) wherein Q is an oxygen atom and $R^5$ is a fluorine atom or a chlorine atom;

an organic sulfur compound represented by the formula (I) wherein Q is an oxygen atom and $R^5$ is a methyl group;

an organic sulfur compound represented by the formula (I) wherein $R^4$ is a cyano group and $R^5$ is a hydrogen atom;

an organic sulfur compound represented by the formula (I) wherein $R^4$ is a cyano group and $R^5$ is a halogen atom;

an organic sulfur compound represented by the formula (I) wherein $R^4$ is a cyano group and $R^5$ is a fluorine atom or a chlorine atom;

an organic sulfur compound represented by the formula (I) wherein $R^4$ is a cyano group and $R^5$ is a methyl group;

an organic sulfur compound represented by the formula (I) wherein $R^4$ is C(=Q)N($R^8$)$_2$ and $R^5$ is a hydrogen atom;

an organic sulfur compound represented by the formula (I) wherein $R^4$ is C(=Q)N($R^8$)$_2$ and $R^5$ is a halogen atom;

an organic sulfur compound represented by the formula (I) wherein $R^4$ is C(=Q)N($R^8$)$_2$ and $R^5$ is a fluorine atom or a chlorine atom;

an organic sulfur compound represented by the formula (I) wherein $R^4$ is C(=Q)N($R^8$)$_2$ and $R^5$ is a methyl group;

an organic sulfur compound represented by the formula (I) wherein $R^4$ is C(=Q)N($R^8$)$_2$, $R^5$ is a hydrogen atom and $R^8$ is a hydrogen atom;

an organic sulfur compound represented by the formula (I) wherein $R^4$ is C(=Q)N($R^8$)$_2$, $R^5$ is a halogen atom and $R^8$ is a hydrogen atom;

an organic sulfur compound represented by the formula (I) wherein $R^4$ is C(=Q)N($R^8$)$_2$, $R^5$ is a fluorine atom or a chlorine atom, and $R^8$ is a hydrogen atom;

an organic sulfur compound represented by the formula (I) wherein $R^4$ is C(=Q)N($R^8$)$_2$, $R^5$ is a methyl group and $R^8$ is a hydrogen atom;

an organic sulfur compound represented by the formula (I) wherein n is 2, $R^4$ is a cyano group and $R^5$ is a hydrogen atom;

an organic sulfur compound represented by the formula (I) wherein n is 2, $R^4$ is a cyano group and $R^5$ is a halogen atom;

an organic sulfur compound represented by the formula (I) wherein n is 2, $R^4$ is a cyano group and $R^5$ is a fluorine atom or a chlorine atom;

an organic sulfur compound represented by the formula (I) wherein n is 2, $R^4$ is a cyano group and $R^5$ is a methyl group;

an organic sulfur compound represented by the formula (I) wherein n is 2, $R^4$ is C(=Q)N($R^8$)$_2$, $R^5$ is a hydrogen atom and $R^8$ is a hydrogen atom;

an organic sulfur compound represented by the formula (I) wherein n is 2, $R^4$ is C(=Q)N($R^8$)$_2$, $R^5$ is a halogen atom and $R^8$ is a hydrogen atom;

an organic sulfur compound represented by the formula (I) wherein n is 2, $R^4$ is C(=Q)N($R^8$)$_2$, $R^5$ is a fluorine atom or a chlorine atom, and $R^8$ is a hydrogen atom;

an organic sulfur compound represented by the formula (I) wherein n is 2, $R^4$ is C(=Q)N($R^8$)$_2$, $R^5$ is a methyl group and $R^8$ is a hydrogen atom;

an organic sulfur compound represented by the formula (I) wherein n is 2, m is 2, $R^4$ is a cyano group and $R^5$ is a hydrogen atom;

an organic sulfur compound represented by the formula (I) wherein n is 2, m is 2, $R^4$ is a cyano group and $R^5$ is a halogen atom;

an organic sulfur compound represented by the formula (I) wherein n is 2, m is 2, $R^4$ is a cyano group and $R^5$ is a fluorine atom or a chlorine atom;

an organic sulfur compound represented by the formula (I) wherein n is 2, m is 2, $R^4$ is a cyano group and $R^5$ is a methyl group;

an organic sulfur compound represented by the formula (I) wherein n is 2, m is 2, $R^4$ is C(=O)NH$_2$ and $R^5$ is a hydrogen atom;

an organic sulfur compound represented by the formula (I) wherein n is 2, m is 2, $R^4$ is C(=O)NH$_2$ and $R^5$ is a halogen atom;

an organic sulfur compound represented by the formula (I) wherein n is 2, m is 2, $R^4$ is C(=O)NH$_2$ and $R^5$ is a fluorine atom or a chlorine atom;

an organic sulfur compound represented by the formula (I) wherein n is 2, m is 2, $R^4$ is C(=O)NH$_2$ and $R^5$ is a methyl group;

an organic sulfur compound represented by the formula (I) wherein n is 2, m is 2, $R^1$ is a trifluoromethyl group, $R^4$ is a cyano group and $R^5$ is a hydrogen atom;

an organic sulfur compound represented by the formula (I) wherein n is 2, m is 2, $R^1$ is a trifluoromethyl group, $R^4$ is a cyano group and $R^5$ is a halogen atom;

an organic sulfur compound represented by the formula (I) wherein n is 2, m is 2, $R^1$ is a trifluoromethyl group, $R^4$ is a cyano group and $R^5$ is a fluorine atom or a chlorine atom;

an organic sulfur compound represented by the formula (I) wherein n is 2, m is 2, $R^1$ is a trifluoromethyl group, $R^4$ is a cyano group and $R^5$ is a methyl group;

an organic sulfur compound represented by the formula (I) wherein n is 2, m is 2, $R^1$ is a trifluoromethyl group, $R^4$ is $C(=O)NH_2$ and $R^5$ is a hydrogen atom;

an organic sulfur compound represented by the formula (I) wherein n is 2, m is 2, $R^1$ is a trifluoromethyl group, $R^4$ is $C(=O)NH_2$ and $R^5$ is a halogen atom;

an organic sulfur compound represented by the formula (I) wherein n is 2, m is 2, $R^1$ is a trifluoromethyl group, $R^4$ is $C(=O)NH_2$ and $R^5$ is a fluorine atom or a chlorine atom;

an organic sulfur compound represented by the formula (I) wherein n is 2, m is 2, $R^1$ is a trifluoromethyl group, $R^4$ is $C(=O)NH_2$ and $R^5$ is a methyl group;

an organic sulfur compound represented by the formula (I) wherein n is 2, m is 2, $R^1$ is a 1,1,2,2,2-pentafluoroethyl group, $R^4$ is a cyano group and $R^5$ is a hydrogen atom;

an organic sulfur compound represented by the formula (I) wherein n is 2, m is 2, $R^1$ is a 1,1,2,2,2-pentafluoroethyl group, $R^4$ is a cyano group and $R^5$ is a halogen atom;

an organic sulfur compound represented by the formula (I) wherein n is 2, m is 2, $R^1$ is a 1,1,2,2,2-pentafluoroethyl group, $R^4$ is a cyano group and $R^5$ is a fluorine atom or a chlorine atom;

an organic sulfur compound represented by the formula (I) wherein n is 2, m is 2, $R^1$ is a 1,1,2,2,2-pentafluoroethyl group, $R^4$ is a cyano group and $R^5$ is a methyl group;

an organic sulfur compound represented by the formula (I) wherein n is 2, m is 2, $R^1$ is a 1,1,2,2,2-pentafluoroethyl group, $R^4$ is $C(=O)NH_2$ and $R^5$ is a hydrogen atom;

an organic sulfur compound represented by the formula (I) wherein n is 2, m is 2, $R^1$ is a 1,1,2,2,2-pentafluoroethyl group, $R^4$ is $C(=O)NH_2$ and $R^5$ is a halogen atom;

an organic sulfur compound represented by the formula (I) wherein n is 2, m is 2, $R^1$ is a 1,1,2,2,2-pentafluoroethyl group, $R^4$ is $C(=O)NH_2$ and $R^5$ is a fluorine atom or a chlorine atom;

an organic sulfur compound represented by the formula (I) wherein n is 2, m is 2, $R^1$ is a 1,1,2,2,2-pentafluoroethyl group, $R^4$ is $C(=O)NH_2$ and $R^5$ is a methyl group;

an organic sulfur compound represented by the formula (I) wherein n is 2, m is 2, $R^1$ is a 1,1,2,2,3,3,3-heptafluoropropyl group, $R^4$ is a cyano group and $R^5$ is a hydrogen atom;

an organic sulfur compound represented by the formula (I) wherein n is 2, m is 2, $R^1$ is a 1,1,2,2,3,3,3-heptafluoropropyl group, $R^4$ is a cyano group and $R^5$ is a halogen atom;

an organic sulfur compound represented by the formula (I) wherein n is 2, m is 2, $R^1$ is a 1,1,2,2,3,3,3-heptafluoropropyl group, $R^4$ is a cyano group and $R^5$ is a fluorine atom or a chlorine atom;

an organic sulfur compound represented by the formula (I) wherein n is 2, m is 2, $R^1$ is a 1,1,2,2,3,3,3-heptafluoropropyl group, $R^4$ is a cyano group and $R^5$ is a methyl group;

an organic sulfur compound represented by the formula (I) wherein n is 2, m is 2, $R^1$ is a 1,1,2,2,3,3,3-heptafluoropropyl group, $R^4$ is $C(=O)NH_2$ and $R^5$ is a hydrogen atom;

an organic sulfur compound represented by the formula (I) wherein n is 2, m is 2, $R^1$ is a 1,1,2,2,3,3,3-heptafluoropropyl group, $R^4$ is $C(=O)NH_2$ and $R^5$ is a halogen atom;

an organic sulfur compound represented by the formula (I) wherein n is 2, m is 2, $R^1$ is a 1,1,2,2,3,3,3-heptafluoropropyl group, $R^4$ is $C(=O)NH_2$ and $R^5$ is a fluorine atom or a chlorine atom;

an organic sulfur compound represented by the formula (I) wherein n is 2, m is 2, $R^1$ is a 1,1,2,2,3,3,3-heptafluoropropyl group, $R^4$ is $C(=O)NH_2$ and $R^5$ is a methyl group;

an organic sulfur compound represented by the formula (I) wherein $R^1$ is a trifluoromethyl group, a 1,1,2,2,2-pentafluoroethyl group or a 1,1,2,2,3,3,3-heptafluoropropyl group, $R^2$ is a C1-C4 alkyl group optionally substituted with at least one halogen atom, $R^3$ is a hydrogen atom, a methyl group, an ethyl group, a fluorine atom or a chlorine atom, $R^4$ is a cyano group, $C(=O)OR^7$ or $C(=O)N(R^8)_2$, $R^5$ is a hydrogen atom, a methyl group, an ethyl group, a fluorine atom or a chlorine atom, $R^6$ is a trifluoromethyl group, a 1,1,2,2,2-pentafluoroethyl group or a 1,1,2,2,3,3,3-heptafluoropropyl group, m is 2, $R^7$ is a methyl group, and $R^8$'s are each independently a hydrogen atom or a methyl group;

an organic sulfur compound represented by the formula (I) wherein $R^1$ is a trifluoromethyl group, a 1,1,2,2,2-pentafluoroethyl group or a 1,1,2,2,3,3,3-heptafluoropropyl group, $R^2$ is a C1-C4 alkoxy group optionally substituted with at least one halogen atom or a C1-C4 alkylthio group optionally substituted with at least one halogen atom, $R^3$ is a hydrogen atom, a methyl group, an ethyl group, a fluorine atom or a chlorine atom, $R^4$ is a cyano group, $C(=O)OR^7$ or $C(=O)N(R^8)_2$, $R^5$ is a hydrogen atom, a methyl group, an ethyl group, a fluorine atom or a chlorine atom, $R^6$ is a trifluoromethyl group, a 1,1,2,2,2-pentafluoroethyl group or q 1,1,2,2,3,3,3-heptafluoropropyl group, m is 2, $R^7$ is a methyl group, and $R^8$'s are each independently a hydrogen atom or a methyl group;

an organic sulfur compound represented by the formula (I) wherein $R^1$ is a trifluoromethyl group, $R^2$ is a methyl group or an ethyl group, $R^3$ is a hydrogen atom, a methyl group, an ethyl group, a fluorine atom or a chlorine atom, $R^4$ is a cyano group, $C(=O)OR^7$ or $C(=O)N(R^8)_2$, $R^5$ is a hydrogen atom, a methyl group, an ethyl group, a fluorine atom or a chlorine atom, $R^6$ is a trifluoromethyl group, a 1,1,2,2,2-pentafluoroethyl group or a 1,1,2,2,3,3,3-heptafluoropropyl group, m is 2, $R^7$ is a methyl group, and $R^8$ is a hydrogen atom;

an organic sulfur compound represented by the formula (I) wherein $R^1$ is a trifluoromethyl group, $R^2$ is a methoxy group or a methylthio group, $R^3$ is a hydrogen atom, a methyl group, an ethyl group, a fluorine atom or a chlorine atom, $R^4$ is a cyano group, $C(=O)OR^7$ or $C(=O)N(R^8)_2$, $R^5$ is a hydrogen atom, a methyl group, an ethyl group, a fluorine atom or a chlorine atom, $R^6$ is a trifluoromethyl group, a 1,1,2,2,2-pentafluoroethyl group or a 1,1,2,2,3,3,3-heptafluoropropyl group, m is 2, $R^7$ is a methyl group, and $R^8$ is a hydrogen atom.

Next, a process for production of the compound of the present invention is explained.

The compound of the present invention can be produced by, for example, the following Production processes 1 to 12.

Production Process 1

Among the compounds of the present invention, a compound (I-2) that is a compound of the formula (I) wherein $R^5$ is a C1-C4 alkyl group can be produced, for example, by reacting a compound (a) with a compound (I-1) as follows:

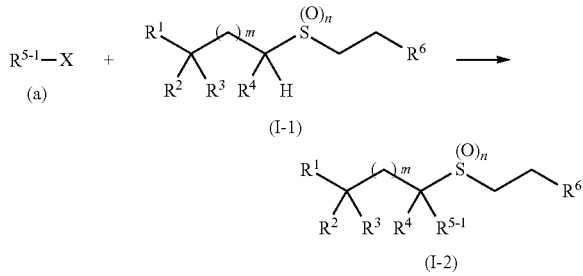

wherein $R^1$, $R^2$, $R^3$, $R^4$, $R^6$, m and n are as defined above, $R^{5-1}$ represents a C1-C4 alkyl group, X represents a leaving group such as a chlorine atom, a bromine atom, an iodine atom, a methanesulfonyloxy group, a p-toluenesulfonyloxy group or a trifluoromethanesulfonyloxy group.

The reaction is usually carried out in a solvent in the presence of a base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate, alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the base used in the reaction is usually 1 to 10 mol relative to 1 mol of the compound (I-1).

The amount of the compound (a) used in the reaction is usually 1 to 10 mol relative to 1 mol of the compound (I-1).

The reaction temperature is usually in a range of −100 to 100° C., and the reaction time is usually 1 to 24 hours.

After completion of the reaction, the compound (I-2) can be isolated by post-treatment, for example, by pouring a reaction mixture into water and extracting the resulting mixture with an organic solvent followed by concentration. The isolated compound (I-2) can be further purified by column chromatography, recrystallization or the like, if necessary.

Production Process 2

Among the compounds of the present invention, a compound (I-3) that is a compound of the formula (I) wherein $R^5$ is a hydrogen atom or a C1-C4 alkyl group can be produced, for example, by reacting a compound (c) with a compound (d) as follows:

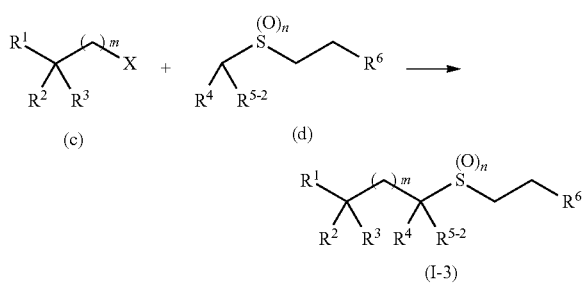

wherein $R^1$, $R^2$, $R^3$, $R^4$, $R^6$, m, n and X are as defined above, and $R^{5-2}$ represents a hydrogen atom or a C1-C4 alkyl group.

The reaction is usually carried out in a solvent in the presence of a base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate, alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the base used in the reaction is usually 1 to 10 mol relative to 1 mol of the compound (d).

The amount of the compound (c) used in the reaction is usually 1 to 10 mol relative to 1 mol of the compound (d).

The reaction temperature is usually in a range of −100 to 100° C., and the reaction time is usually 1 to 24 hours.

After completion of the reaction, the compound (I-3) can be isolated by post-treatment, for example, by pouring a reaction mixture into water and extracting the resulting mixture with an organic solvent followed by concentration. The isolated compound (I-3) can be further purified by column chromatography, recrystallization or the like, if necessary.

Among the compounds of the present invention, a compound (I-4) that is a compound of the formula (I) wherein $R^5$ is a halogen atom can be produced, for example, by the following Production process 3 or 4.

Production Process 3

This process comprises reacting a compound (I-1) with a halogenating agent (e) in the presence of a base as follows:

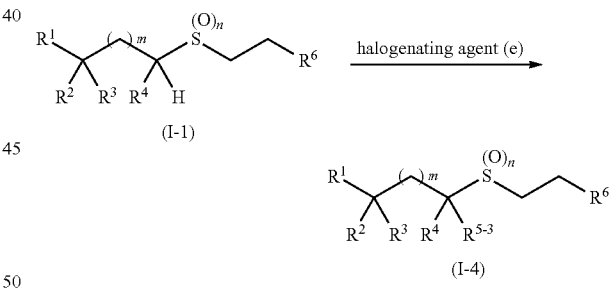

wherein $R^1$, $R^2$, $R^3$, $R^4$, $R^6$, m and n are as defined above, and $R^{5-3}$ represents a halogen atom.

The reaction is usually carried out in a solvent in the presence of a base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate, alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the base used in the reaction is usually 1 to 10 mol relative to 1 mol of the compound (I-1).

Examples of the halogenating agent (e) used in the reaction include halogenated hydrocarbons such as carbon tetrachloride and hexachloroethane, halogens such as fluorine, chlorine, bromine and iodine, halogenated succinimides such as N-chlorosuccinimide, N-bromosuccinimide and N-iodosuccinimide, N-fluoropyridinium salts such as 1-fluoro-2,4,6-trimethylpyridinium trifluoromethanesulfonate and 1,1'-difluoro-2,2'-bipyridinium bis-tetrafluoroborate, and inorganic salts such as copper (II) chloride and copper (II) bromide.

The amount of the halogenating agent (e) used in the reaction is usually 1 to 10 mol relative to 1 mol of the compound (I-1).

The reaction temperature is usually in a range of −100 to 100° C., and the reaction time is usually 1 to 24 hours.

After completion of the reaction, the compound (I-4) can be isolated by post-treatment, for example, by pouring a reaction mixture into water and extracting the resulting mixture with an organic solvent followed by concentration. The isolated compound (I-4) can be further purified by column chromatography, recrystallization or the like, if necessary.

Production Process 4

This process comprises reacting a compound (I-1) with a halogenating agent (f) as follows:

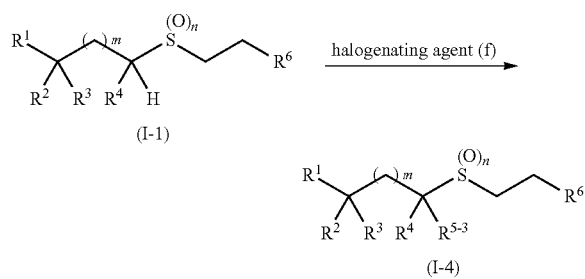

wherein $R^1$, $R^2$, $R^3$, $R^4$, $R^{5-3}$, $R^6$, m and n are as defined above.

The reaction is usually carried out without any solvent or in a solvent.

Examples of a solvent used in the reaction include halogenated hydrocarbons such as chloroform, carbon tetrachloride, 1,2-dichloroethane and chlorobenzene, aromatic hydrocarbons such as toluene and xylene, aliphatic nitriles such as acetonitrile and propionitrile, aliphatic carboxylic acids such as acetic acid, carbon disulfide, water and a mixture thereof.

Examples of the halogenating agent (f) used in the reaction include halogens such as fluorine, chlorine, bromine and iodine, hydrogen halides such as hydrogen fluoride, hydrogen chloride, hydrogen bromide and hydrogen iodide, halogenated sulfur compounds such as thionyl chloride, thionyl bromide and sulfuryl chloride, halogenated phosphorous compounds such as phosphorous trichloride, phosphorous tribromide, phosphorous pentachloride and phosphorous oxychloride.

The amount of halogenating agent (f) used in the reaction is usually 1 to 10 mol relative to 1 mol of the compound (I-1).

The reaction temperature is usually in a range of −100 to 200° C., and the reaction time is usually 1 to 24 hours.

After completion of the reaction, the compound (I-4) can be isolated by post-treatment, for example, by pouring a reaction mixture into water and extracting the resulting mixture with an organic solvent followed by concentration. The isolated compound (I-4) can be further purified by column chromatography, recrystallization or the like, if necessary.

Among the compounds of the present invention, a compound (I-5) that is a compound of the formula (I) wherein $R^4$ is $C(=O)OR^7$ or $C(=O)N(R^8)_2$ can be produced, for example, by the following Production process 5 or 6.

Production Process 5

This process comprises reacting a compound (i) with a compound (j) as follows:

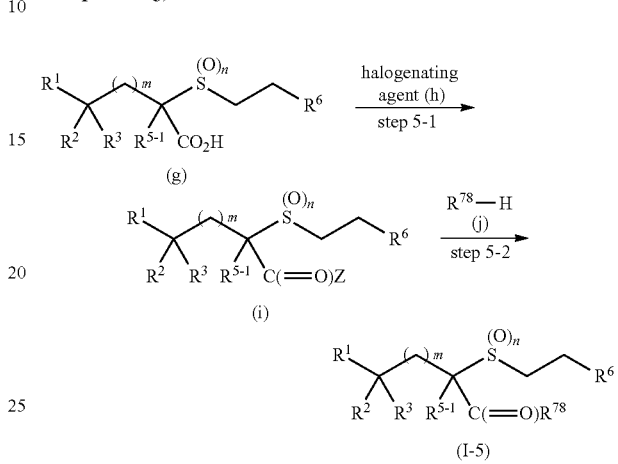

wherein $R^1$, $R^2$, $R^3$, $R^{5-1}$, $R^6$, m and n are as defined above, Z represents a halogen atom, and $R^{78}$ represents $OR^7$ or $N(R^8)_2$ in which $R^7$ and $R^8$ are as defined above.

Step 5-1:

The compound (i) can be produced by reacting the compound (g) with the halogenating agent (h).

The reaction can be carried out without solvent or in a solvent.

Examples of a solvent used in the reaction include halogenated hydrocarbons such as chloroform, dichloromethane, 1,2-dichloroethane and chlorobenzene, and aromatic hydrocarbons such as toluene and xylene.

Examples of the halogenating agent (h) used in the reaction include oxalyl chloride, thionyl chloride, thionyl bromide, phosphorous trichloride, phosphorous tribromide and phosphorous pentachloride.

The amount of the halogenating agent (h) used in the reaction is usually from 1 mol to a sufficient amount as a solvent relative to 1 mol of the compound (g).

The reaction temperature is usually in a range of −20 to 100° C., and the reaction time is usually 1 to 24 hours.

After completion of the reaction, the compound (i) can be isolated by a treatment such as concentration of a reaction mixture. The isolated compound (i) can be further purified by distillation or the like.

Step 5-2:

The reaction is usually carried out in a solvent in the presence of a base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate, and organic bases such as triethylamine, 1,4-diazabicyclo[2.2.2]octane and 1,8-diazabicyclo[5.4.0]-7-undecene.

The amount of the base used in the reaction is usually 1 to 10 mol relative to 1 mol of the compound (i).

The amount of the compound (j) used in the reaction is usually 1 to 10 mol relative to 1 mol of the compound (i).

The reaction temperature is usually in a range of −20 to 100° C., and the reaction time is usually 1 to 24 hours.

After completion of the reaction, the compound (I-5) can be isolated by post-treatment, for example, by pouring a reaction mixture into water and extracting the resulting mixture with an organic solvent followed by concentration. The isolated compound (I-5) can be further purified by column chromatography, recrystallization or the like, if necessary.

Production Process 6

This process comprises reacting a compound (g) with a compound (j) as follows:

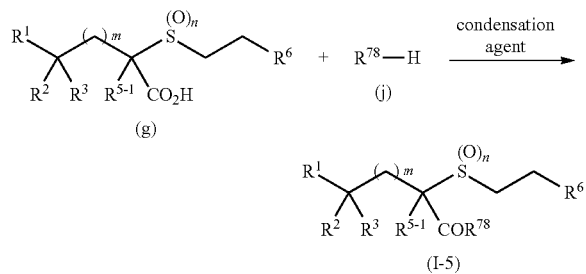

wherein $R^1$, $R^2$, $R^3$, $R^{5-1}$, $R^6$, m and n are as defined above, and $R^{78}$ represents $OR^7$ or $N(R^8)_2$ in which $R^7$ and $R^8$ are as defined above.

The reaction is usually carried out in a solvent in the presence of a condensation agent.

Examples of a solvent used in the reaction include ethers such as diethyl ether and tetrahydrofuran, organic sulfurs such as dimethyl sulfoxide and sulfolane, halogenated hydrocarbons such as chloroform, 1,2-dichloroethane and chlorobenzene, and aromatic hydrocarbons such as toluene and xylene.

Examples of a condensation agent used in the reaction include dicyclohexylcarbodiimide, N-(3-dimethylaminopropyl)-N'-ethylcarbodiimide and carbonyldiimidazole.

The amount of the condensation agent used in the reaction is usually 1 to 10 mol relative to 1 mol of the compound (g).

The amount of the compound (j) used in the reaction is usually 1 to 10 mol relative to 1 mol of the compound (g).

The reaction temperature is usually in a range of −20 to 100° C., and the reaction time is usually 1 to 24 hours.

After completion of the reaction, the compound (I-5) can be isolated by a treatment such as concentration. The isolated compound (I-5) can be further purified by column chromatography, recrystallization or the like, if necessary.

Production Process 7

Among the compounds of the present invention, a compound (I-1) that is a compound of the formula (I) wherein $R^5$ is a hydrogen atom can be produced, for example, by reacting a compound (c) with a compound (k) as follows:

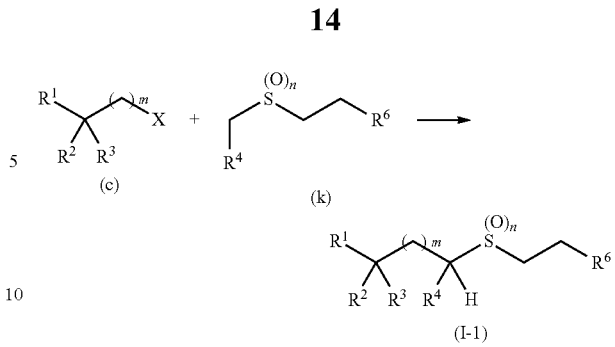

wherein $R^1$, $R^2$, $R^3$, $R^4$, $R^6$, X, m and n are as defined above.

The reaction is usually carried out in a solvent in the presence of a base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate, alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the base used in the reaction is usually 1 to 10 mol relative to 1 mol of the compound (k).

The amount of the compound (c) used in the reaction is usually 1 to 10 mol relative to 1 mol of the compound (k).

The reaction temperature is usually in a range of −100 to 100° C., and the reaction time is usually 1 to 24 hours.

After completion of the reaction, the compound (I-1) can be isolated by post-treatment, for example, by pouring a reaction mixture into water and extracting the resulting mixture with an organic solvent followed by concentration. The isolated compound (I-1) can be further purified by column chromatography, recrystallization or the like, if necessary.

Production Process 8

Among the compounds of the present invention, a compound (I-8) that is a compound of the formula (I) wherein $R^4$ is $C(=O)N(R^8)_2$ and n is 2 can be produced by reacting a compound (I-7) that is a compound of the formula (I) wherein $R^4$ is $C(=O)OR^7$ and n is 2 with a compound (p) as follows:

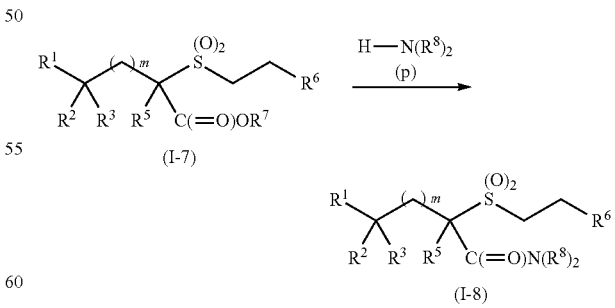

wherein $R^1$, $R^2$, $R^3$, $R^5$, $R^6$, $R^7$, $R^8$, m and n are as defined above.

The reaction is usually carried out in a solvent.

Examples of a solvent used in the reaction include ethers such as diethyl ether and tetrahydrofuran, organic sulfurs such as dimethyl sulfoxide and sulfolane, halogenated hydrocarbons such as chloroform, 1,2-dichloroethane and chlorobenzene, and aromatic hydrocarbons such as toluene and xylene.

The amount of the compound (p) used in the reaction is usually 1 to 10 mol relative to 1 mol of the compound (I-7).

The reaction temperature is usually in a range of −20 to 100° C., and the reaction time is usually 1 to 24 hours.

After completion of the reaction, the compound (I-8) can be isolated by a treatment such as concentration. The isolated compound (I-8) can be further purified by column chromatography, recrystallization or the like, if necessary.

Production Process 9

Among the compounds of the present invention, a compound (I-9) that is a compound of the formula (I) wherein $R^4$ is $C(=S)OR^7$ or $C(=S)N(R^8)_2$ can also be produced by reacting a compound (I-5) that is a compound of the formula (I) wherein $R^4$ is $C(=O)OR^7$ or $C(=O)N(R^8)_2$ with a sulfurizing agent (q) as follows:

wherein $R^1$, $R^2$, $R^3$, $R^5$, $R^6$, $R^{78}$, m and n are as defined above.

The reaction is usually carried out in a solvent.

Examples of a solvent used in the reaction include halogenated hydrocarbons such as chloroform, 1,2-dichloroethane and chlorobenzene, and aromatic hydrocarbons such as toluene and xylene.

Examples of the sulfurizing agent (q) used in the reaction include inorganic sulfur compounds such as hydrogen sulfide, diphosphorus pentasulfide, and organic sulfur compounds such as 2,4-bis(4-methoxyphenyl)-1,3-dithia-2,4-diphosphetane-2,4-disulfide.

The amount of the sulfurizing agent (q) used in the reaction is usually 0.5 to 10 mol relative to 1 mol of the compound (I-5).

The reaction temperature is usually in a range of 0 to 250° C., and the reaction time is usually 1 to 72 hours.

After completion of the reaction, the compound (I-9) can be isolated by a treatment such as concentration. The isolated compound (I-9) can be further purified by column chromatography, recrystallization or the like, if necessary.

Among the compounds of the present invention, a compound (I-10) that is a compound of the formula (I) wherein n is 0 can be produced, for example, by the following Production process 10 or 11.

Production Process 10

This process comprises reacting a compound (r) with a compound (m) as follows:

wherein $R^1$, $R^2$, $R^3$, $R^4$, $R^{5-2}$, $R^6$, m and X are as defined above.

The reaction is usually carried out in a solvent in the presence of a base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate, alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the base used in the reaction is usually 1 to 10 mol relative to 1 mol of the compound (r).

The amount of the compound (m) used in the reaction is usually 1 to 10 mol relative to 1 mol of the compound (r).

The reaction temperature is usually in a range of −20 to 100° C., and the reaction time is usually 1 to 24 hours.

After completion of the reaction, the compound (I-10) can be isolated by post-treatment, for example, by pouring a reaction mixture into water and extracting the resulting mixture with an organic solvent followed by concentration. The isolated compound (I-10) can be further purified by column chromatography, recrystallization or the like, if necessary.

Production Process 11

This process comprises reacting a compound (s) with a compound (o) as follows:

wherein $R^1$, $R^2$, $R^3$, $R^4$, $R^{5-2}$, $R^6$, m and X are as defined above.

The reaction is usually carried out in a solvent in the presence of a base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate, alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the base used in the reaction is usually 1 to 10 mol relative to 1 mol of the compound (o).

The amount of the compound (s) used in the reaction is usually 1 to 10 mol relative to 1 mol of the compound (o).

The reaction temperature is usually in a range of −20 to 100° C., and the reaction time is usually 1 to 24 hours.

After completion of the reaction, the compound (I-10) can be isolated by post-treatment, for example, by pouring a reaction mixture into water and extracting the resulting mixture with an organic solvent followed by concentration. The isolated compound (I-10) can be further purified by column chromatography, recrystallization or the like, if necessary.

Production Process 12

Among the compounds of the present invention, a compound (I-11) that is a compound of the formula (I) wherein n is 1 or 2 can be produced, for example, by oxidizing a compound (I-10) as follows:

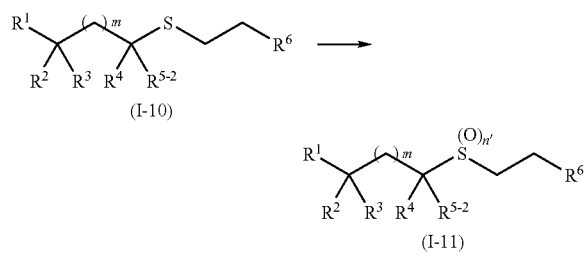

wherein $R^1$, $R^2$, $R^3$, $R^4$, $R^{5-2}$, $R^6$ and m are as defined above, and n' represents 1 or 2.

The reaction is usually carried out in a solvent in the presence of an oxidizing agent.

Examples of a solvent used in the reaction include alcohols such as methanol and ethanol, halogenated hydrocarbons such as dichloromethane and chloroform, aromatic hydrocarbons such as toluene and xylene, aliphatic carboxylic acids such as acetic acid and trifluoroacetic acid, water and a mixture thereof.

Examples of an oxidizing agent used in the reaction include organic peroxides such as peracetic acid, trifluoroperacetic acid and m-chloroperbenzoic acid, halogen molecules such as chlorine and bromine, halogen-containing imides such as N-chlorosuccinimide, halides such as perchloric acid (or its salt) and periodic acid (or its salt), permagnates such as potassium permanganate, chromates such as potassium chromate, and hydrogen peroxide.

The amount of the oxidizing agent used in the reaction is usually 1 to 10 mol relative to 1 mol of the compound (I-10).

The reaction temperature is usually in a range of −50 to 200° C., and the reaction time is usually 1 to 72 hours.

After completion of the reaction, the compound (I-11) can be isolated by post-treatment, for example, by pouring a reaction mixture into water and extracting the resulting mixture with an organic solvent followed by concentration. The isolated compound (I-11) can be further purified by column chromatography, recrystallization or the like, if necessary.

Next, a process for production of intermediates used for producing the compound of the present invention is explained by reference to Reference production processes.

Reference Production Process 1

The compound (g) can be produced by hydrolyzing a compound (I-6) as follows:

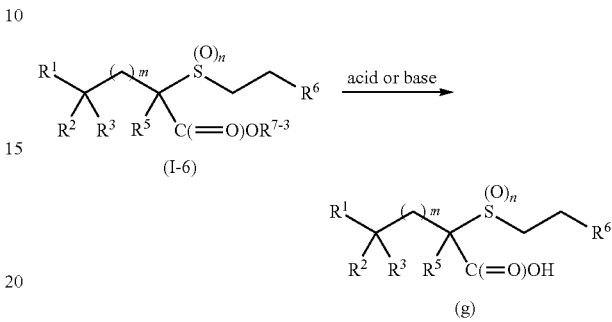

wherein $R^1$, $R^2$, $R^3$, $R^5$, $R^6$, m and n are as defined above, and $R^{7-3}$ is a methyl group or an ethyl group.

The reaction is usually carried out in an organic solvent in the presence of an acid or a base, and water.

Examples of an organic solvent used in the reaction include alcohols such as methanol and ethanol, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, aliphatic carboxylic acids such as formic acid and acetic acid, and a mixture thereof.

Examples of a base used in the reaction include inorganic bases such as sodium hydroxide and potassium hydroxide.

Examples of an acid used in the reaction include inorganic acids such as hydrochloric acid and sulfuric acid.

The amount of the acid or base used in the reaction is usually 1 to 10 mol relative to 1 mol of the compound (I-6).

The reaction temperature is usually in a range of −20 to 100° C., and the reaction time is usually 1 to 24 hours.

After completion of the reaction, the compound (g) can be isolated by post-treatment, for example, by adding water and/or an acid to a reaction mixture if necessary, and extracting the resulting mixture with an organic solvent followed by concentration. The isolated compound (g) can be further purified by column chromatography, recrystallization or the like, if necessary.

Reference Production Process 2

Among the compounds (d), a compound (d-1) that is a compound (d) wherein $R^5$ is a C1-C4 alkyl group can be produced, for example, by reacting the compound (a) with the compound (k) as follows:

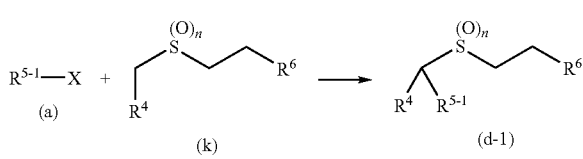

wherein $R^4$, $R^{5-1}$, $R^6$, n and X are as defined above.

The reaction is usually carried out in a solvent in the presence of a base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate, alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the base used in the reaction is usually 1 to 10 mol relative to 1 mol of the compound (k).

The amount of the compound (a) used in the reaction is usually 1 to 10 mol relative to 1 mol of the compound (k).

The reaction temperature is usually in a range of −20 to 100° C., and the reaction time is usually 1 to 24 hours.

After completion of the reaction, the compound (d-1) can be isolated by post-treatment, for example, by pouring a reaction mixture into water and extracting the resulting mixture with an organic solvent followed by concentration. The isolated compound (d-1) can be further purified by column chromatography, recrystallization or the like, if necessary.

Reference Production Process 3

Among the compounds (k), a compound (k-1) that is a compound (k) wherein n is 0 and a compound (k-2) that is a compound (k) wherein n is 1 or 2 can be produced by the following scheme:

The amount of the base used in the reaction is usually 1 to 10 mol relative to 1 mol of the compound (1).

The amount of the compound (m) used in the reaction is usually 1 to 10 mol relative to 1 mol of the compound (1).

The reaction temperature is usually in a range of −20 to 100° C., and the reaction time is usually 1 to 24 hours.

After completion of the reaction, the compound (k-1) can be isolated by post-treatment, for example, by pouring a reaction mixture into water and extracting the resulting mixture with an organic solvent followed by concentration. The isolated compound (k-1) can be further purified by column chromatography, recrystallization or the like, if necessary.

Step III-1-b:

The compound (k-1) can also be produced, for example, by reacting the compound (n) with the compound (o).

The reaction is usually carried out in a solvent in the presence of a base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate, alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the base used in the reaction is usually 1 to 10 mol relative to 1 mol of the compound (o).

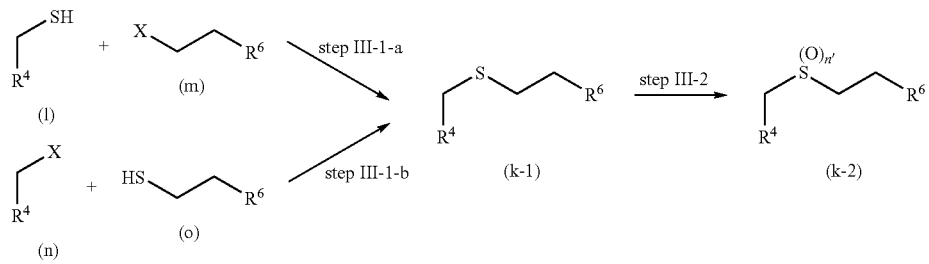

wherein $R^4$, $R^6$, X and n' are as defined above.

Step III-1-a:

The compound (k-1) can be produced, for example, by reacting the compound (1) with the compound (m).

The reaction is usually carried out in a solvent in the presence of a base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate, alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the compound (n) used in the reaction is usually 1 to 10 mol relative to 1 mol of the compound (o).

The reaction temperature is usually in a range of −20 to 100° C., and the reaction time is usually 1 to 24 hours.

After completion of the reaction, the compound (k-1) can be isolated by post-treatment, for example, by pouring a reaction mixture into water and extracting the resulting mixture with an organic solvent followed by concentration. The isolated compound (k-1) can be further purified by column chromatography, recrystallization or the like, if necessary.

Step III-2:

The compound (k-2) can be produced, for example, by oxidizing the compound (k-1).

The reaction is usually carried out in a solvent in the presence of an oxidizing agent.

Examples of a solvent used in the reaction include alcohols such as methanol and ethanol, halogenated hydrocarbons such as dichloromethane and chloroform, aromatic hydrocarbons such as toluene and xylene, aliphatic carboxylic acids such as acetic acid and trifluoroacetic acid, water and a mixture thereof.

Examples of an oxidizing agent used in the reaction include organic peroxides such as peracetic acid, trifluoroperacetic acid and m-chloroperbenzoic acid, halogen molecules such as chlorine and bromine, halogen-containing imides such as N-chlorosuccinimide, halides such as perchloric acid (or its salt) and periodic acid (or its salt), permagnates such as potassium permanganate, chromates such as potassium chromate, and hydrogen peroxide.

The amount of the oxidizing agent used in the reaction is usually 1 to 10 mol relative to 1 mol of the compound (k-1).

The reaction temperature is usually in a range of −50 to 200° C., and the reaction time is usually 1 to 72 hours.

After completion of the reaction, the compound (k-2) can be isolated by post-treatment, for example, by pouring a reaction mixture into water and extracting the resulting mixture with an organic solvent followed by concentration. The isolated compound (k-2) can be further purified by column chromatography, recrystallization or the like, if necessary.

The above compound (o) and (r) each can be produced, for example, in accordance with a method described in The Journal of Organic Chemistry, 27 (1), p. 93-95 (1962) and HETEROCYCLES, 24 (5), p. 1331-1346 (1986).

The above compound (s) can be produced, for example, in accordance with a method described in The Journal of Organic Chemistry, 18, p. 1112-1161 (1953).

The above compounds (a), (c), (j), (m), (n) and (p) are known or can be produced in accordance with a known method.

Examples of harmful arthropods on which the compound of the present invention exhibits a controlling effect include harmful insects and harmful mites, and more Hemiptera:

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*), green rice leafhopper (*Nephotettix virescens*), and tea green leafhopper (*Empoasca onukii*); aphids (Aphididae) such as cotton aphid (*Aphis gossypii*), green peach aphid (*Myzus persicae*), cabbage aphid (*Brevicoryne brassicae*), spiraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), and mealy plum aphid (*Hyalopterus pruni*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), and stink bug (*Halyomorpha mists*); whiteflies (Aleyrodidae) such as greenhouse whitefly (*Trialeurodes vaporariorum*), sweetpotato whitefly (*Bemisia tabaci*), citrus whitefly (*Dialeurodes citri*), and citrus spiny white fly (*Aleurocanthus spiniferus*); scales (Coccidae) such as Calfornia red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*), Japanese mealybug (*Planococcus kraunhiae*), Cosmstock mealybug (*Pseudococcus longispinis*), and white peach scale (*Pseudaulacaspis pentagons*); lace bugs (Tingidae); cimices such as *Cimex lectularius*; psyllids (Psyllidae), etc.;

Lepidoptera:

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), *Maruca testulalis*, cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes* sp.), oriental tea tortrix (*Homona magnanima*), apple tortrix (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); Carposinidae such as peach fruit moth (*Carposina niponensis*); lyonetiid moths (Lyonetiidae) such as *Lyonetia* spp.; tussock moths (Lymantriidae) such as *Lymantria* spp., and *Euproctis* spp.; yponomeutid moths (Yponomeutidae) such as diamondback (*Plutella xylostella*); gelechiid moths (Gelechiidae) such as pink bollworm (*Pectinophora gossypiella*), and potato tubeworm (*Phthorimaea operculella*); tiger moths and allies (Arctiidae) such as fall webworm (*Hyphantria cunea*); tineid moths (Tineidae) such as casemaking clothes moth (*Tinea translucens*), and webbing clothes moth (*Tineola bisselliella*), etc.;

Thysanoptera:

Yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*), etc.;

Diptera:

Culices (Calicidae) such as common mosquito (*Culex pipiens pallens*), *Culex tritaeniorhynchus*, and Southern house mosquito (*Culex quinquefasciatus*); *Aedes* spp. such as yellow fever mosquito (*Aedes aegypti*), and Asian tiger mosquito (*Aedes albopictus*); *Anopheles* spp. such as *Anopheles sinensis*; Chironomidae; Houseflies (Muscidae) such as housefly (*Musca domestica*), and false stable fly (*Muscina stabulans*); blow flies (Calliphoridae); flesh flies (Sarcophagidae); little house flies (Fanniidae); anthomyiid flies (Anthomyiidae) such as seedcorn maggot (*Delia platura*), and onion maggot (*Delia antiqua*); leafminer flies (Agromyzidae) such as rice leafminer (*Agromyza oryzae*), rice leafminer (*Hydrellia griseola*), tomato leafminer (*Liriomyza sativae*), legume leafminer (*Liriomyza trifolii*), and garden pea leafminer (*Chromatomyia horticola*); gout flies (Chloroidae) such as rice stem maggot (*Chlorops oryzae*); fruit flies (Tephritidae) such as melon fly (*Dacus cucurbitae*), and Mediteranean fruit fly (*Ceratitis capitata*); drosophila flies (Drosophilidae); humpbacked flies (Phoridae) such as *Megaselia spiracularis*; Psychodidae such as *Clogmia albipunctata*; Simuliidae; Tabanidae such as horsefly (*Tabanus trigonus*); stable flies (*Stomoxys calcitrans*), etc.;

Coleoptera:

Corn root worms (*Diabrotica* spp.) such as Western corn rootworm (*Diabrotica virgifera virgifera*), and Southern corn root worm (*Diabrotica undecimpunctata howardi*); scarabs (Scarabaeidae) such as cupreous chafer (*Anomala cuprea*), soybean beetle (*Anomala rufocuprea*), and Japanese beetle (*Popillia japonica*); weevils (Curculionidae) such as maize weevil (*Sitophilus zeamais*), rice water weevil (*Lissorhoptrus oryzophilus*), azuki bean weevil (*Callosobruchus chinensis*), rice curculio (*Echinocnemus squameus*), boll weevil (*Anthonomus grandis*), and hunting billbug (*Sphenophorus venatus*); darkling beetles (Tenebrionidae) such as yellow mealworm (*Tenebrio molitor*), and red flour beetle (*Tribolium*

*castaneum*); leaf beetles (Chrysomelidae) such as rice leaf beetle (*Oulema oryzae*), cucurbit leaf beetle (*Aulacophora femoralis*), striped flea beetle (*Phyllotreta striolata*), and Colorado beetle (*Leptinotarsa decemlineata*); dermestid beetles (Dermestidae) such as varied carper beetle (*Anthrenus verbasci*), and hide beetle (*Dermestes maculates*); deathwatch beetles (Anobiidae) such as cigarette beetle (*Lasioderma serricorne*); Epilachna such as twenty-eight-spotted ladybird (*Epilachna vigintioctopunctata*); bark beetles (Scolytidae) such as powder post beetle (*Lyctus brunneus*), and pine shoot beetle (*Tomicus piniperda*); false powderpost beetles (Bostrichidae); spider beetles (Ptinidae); longhorn beetles (Cerambycidae) such as white-spotted longicorn beetle (*Anoplophora malasiaca*); click beetles (*Agriotes* spp.); *Paederus fuscipes*, etc.;

Orthoptera:

Asiatic locust (*Locusta migratoria*), African mole cricket (*Gryllotalpa africana*), rice grasshopper (*Oxya yezoensis*), rice grasshopper (*Oxya japonica*), Grylloidea, etc.;

Shiphonaptera:

Cat flea (*Ctenocephalides felis*), dog flea (*Ctenocephalides canis*), human flea (*Pulex irritans*), oriental rat flea (*Xenopsylla cheopis*), etc.;

Anoplura:

Human body louse (*Pediculus humanus corporis*), crab louse (*Phthirus pubis*), short-nosed cattle louse (*Haematopinus eurysternus*), sheep louse (*Dalmalinia ovis*), hog louse (*Haematopinus suis*), etc.;

Hymenoptera:

Ants (Formicidae) such as *Monomorium pharaosis, Formica fusca japonica*, black house ant (*Ochetellus glaber*), *Pristomyrmex pungens, Pheidole noda*, leaf-cutting ant (*Acromyrmex* spp.), and fire ant (*Solenopsis* spp.); hornets (Vespidae); bethylid wasps (Betylidae); sawflies (Tenthredinidae) such as Cabbage sawfly (*Athalia rosae*), and *Athalia japonica*, etc.;

Blattodea:

Cockroaches (Blattariae) such as German cockroach (*Blattella germanica*), smokybrown cockroach (*Periplaneta fuliginosa*), American cockroach (*Periplaneta americana*), *Periplaneta brunnea*, and oriental cockroach (*Blatta orientalis*), etc.;

Isoptera

Termites (Termitidae) such as subterranean termites such as Japanese subterranean termite (*Reticulitermes speratus*), Formosan subterranean termite (*Coptotermes formosanus*), western drywood termite (*Incisitermes minor*), Daikoku drywood termite (*Cryptotermes domesticus*), *Odontotermes formosanus, Neotermes koshunesis, Glyptotermes satsumesis, Glyptotermes nakajimai, Glyptotermes fuscus, Glyptotermes kodamai, Glyptotermes kushimensis*, Japanese dampwood termite (*Hodotermopsis japonica*), *Coptotermes guangzhoensis, Reticulitermes miyatakei, Reticulitermes flavipes amamianus, Reticulitermes kanmonensis* (*Reticulitermes* sp.), *Nasutitermes takasagoensis, Pericapritermes nitobei, Sinocapritermes mushae*, etc.;

Acarina:

Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and *Oligonychus* spp.; eriophyid mites (Eriophyidae) such as pink citrus rust mite (*Aculops pelekassi*), *Phyllocoptruta citri*, tomato rust mite (*Aculops lycopersici*), purple tea mite (*Calacarus carinatus*), pink tea rust mite (*Acaphylla theavagran*), *Eriophyes chibaensis*, and apple rust mite (*Aculus schlechtendali*); tarosonemid mites (Tarsonemidae) such as broad mite (*Polyphagotarsonemus latus*); false spider mites (Tenuipalpidae) such as *Brevipalpus phoenicis*; Tuckerellidae; ticks (Ixodidae) such as *Haemaphysalis longicornis, Haemaphysalis flava*, American dog tick (*Dermacentor variabilis*), *Haemaphysalis flava, Dermacentor taiwanicus*, American dog tick (*Dermacentor variabilis*), *Ixodes ovatus, Ixodes persulcatus*, black legged tick (*Ixodes scapularis*), lone star tick (*Amblyomma americanum*), *Boophilus microplus*, and *Rhipicephalus sanguineus*; Psoroptidae such as ear mite (*Otodectes cynotis*); itch mites (Sarcoptidae) such as *Sarcoptes scabiei*; folicle mites (Demodicidae) such as dog folicle mite (*Demodex canis*); acarid mites (Acaridae) such as mold mite (*Tyrophagus putrescentiae*), and *Tyrophagus similis*; house dust mites (Pyroglyphidae) such as *Dermatophagoides farinae*, and *Dermatophagoides ptrenyssnus*; cheyletide mites (Cheyletidae) such as *Cheyletus eruditus, Cheyletus malaccensis*, and *Cheyletus moorei*; parasitoid mites (Dermanyssidae) such as tropical rat mite (*Ornithonyssus bacoti*), northern fowl mite (*Ornithonyssus sylviarum*), and poultry red mite (*Dermanyssus gallinae*); chiggers (Trombiculidae) such as *Leptotrombidium akamushi*; spiders (Araneae) such as Japanese foliage spider (*Chiracanthium japonicum*), redback spider (*Latrodectus hasseltii*), etc.;

Chilopoda: *Thereuonema hilgendorfi, Scolopendra subspinipes*, etc.;

Diplopoda: garden millipede (*Oxidus gracilis*), *Nedyopus tambanus*, etc.;

Isopoda: common pill bug (*Armadillidium vulgare*), etc.;

Gastropoda: *Limax marginatus, Limax flavus*, etc.

Although the pesticidal composition of the present invention may be the compound of the present invention itself, the pesticidal composition of the present invention usually comprises the compound of the present invention in combination with a solid carrier, a liquid carrier and/or a gaseous carrier, and if necessary, a surfactant or other pharmaceutical additives and takes the form of an emulsion, an oil, a shampoo formulation, a flowable formulation, a powder, a wettable powder, a granule, a paste, a microcapsule, a foam formulation, an aerosol, a carbon dioxide gas preparation, a tablet, a resin preparation or the like. The pesticidal composition of the present invention may be processed into a poison bait, a mosquito coil, an electric mosquito mat, a smoking agent, a fumigant or a sheet, and then be used.

The pesticidal composition of the present invention usually contains 0.1 to 95% by weight of the compound of the present invention.

Examples of the solid carrier include finely-divided powder or granules of clay (e.g., kaolin clay, diatomaceous earth, bentonite, Fubasami clay, acid clay, etc.), synthetic hydrated silicon oxide, talc, ceramics, other inorganic minerals (e.g., sericite, quartz, sulfur, activated carbon, calcium carbonate, hydrated silica, etc.), chemical fertilizers (e.g., ammonium sulfate, ammonium phosphate, ammonium nitrate, ammonium chloride, urea, etc.) and the like.

Examples of the liquid carrier include aromatic or aliphatic hydrocarbons (e.g., xylene, toluene, alkylnaphthalene, phenylxylylethane, kerosene, light oil, hexane, cyclohexane, etc.), halogenated hydrocarbons (e.g., chlorobenzene, dichloromethane, dichloroethane, trichloroethane, etc.), alcohols (e.g., methanol, ethanol, isopropyl alcohol, butanol, hexanol, ethylene glycol, etc.), ethers (e.g., diethyl ether, ethylene glycol dimethyl ether, diethylene glycol monomethyl ether, diethylene glycol monoethyl ether, propylene glycol monomethyl ether, tetrahydrofuran, dioxane, etc.), esters (e.g., ethyl acetate, butyl acetate, etc.), ketones (e.g., acetone, methyl ethyl ketone, methyl isobutyl ketone, cyclohexanone etc.), nitriles (e.g., acetonitrile, isobutyronitrile etc.), sulfoxides (e.g., dimethyl sulfoxide etc.), acid amides (e.g., N,N-dimethylformamide, N,N-dimethylacetamide etc.), pyrrolidones (e.g., N-methyl-2-pyrrolidone, N-octyl-2-pyrrolidone, etc.), propylene carbonate, ethyl lactate, 1,3-dimethyl-2-imidazolidinone, vegetable oils (e.g., soybean oil, cottonseed oil etc.), vegetable essential oils (e.g., orange oil, hyssop oil, lemon oil, etc.), water and the like.

Examples of the gaseous carrier include butane gas, chlorofluorocarbon, LPG (liquefied petroleum gas), dimethyl ether, carbon dioxide gas and the like.

Examples of the surfactant include alkyl sulfate salts, alkyl sulfonate salts, alkylaryl sulfonate salts, alkyl aryl ethers and their polyoxyethylated derivatives, polyethylene glycol ethers, polyhydric alcohol esters, and sugar alcohol derivatives.

Examples of other pharmaceutical additives include a binder, a dispersant, a stabilizer and the like, and specific examples thereof include casein, gelatin, polysaccharides (e.g., starch, gum arabic, cellulose derivatives, alginic acid, etc.), lignin derivatives, bentonite, saccharides, synthetic water-soluble polymers (e.g., polyvinyl alcohol, polyvinylpyrrolidone, polyacrylic acid, etc.), PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids, and fatty acid esters.

Examples of a base material for a resin preparation include vinyl chloride polymers, polyurethane and the like. To the base material, if necessary, a plasticizer such as phthalate (e.g., dimethyl phthalate, dioctyl phthalate, etc.), adipate, stearic acid or the like may be added. The resin preparation is obtained by kneading the compound of the present invention into the base material using a conventional kneading apparatus, followed by molding such as injection molding, extrusion molding, press molding or the like. The resulting resin preparation may be formed into the shape of a plate, a film, a tape, a net, a string or the like via a further step of molding, cutting, or the like, if necessary. These resin preparations may be used, for example, in the form of an animal collar, an animal ear tag, a sheet preparation, a lead, or a horticultural post.

Examples of a base material of a poison bait includes cereal powder, vegetable oil, sugar, crystalline cellulose and the like. To the base material, if necessary, an antioxidant such as dibutylhydroxytoluene or nordihydroguaiaretic acid, a preservative such as dehydroacetic acid, an agent for preventing children or pets from erroneously eating such as hot pepper powder, a pest-attractive perfume such as cheese perfume, onion perfume or peanut oil or the like may be added.

The pesticidal composition of the present invention can be applied, for example, to harmful arthropods directly and/or a place where harmful arthropods inhabit (e.g., plants, animals, soil, etc.).

When the pesticidal composition of the present invention is used for controlling pests in agriculture and forestry, the application amount is usually 1 to 10,000 g/ha, preferably 10 to 500 g/ha of the active ingredient. When the pesticidal composition of the present invention is the form of an emulsion, a wettable powder, a flowable formulation, or a microcapsule, it is usually used after dilution with water so as to have an active ingredient concentration of 0.01 to 1,000 ppm. When the pesticidal composition of the present invention is the form of a powder or a granule, it is usually used as it is. The pesticidal composition of the present invention as it is or as a dilution may be sprayed directly to plants to be protected from harmful arthropods. Alternatively, soil can be treated with the pesticidal composition of the present invention as it is or as a dilution to control harmful arthropods living in the soil. Seedbeds before planting or planting holes or plant feet in planting can be also treated with the pesticidal composition of the present invention as it is or as a dilution. Further, a sheet preparation of the pesticidal composition of the present invention may be applied by winding around plants, disposing in the vicinity of plants, laying on the soil surface at the plant feet, or the like.

The pesticidal composition of the present invention can be used in crop lands such as cultivated lands, paddy fields, lawns and orchards. The pesticidal composition of the present invention may control harmful arthropods in a crop land without causing drug damage to crop plants cultivated in the crop land.

Examples of such crop plants include

Agricultural crops: corn, rice, wheat, barley, rye, oat, sorghum, cotton, soybean, peanut, sarrazin, sugar beet, rapeseed, sunflower, sugar cane, tobacco etc.;

Vegetables: Solanaceae vegetables (eggplant, tomato, green pepper, hot pepper, potato etc.), Cucurbitaceae vegetables (cucumber, pumpkin, zucchini, watermelon, melon etc.), Cruciferae vegetables (Japanese radish, turnip, horseradish, kohlrabi, Chinese cabbage, cabbage, brown mustard, broccoli, cauliflower etc.), Compositae vegetables (burdock, garland chrysanthemum, artichoke, lettuce etc.), Liliaceae vegetables (Welsh onion, onion, garlic, asparagus etc.), Umbelliferae vegetables (carrot, parsley, celery, parsnip etc.), Chenopodiaceae vegetables (spinach, Swiss chard etc.), Labiatae vegetables (Japanese basil, mint, basil etc.), strawberry, sweat potato, yam, aroid etc.;

Flowers and ornamental plants;

Foliage plant;

Fruit trees: pomaceous fruits (apple, common pear, Japanese pear, Chinese quince, quince etc.), stone fleshy fruits (peach, plum, nectarine, Japanese plum, cherry, apricot, prune etc.), citrus plants (Satsuma mandarin, orange, lemon, lime, grapefruit etc.), nuts (chestnut, walnut, hazel nut, almond, pistachio, cashew nut, *macadamia* nut etc.), berry fruits (blueberry, cranberry, blackberry, raspberry etc.), grape, persimmon, olive, loquat, banana, coffee, date, coconut etc.;

Trees other than fruit trees: tea, mulberry, flowering trees and shrubs, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew) etc.

The aforementioned crop plants include those to which resistance to a herbicide, such as an HPPD inhibitor such as isoxaflutole, an ALS inhibitor such as imazethapyr or thifensulfuron-methyl, an EPSP synthesizing enzyme inhibitor, a glutamine synthesizing enzyme inhibitor, an acetyl CoA carboxylase inhibitor or bromoxynil, has been imparted by a classical breeding method, a genetic engineering technique or the like.

Examples of the crop plant to which resistance to a herbicide has been imparted by a classical breeding method include Clearfield (registered trademark) canola which is resistant to an imidazolinone herbicide such as imazethapyr, STS soybean which is resistant to a sulfonylurea ALS inhibitor herbicide such as thifensulfuron-methyl, and the like. Examples of the crop plant to which resistance to an acetyl CoA carboxylase inhibitor such as a trioxime or aryloxyphenoxypropionic acid herbicide has been imparted by a classical breeding method include SR corn and the like. For example, crop plants to which resistance to acetyl CoA carboxylase inhibitors has been imparted are found in Proc. Natl. Acad. Sci. USA 1990, 87, p. 7175-7179. In addition, a mutant acetyl CoA carboxylase which is resistant to an acetyl CoA carboxylase inhibitor is known, for example, in Weed Science 53: p. 728-746, 2005. When a gene encoding the mutant acetyl CoA carboxylase is introduced into a crop plant by a genetic engineering technique or when a mutation related to impartation of resistance is introduced into a gene encoding acetyl CoA carboxylase of a crop plant, a crop plant having the resistance to an acetyl CoA carboxylase inhibitor can be produced. Further, nucleic acids for introduction of a base substitution mutation can be introduced into the cell of a crop plant by chimeraplasty (see, Gura T. 1999, Repairing the Genome's Spelling Mistakes, Science 285: 316-318) to induce a site-directed amino acid mutation in the gene which is targeted by an acetyl CoA carboxylase inhibitor or herbicide of the crop plant, and thereby a crop plant resistant to an acetyl CoA carboxylase inhibitor or herbicide can be produced.

Examples of the crop plant to which resistance to a herbicide has been imparted by a genetic engineering technique include corn cultivars having resistance to glyphosate or glufosinate. Some of such corn cultivars are sold under the trade name of RoundupReady (registered trademark), LibertyLink (registered trademark), and the like.

The aforementioned crop plants include those to which ability to produce an insecticidal toxin, for example a selective toxin which is known to be produced by *Bacillus*, has been imparted by a genetic engineering technique.

Examples of the insecticidal toxin which is produced by such a genetically engineered plant include insecticidal proteins derived from *Bacillus cereus* and *Bacillus popilliae*; δ-endotoxins derived from *Bacillus thuringiensis*, such as Cry1Ab, Cry1Ac, Cry1F, Cry1Fa2, Cry2Ab, Cry3A, Cry3Bb1 and Cry9C; insecticidal proteins derived from *Bacillus thuringiensis*, such as VIP 1, VIP 2, VIP 3 and VIP 3A; insecticidal proteins derived from nematodes; toxins produced by animals such as scorpion toxins, spider toxins, bee toxins and insect-specific nerve toxins; fungal toxins; plant lectin; agglutinin; protease inhibitors such as trypsin inhibitors, serine protease inhibitors, patatin, cystatin, and papain inhibitors; ribosome-inactivating proteins (RIP) such as ricin, corn-RIP, abrin, saporin, and briodin; steroid metabolizing enzymes such as 3-hydroxysteroid oxidase, ecdysteroid-UDP-glucosyltransferase, and cholesterol oxidase; ecdysone inhibitors; HMG-COA reductase; ion channel inhibitors such as sodium channel inhibitors and calcium channel inhibitors; juvenile hormone esterase; diuretic hormone receptors; stilbene synthase; bibenzyl syntase; chitinase; and glucanase.

The insecticidal toxin which is produced by such a genetically engineered plant also includes hybrid toxins of different insecticidal proteins, for example, δ-endotoxins such as Cry1Ab, Cry1Ac, Cry1F, Cry1Fa2, Cry2Ab, Cry3A, Cry3Bb1 and Cry9C and insecticidal proteins such as VIP 1, VIP 2, VIP 3 and VIP 3A, and toxins in which a part of amino acids constituting an insecticidal protein is deleted or modified. The hybrid toxin is made by combining different domains of the insecticidal proteins by a genetic engineering technique. An example of the toxin in which a part of amino acids constituting an insecticidal protein is deleted includes Cry1Ab in which a part of amino acids is deleted. An example of the toxin in which a part of amino acids constituting an insecticidal protein is modified includes a toxin in which one or more of amino acids of a naturally occurring toxin are substituted.

The insecticidal toxin and the genetically engineered crop plant having the ability to produce the insecticidal toxin are described, for example, in EP-A-0 374 753, WO 93/07278, WO 95/34656, EP-A-0 427 529, EP-A-451878, WO 03/052073, and the like.

The genetically engineered crop plant having the ability to produce the insecticidal toxin particularly has resistance to attack by a coleopteran pest, dipteran pest or a lepidopteran pest.

Genetically engineered plants which have one or more pest-resistance genes and thereby produce one or more insecticidal toxins are also known, and some of them are commercially available. Examples of such genetically engineered plants include YieldGard (registered trademark) (a corn cultivar expressing Cry1Ab toxin), YieldGard Rootworm (registered trademark) (a corn cultivar expressing Cry3Bb1 toxin), YieldGard Plus (registered trademark) (a corn cultivar expressing Cry1Ab and Cry3Bb1 toxins), Heculex I (registered trademark) (a corn cultivar expressing Cry1Fa2 toxin and phosphinothricin N-acetyltransferase (PAT) for imparting resistance to gluphosinate), NuCOTN33B (registered trademark) (a cotton cultivar expressing Cry1Ac toxin), Bollgard I (registered trademark) (a cotton cultivar expressing Cry1Ac toxin), Bollgard II (registered trademark) (a cotton cultivar expressing Cry1Ac and Cry2Ab toxins), VIPCOT (registered trademark) (a cotton cultivar expressing VIP toxin), NewLeaf (registered trademark) (a potato cultivar expressing Cry3A toxin), NatureGard Agrisure GT Advantage (registered trademark) (GA21 glyphosate-resistance character), Agrisure CB Advantage (registered trademark) (Bt11 corn borer (CB) character), Protecta (registered trademark), and the like.

The aforementioned crop plants include those to which ability to produce an anti-pathogen substance has been imparted by a genetic engineering technique.

Examples of the anti-pathogen substance includes PR proteins (PRPs described in EP-A-0 392 225); ion channel inhibitors such as sodium channel inhibitors, and calcium channel inhibitors (e.g. KP1, KP4, KP6 toxins etc. produced by viruses); stilbene synthase; bibenzyl synthase; chitinase; glucanase; substances produced by microorganisms such as peptide antibiotics, heterocycle-containing antibiotics, and protein factors involved in plant disease-resistance (referred to as plant disease resistance genes and described in WO 03/000906); and the like. Such anti-pathogen substances and genetically engineered plants which produce the anti-pathogen substances are described in EP-A-0 392 225, WO 05/33818, EP-A-0 353 191, and the like.

When the pesticidal composition of the present invention is used for control of epidemic, the application amount is usually 0.001 to 10 mg/m$^3$ of the active ingredient for application to space, and 0.001 to 100 mg/m$^2$ of the active ingredient for application to a plane. The pesticidal composition in the form of an emulsion, a wettable powder or a flowable formulation is usually applied after dilution with water so as to contain usually 0.001 to 10,000 ppm of the active ingredient. The pesticidal composition in the form of an oil, an aerosol, a smoking agent or a poison bait is usually applied as it is.

When the pesticidal composition of the present invention is used for controlling external parasites of livestock such as a cow, a horse, a pig, a sheep, a goat and a chicken, or small animals such as a dog, a cat, a rat and a mouse, it can be applied to said animals by a known method in the veterinary filed. Specifically, when systemic control is intended, the pesticidal composition of the present invention is administered, for example, as a tablet, a mixture with feed, a suppository or an injection (e.g., intramuscularly, subcutaneously, intravenously, intraperitoneally, etc.). When non-systemic control is intended, a method of using the pesticidal composition of the present invention includes spraying, pour-on treatment or a spot-on treatment with the pesticidal composition in the form of an oil or an aqueous liquid, washing an animal with the pesticidal composition in the form of a shampoo formulation, and attachment of a collar or a ear tag made of the pesticidal composition in the form of a resin preparation to an animal. When administered to an animal, the amount of the compound of the present invention is usually in the range of 0.1 to 1,000 mg per 1 kg body weight of the animal.

The pesticidal composition of the present invention may be used in admixture or combination with other insecticides, nematocides, acaricides, fungicides, herbicides, plant growth regulators, synergists, fertilizers, soil conditioners, animal feed, and the like.

Examples of an active ingredient of such insecticide include (1) organic phosphorus compounds:
acephate, aluminum phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, cadusafos, and the like;

(2) carbamate compounds:
alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb, aldicarb, and the like;

(3) synthetic pyrethroid compounds:
acrinathrin, allethrin, benfluthrin, beta-cyfluthrin, bifenthrin, cycloprothrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, 2,3,5,6-tetrafluoro-4-methylbenzyl 2,2-dimethyl-3-(1-propenyl)cyclopropanecarboxylate, 2,3,5,6-tetrafluoro-4-(methoxymethyl)benzyl 2,2-dimethyl-3-(2-methyl-1-propenyl)cyclopropanecarboxylate, 2,3,5,6-tetrafluoro-4-(methoxymethyl)benzyl 2,2-dimethyl-3-(2-cyano-1-propenyl)cyclopropanecarboxylate, 2,3,5,6-tetrafluoro-4-(methoxymethyl)benzyl 2,2,3,3-tetramethylcyclopropanecarboxylate, and the like;

(4) nereistoxin compounds:
cartap, bensultap, thiocyclam, monosultap, bisultap, and the like;

(5) neonicotinoid compounds:
imidacloprid, nitenpyram, acetamiprid, thiamethoxam, thiacloprid, dinotefuran, clothianidin, and the like;

(6) benzoylurea compounds:
chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, triazuron, and the like;

(7) phenylpyrazole compounds:
acetoprole, ethiprole, fipronil, vaniliprole, pyriprole, pyrafluprole, and the like;

(8) Bt toxin insecticides:
live spores derived from and crystal toxins produced from Bacillus thuringiesis and a mixture thereof;

(9) hydrazine compounds:
chromafenozide, halofenozide, methoxyfenozide, tebufenozide, and the like;

(10) organic chlorine compounds:
aldrin, dieldrin, dienochlor, endosulfan, methoxychlor, and the like;

(11) natural insecticides:
machine oil, nicotine sulfate, and the like;

(12) other insecticides:
avermectin-B, bromopropylate, buprofezin, chlorphenapyr, cyromazine, D-D (1,3-dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, potassium oleate, protrifenbute, spiromesifen, sulfur, metaflumizone, spirotetramat, pyrifluquinazone, spinetoram, chlorantraniliprole, tralopyril, a compound represented by the following formula (A):

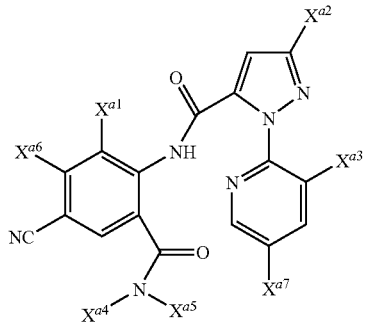

(A)

wherein $X^{a1}$ represents methyl, chlorine, bromine or fluorine, $X^{a2}$ represents fluorine, chlorine, bromine, C1-C4 haloalkyl or C1-C4 haloalkoxy, $X^{a3}$ represents fluorine, chlorine or bromine, $X^{a4}$ represents optionally substituted C1-C4 alkyl, optionally substituted C3-C4 alkenyl, optionally substituted C3-C4 alkynyl, optionally substituted C3-C5 cycloalkyl or hydrogen, $X^{a5}$ represents hydrogen or methyl, $X^{a6}$ represents hydrogen, fluorine or chlorine, and $X^{a7}$ represents hydrogen, fluorine or chlorine;

a compound represented by the following formula (B):

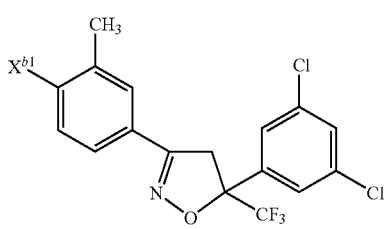

(B)

wherein $X^{b1}$ represents $X^{b2}$—NH—C(=O), $X^{b2}$—C(=O)—NH, $X^{b3}$—S(O), optionally substituted pyrrol-1-yl, optionally substituted imidazol-1-yl, optionally substituted pyrazol-1-yl, or optionally substituted 1,2,4-triazol-1-yl, $X^{b2}$ represents optionally substituted C1-C4 haloalkyl such as 2,2,2-trifluoroethyl or optionally substituted C3-C6 cycloalkyl such as cyclopropyl, and $X^{b3}$ represents optionally substituted C1-C4 alkyl such as methyl;
a compound represented by the following formula (C):

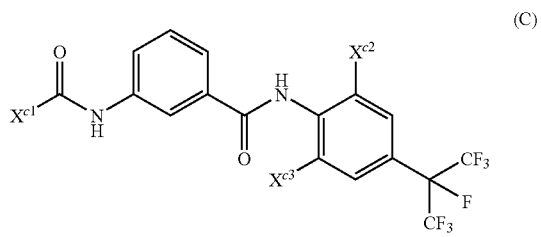

(C)

wherein $X^{c1}$ represents optionally substituted C1-C4 alkyl such as 3,3,3-trifluoropropyl, optionally substituted C1-C4 alkoxy such as 2,2,2-trichloroethoxy or optionally substituted phenyl such as phenyl, $X^{c2}$ represents methyl or trifluoromethylthio, and $X^{c3}$ represents methyl or halogen; and the like.

Examples of an active ingredient of the acaricide include acequinocyl, amitraz, benzoximate, bifenaate, bromopropylate, chinomethionat, chlorbenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite (BPPS), polynactins, pyridaben, pyrimidifen, tebufenpyrad, tetradifon, spirodiclofen, spiromesifen, spirotetramat, amidoflumet, cyenopyrafen, and the like.

Examples of the nematicide include DCIP, fosthiazate, levamisol hydrochloride, methylisothiocyanate, morantel tartarate, imicyafos, and the like.

Examples of an active ingredient of such fungicide include strobilurin compounds such as azoxystrobin; organophosphate compounds such as tolclofos-methyl; azole compounds such as triflumizole, pefurazoate and difenoconazole; fthalide, flutolanil, validamycin, probenazole, diclomezine, pencycuron, dazomet, kasugamycin, IBP, pyroquilon, oxolinic acid, tricyclazole, ferimzone, mepronil, EDDP, isoprothiolane, carpropamid, diclocymet, furametpyr, fludioxonil, procymidone and diethofencarb.

EXAMPLES

Hereinafter, the present invention will be explained in more detail by the following Production Examples, Formulation Examples and Test Examples, but the present invention is not limited to them.

First, Production Examples of the compound of the present invention is shown.

Production Example 1

To a solution of 2.0 g of 4,4,4-trifluoro-3-methylbutyl p-toluenesulfonate and 1.6 g of methyl (3,3,3-trifluoropropylsulfonyl)acetate in 50 ml of dimethyl sulfoxide was added 0.3 g of sodium hydride (60% in oil) at room temperature. The reaction mixture was heated to 60° C., stirred at the same temperature for 20 hours, and then allowed to stand to cool to nearly room temperature. To the reaction mixture was added 10% hydrochloric acid, and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 0.83 g of methyl 6,6,6-trifluoro-5-methyl-2-(3,3,3-trifluoropropylsulfonyl)hexanoate (hereinafter referred to as the present compound (1)).

The present compound (1):

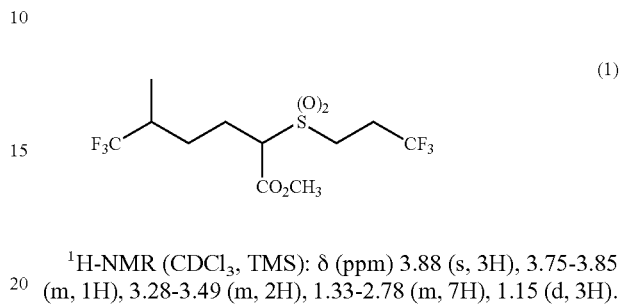

(1)

$^1$H-NMR (CDCl$_3$, TMS): δ (ppm) 3.88 (s, 3H), 3.75-3.85 (m, 1H), 3.28-3.49 (m, 2H), 1.33-2.78 (m, 7H), 1.15 (d, 3H).

Production Example 2

To a solution of 0.7 g of the present compound (1) in 30 ml of tetrahydrofuran was added 0.1 g of sodium hydride (60% in oil) at room temperature, and then stirred at the same temperature for 0.5 hours. To the mixture was added 0.3 g of N-chlorosuccinimide at room temperature, and then stirred for 10 hours. To the reaction mixture was added 10% hydrochloric acid, and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 0.70 g of methyl 2-chloro-6,6,6-trifluoro-5-methyl-2-(3,3,3-trifluoropropylsulfonyl)hexanoate (hereinafter referred to as the present compound (2)).

The present compound (2):

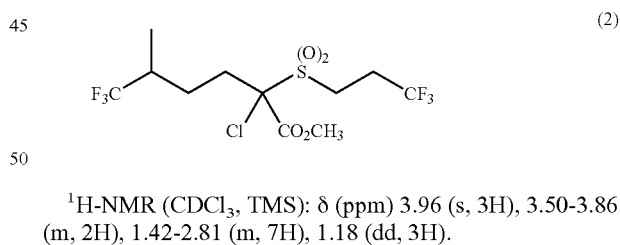

(2)

$^1$H-NMR (CDCl$_3$, TMS): δ (ppm) 3.96 (s, 3H), 3.50-3.86 (m, 2H), 1.42-2.81 (m, 7H), 1.18 (dd, 3H).

Production Example 3

To a solution of 0.6 g of the present compound (2) in 30 ml of methanol was added 0.6 ml of ammonia (7M methanol solution) at room temperature, and then stirred at the same temperature for 10 hours. The reaction mixture was concentrated under reduced pressure. The obtained residue was subjected to silica gel chromatography to obtain 0.45 g of 2-chloro-6,6,6-trifluoro-5-methyl-2-(3,3,3-trifluoropropylsulfonyl)hexanamide (hereinafter referred to as the present compound (3)).

The present compound (3):

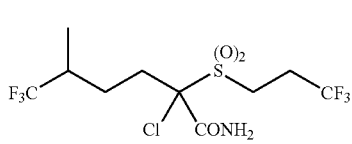

(3)

¹H-NMR (CDCl₃, TMS): δ (ppm) 6.88 (bs, 1H), 5.99 (bs, 1H), 3.33-3.68 (m, 2H), 1.35-2.81 (m, 7H), 1.17 (d, 3H).

Production Example 4

To a solution of 2.7 g of 3-(trifluoromethyl)pentyl p-toluenesulfonate and 2.0 g of methyl (3,3,3-trifluoropropylsulfonyl)acetate in 30 ml of dimethyl sulfoxide was added 1.2 g of potassium carbonate at room temperature. The reaction mixture was heated to 60° C., stirred at the same temperature for four days, and then allowed to stand to cool to nearly room temperature. To the reaction mixture was added 10% hydrochloric acid, and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 1.20 g of methyl 5-trifluoromethyl-2-(3,3,3-trifluoropropylsulfonyl)heptanoate (hereinafter referred to as the present compound (4)).

The present compound (4):

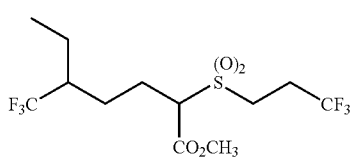

(4)

¹H-NMR (CDCl₃, TMS): δ (ppm) 3.89 (s, 3H), 3.78-3.84 (m, 1H), 3.28-3.50 (m, 2H), 1.43-2.78 (m, 9H), 1.00 (dt, 3H).

Production Example 5

To a solution of 1.1 g of the present compound (4) in 30 ml of tetrahydrofuran was added 0.1 g of sodium hydride (60% in oil) at room temperature and then stirred at the same temperature for 0.5 hours. To the mixture was added 0.4 g of N-chlorosuccinimide at room temperature, and stirred for 1 hour. To the reaction mixture was added 10% hydrochloric acid, and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 0.40 g of methyl 2-chloro-5-trifluoromethyl-2-(3,3,3-trifluoropropylsulfonyl)heptanoate (hereinafter referred to as the present compound (5)).

The present compound (5):

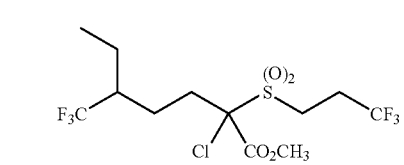

(5)

¹H-NMR (CDCl₃, TMS): δ (ppm) 3.96 (s, 3H), 3.50-3.85 (m, 2H), 1.43-2.80 (m, 9H), 1.01 (t, 3H).

Production Example 6

To a solution of 0.9 g of the present compound (5) in 20 ml of methanol was added 0.9 ml of ammonia (7M methanol solution) at room temperature, and stirred at the same temperature for 16 hours. The reaction mixture was concentrated under reduced pressure. The obtained residue was subjected to silica gel chromatography to obtain 0.65 g of 2-chloro-5-trifluoromethyl-2-(3,3,3-trifluoropropylsulfonyl)heptanamide (hereinafter referred to as the present compound (6)).

The present compound (6):

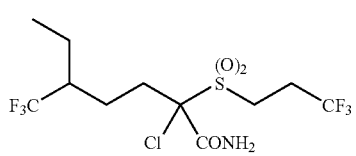

(6)

¹H-NMR (CDCl₃, TMS): δ (ppm) 6.88 (bs, 1H), 6.03 (bs, 1H), 3.31-3.78 (m, 2H), 1.42-2.80 (m, 9H), 1.01 (t, 3H).

Production Example 7

To a solution of 2.9 g of 4,4-dimethyl-3-(trifluoromethyl)pentyl p-toluenesulfonate and 2.0 g of methyl (3,3,3-trifluoropropylsulfonyl)acetate in 30 ml of dimethyl sulfoxide was added 1.2 g of potassium carbonate at room temperature. The reaction mixture was heated to 90° C., stirred at the same temperature for 6 hours, and then allowed to stand to cool to nearly room temperature. To the reaction mixture was added 10% hydrochloric acid, and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 2.00 g of methyl 6,6-dimethyl-5-trifluoromethyl-2-(3,3,3-trifluoropropylsulfonyl)heptanoate (hereinafter referred to as the present compound (7)).

The present compound (7):

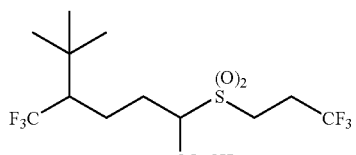

(7)

$^1$H-NMR (CDCl$_3$, TMS): δ (ppm) 3.89 (s, 3H), 3.78-3.89 (m, 1H), 3.24-3.50 (m, 2H), 1.49-2.78 (m, 7H), 1.03 (s, 9H).

Production Example 8

To a solution of 1.9 g of the present compound (7) in 30 ml of tetrahydrofuran was added 0.2 g of sodium hydride (60% in oil) at room temperature, and stirred at the same temperature for 0.5 hours. To the mixture was added 0.6 g of N-chlorosuccinimide at room temperature, and stirred for 1 hour. To the reaction mixture was added 10% hydrochloric acid, and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 0.40 g of methyl 2-chloro-6,6-dimethyl-5-trifluoromethyl-2-(3,3,3-trifluoropropylsulfonyl)heptanoate (hereinafter referred to as the present compound (8)).
The present compound (8):

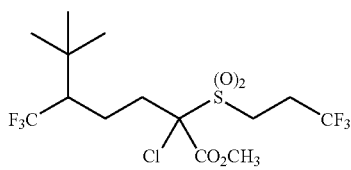

$^1$H-NMR (CDCl$_3$, TMS): δ (ppm) 3.95 (s, 3H), 3.49-3.83 (m, 2H), 1.60-2.90 (m, 7H), 1.05 (s, 9H).

Production Example 9

To a solution of 1.0 g of the present compound (8) in 50 ml of methanol was added 1.0 ml of ammonia (7M methanol solution) at room temperature, and stirred at the same temperature for 18 hours. The reaction mixture was concentrated under reduced pressure. The obtained residue was subjected to silica gel chromatography to obtain 0.53 g of 2-chloro-6,6-dimethyl-5-trifluoromethyl-2-(3,3,3-trifluoropropylsulfonyl)heptanamide (hereinafter referred to as the present compound (9)).
The present compound (9):

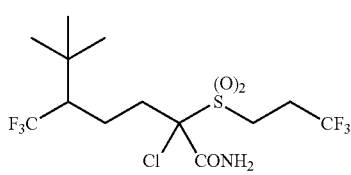

$^1$H-NMR (CDCl$_3$, TMS): δ (ppm) 6.88 (bs, 1H), 5.86 (bs, 1H), 3.33-3.78 (m, 2H), 1.50-2.89 (m, 7H), 1.05 (s, 9H).

Production Example 10

To a solution of 1.0 g of 4,4,4-trifluoro-3-methylbutyl p-toluenesulfonate and 0.7 g of (3,3,3-trifluoropropylsulfonyl)acetonitrile in 50 ml of dimethyl sulfoxide was added 0.5 g of potassium carbonate at room temperature, and then stirred at the same temperature for 16 hours. To the reaction mixture was added 10% hydrochloric acid, and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 0.50 g of 6,6,6-trifluoro-5-methyl-2-(3,3,3-trifluoropropylsulfonyl)hexanenitrile (hereinafter referred to as the present compound (10)).

The present compound (10):

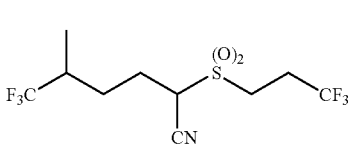

$^1$H-NMR (CDCl$_3$, TMS): δ (ppm) 3.88-3.95 (m, 1H), 3.35-3.60 (m, 2H), 1.50-2.96 (m, 7H), 1.20 (d, 3H).

Production Example 11

To a solution of 1.0 g of the present compound (4) in 30 ml of tetrahydrofuran was added 0.1 g of sodium hydride (60% in oil) at room temperature. The reaction mixture was stirred at the same temperature for 0.5 hours. To the reaction mixture was added 0.8 g of 1-fluoro-2,4,6-trimethylpyridinium trifluoromethanesulfonate, and then stirred for 1 hour. Thereto was added 10% hydrochloric acid and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 0.77 g of methyl 2-fluoro-5-(trifluoromethyl)-2-(3,3,3-trifluoropropylsulfonyl)heptanoate (hereinafter referred to as the present compound (11)).

The present compound (11):

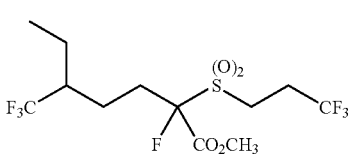

$^1$H-NMR (CDCl$_3$, TMS): δ (ppm) 3.99 (s, 3H), 3.24-3.52 (m, 2H), 2.58-2.80 (m, 2H), 1.42-2.14 (m, 7H), 1.00 (t, 3H).

Production Example 12

To a solution of 0.6 g of the present compound (11) in 30 ml of methanol was added 0.6 ml of ammonia (7M methanol solution) at room temperature, and then stirred at the same temperature for 3 days. The reaction mixture was concentrated under reduced pressure. The obtained residue was subjected to silica gel chromatography to obtain 0.32 g of 2-fluoro-5-(trifluoromethyl)-2-(3,3,3-trifluoropropylsulfonyl)heptanamide (hereinafter referred to as the present compound (12)).

The present compound (12):

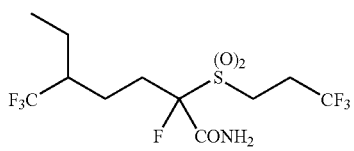

$^1$H-NMR (CDCl$_3$, TMS): δ (ppm) 6.58 (bs, 1H), 6.16 (bs, 1H), 3.26-3.53 (m, 2H), 1.43-2.80 (m, 9H), 1.00 (d, 3H).

Production Example 13

To a solution of 1.1 g of the present compound (4) and 0.4 g of iodomethane in 30 ml of N,N-dimethylformamide was added 0.1 g of sodium hydride (60% in oil) at room temperature. The reaction mixture was stirred at the same temperature for 1 hour. To the reaction mixture was added 10% hydrochloric acid and then extracted with ethyl acetate. The organic layer was washed sequentially with 10% hydrochloric acid and a saturated sodium chloride aqueous solution, dried over anhydrous magnesium sulfate, and then concentrated under reduced pressure. The obtained residue was dissolved in 20 ml of methanol. To the solution was added a potassium hydroxide aqueous solution (all of a solution of 0.5 g of potassium hydroxide in 5 ml of water) at room temperature, and stirred at the same temperature for 6 hours. To the reaction mixture was added 10% hydrochloric acid and then extracted with ethyl acetate. The organic layer was washed with a saturated sodium chloride aqueous solution, dried over anhydrous magnesium sulfate, and then concentrated under reduced pressure. The residue was dissolved in 20 ml of dichloromethane. To the solution was added dropwise 2 drops of N,N-dimethylformamide and then 0.2 ml of oxalyl chloride at room temperature. The reaction mixture was stirred at the same temperature for 2 hours and then concentrated under reduced pressure. The obtained residue was dissolved in 20 ml of tetrahydrofuran, and thereto was added dropwise 0.3 g of a 30% (w/w) ammonia aqueous solution at room temperature. The reaction mixture was stirred at the same temperature for 10 hours. Thereto was added a saturated ammonium chloride aqueous solution. The mixture was extracted with ethyl acetate and then concentrated under reduced pressure. The obtained residue was subjected to silica gel chromatography to obtain 0.30 g of 2-methyl-5-(trifluoromethyl)-2-(3,3,3-trifluoropropylsulfonyl)heptanamide (hereinafter referred to as the present compound (13)).

The present compound (13):

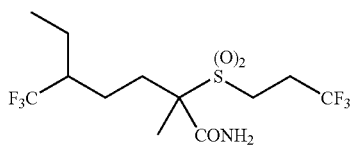

$^1$H-NMR (CDCl$_3$, TMS): δ (ppm) 6.57 (bs, 1H), 5.69 (bs, 1H), 3.13-3.42 (m, 2H), 2.60-2.77 (m, 2H), 1.40-2.36 (m, 7H), 1.67 (s, 3H), 1.00 (s, 3H).

Production Example 14

To a solution of 3.0 g of 3-(trifluoromethyl)pentyl methanesulfonate and 2.6 g of (3,3,3-trifluoropropylsulfonyl)acetonitrile in 50 ml of dimethyl sulfoxide was added 1.8 g of potassium carbonate at room temperature, heated to 60° C. and then stirred at the same temperature for 3 days. The reaction mixture was allowed to stand to cool to nearly room temperature. To the reaction mixture was added 10% hydrochloric acid, and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 3.00 g of 5-(trifluoromethyl)-2-(3,3,3-trifluoropropylsulfonyl)heptanenitrile (hereinafter referred to as the present compound (14)).

The present compound (14):

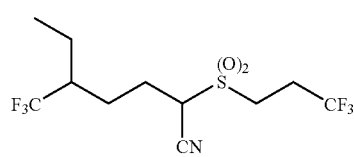

$^1$H-NMR (CDCl$_3$, TMS): δ (ppm) 3.91 (dd, 1H), 3.37-3.60 (m, 2H), 1.45-2.98 (m, 9H), 1.03 (t, 3H).

Production Example 15

To a solution of 0.9 g of the present compound (14) in 20 ml of tetrahydrofuran was added 0.1 g of sodium hydride (60% in oil) at room temperature. The reaction mixture was stirred at the same temperature for 0.5 hours. To the reaction mixture was added 0.8 g of 1-fluoro-2,4,6-trimethylpyridinium trifluoromethanesulfonate at the same temperature, and then stirred for 2 hours. Thereto was added 10% hydrochloric acid and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 0.50 g of 2-fluoro-5-(trifluoromethyl)-2-(3,3,3-trifluoropropylsulfonyl)heptanenitrile (hereinafter referred to as the present compound (15)).

The present compound (15):

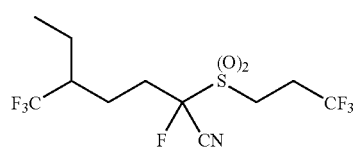

$^1$H-NMR (CDCl$_3$, TMS): δ (ppm) 3.50-3.65 (m, 2H), 1.46-2.90 (m, 9H), 1.04 (t, 3H).

Production Example 16

To a solution of 0.9 g of the present compound (14) in 20 ml of tetrahydrofuran was added 0.1 g of sodium hydride (60% in oil) at room temperature. The reaction mixture was stirred at the same temperature for 0.5 hours. To the reaction mixture was added 0.3 g of N-chlorosuccinimide at the same temperature, and then stirred for 2 hours. Thereto was added 10% hydrochloric acid and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 0.52 g of 2-chloro-5-(trifluoromethyl)-2-(3,3,3-trifluoropropylsulfonyl)heptanenitrile (hereinafter referred to as the present compound (16)).

The present compound (16):

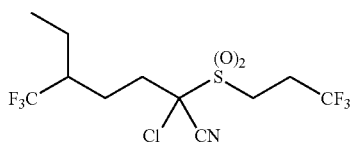
(16)

$^1$H-NMR (CDCl$_3$, TMS): δ (ppm) 3.63-3.82 (m, 2H), 1.45-2.90 (m, 9H), 1.04 (t, 3H).

Production Example 17

To a solution of 0.9 g of the present compound (14) and 0.4 g of iodomethane in 20 ml of N,N-dimethylformamide was added 0.1 g of sodium hydride (60% in oil) at room temperature. The reaction mixture was stirred at the same temperature for 20 hours. To the reaction mixture was added 10% hydrochloric acid and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 0.64 g of 2-methyl-5-(trifluoromethyl)-2-(3,3,3-trifluoropropylsulfonyl)heptanenitrile (hereinafter referred to as the present compound (17)).

The present compound (17):

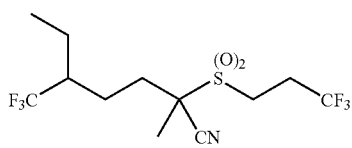
(17)

$^1$H-NMR (CDCl$_3$, TMS): δ (ppm) 3.35-3.53 (m, 2H), 1.42-2.98 (m, 9H), 1.80 (s, 3H), 1.03 (t, 3H).

Production Example 18

To a solution of 5.0 g of 4-methyl-3-(trifluoromethyl)pentyl methanesulfonate and 4.7 g of methyl (3,3,3-trifluoropropylsulfonyl)acetate in 100 ml of dimethyl sulfoxide was added 2.8 g of potassium carbonate at room temperature. The reaction mixture was heated to 60° C., stirred at the same temperature for 3 days and then allowed to stand to cool to nearly room temperature. To the reaction mixture was added 10% hydrochloric acid, and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 4.10 g of methyl 6-methyl-5-(trifluoromethyl)-2-(3,3,3-trifluoropropylsulfonyl)heptanoate (hereinafter referred to as the present compound (18)).

The present compound (18):

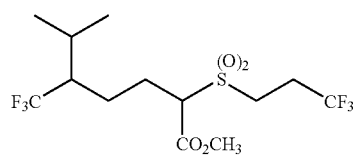
(18)

$^1$H-NMR (CDCl$_3$, TMS): δ (ppm) 3.89 (s, 3H), 3.78-3.85 (m, 1H), 3.25-3.50 (m, 2H), 1.48-2.98 (m, 8H), 0.89-1.02 (m, 6H).

Production Example 19

To a solution of 4.0 g of the present compound (18) in 100 ml of tetrahydrofuran was added 0.4 g of sodium hydride (60% in oil) at room temperature. The reaction mixture was stirred at the same temperature for 0.5 hours. To the reaction mixture was added 1.4 g of N-chlorosuccinimide, and then stirred for 1 hour. Thereto was added 10% hydrochloric acid and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 2.83 g of methyl 2-chloro-6-methyl-5-(trifluoromethyl)-2-(3,3,3-trifluoropropylsulfonyl)heptanoate (hereinafter referred to as the present compound (19)).

The present compound (19):

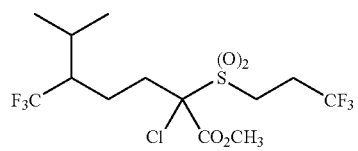
(19)

$^1$H-NMR (CDCl$_3$, TMS): δ (ppm) 3.95 (s, 3H), 3.49-3.84 (m, 2H), 1.58-2.84 (m, 8H), 0.93-1.06 (m, 6H)

Production Example 20

To a solution of 1.0 g of the present compound (19) in 50 ml of methanol was added 1.0 ml of ammonia (7M methanol solution) at room temperature, and then stirred at the same temperature for 16 hours. The reaction mixture was concentrated under reduced pressure. The obtained residue was subjected to silica gel chromatography to obtain 0.75 g of 2-chloro-6-methyl-5-(trifluoromethyl)-2-(3,3,3-trifluoropropylsulfonyl)heptanamide (hereinafter referred to as the present compound (20)).

The present compound (20):

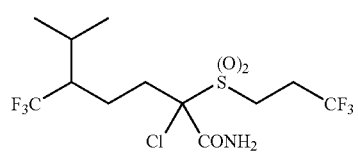
(20)

$^1$H-NMR (CDCl$_3$, TMS): δ (ppm) 6.87 (bs, 1H), 5.94 (bs, 1H), 3.35-3.76 (m, 2H), 1.48-2.82 (m, 8H), 0.94-1.05 (m, 6H).

Production Example 21

To a solution of 3.0 g of 3-(trifluoromethyl)-hexyl methanesulfonate and 2.8 g of methyl (3,3,3-trifluoropropylsulfonyl)acetate in 50 ml of dimethyl sulfoxide was added 1.7 g of potassium carbonate at room temperature. The reaction mixture was heated to 60° C., stirred at the same temperature for 2 days, and then allowed to stand to cool to nearly room temperature. To the reaction mixture was added 10% hydrochloric acid, and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 1.90 g of methyl 5-(trifluoromethyl)-2-(3,3,3-trifluoropropylsulfonyl)octanoate (hereinafter referred to as the present compound (21)).

The present compound (21):

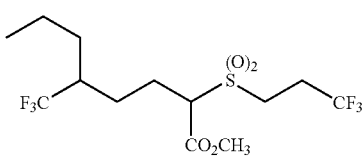

(21)

$^1$H-NMR (CDCl$_3$, TMS): δ (ppm) 3.89 (s, 3H), 3.78-3.85 (m, 1H), 3.25-3.50 (m, 2H), 1.30-2.78 (m, 11H), 0.94 (t, 3H).

Production Example 22

To a solution of 1.7 g of the present compound (21) in 50 ml of tetrahydrofuran was added 0.2 g of sodium hydride (60% in oil) at room temperature. The reaction mixture was stirred at the same temperature for 0.5 hours. To the reaction mixture was added 0.6 g of N-chlorosuccinimide, and then stirred for 2 hours. Thereto was added 10% hydrochloric acid and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 1.20 g of methyl 2-chloro-5-(trifluoromethyl)-2-(3,3,3-trifluoropropylsulfonyl)octanoate (hereinafter referred to as the present compound (22)).

The present compound (22):

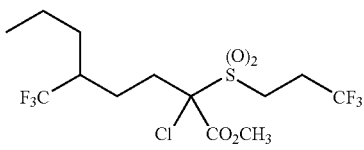

(22)

$^1$H-NMR (CDCl$_3$, TMS): δ (ppm) 3.95 (s, 3H), 3.50-3.80 (m, 2H), 1.30-2.80 (m, 2H), 1.30-2.80 (m, 11H), 0.95 (t, 3H).

Production Example 23

To a solution of 1.0 g of the present compound (22) in 30 ml of methanol was added 1.0 ml of ammonia (7M methanol solution) at room temperature, and then stirred at the same temperature for 4 days. The reaction mixture was concentrated under reduced pressure. The obtained residue was subjected to silica gel chromatography to obtain 0.60 g of 2-chloro-5-(trifluoromethyl)-2-(3,3,3-trifluoropropylsulfonyl)octanamide (hereinafter referred to as the present compound (23)).

The present compound (23):

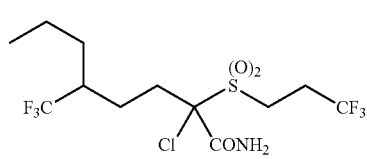

(23)

$^1$H-NMR (CDCl$_3$, TMS): δ (ppm) 6.87 (bs, 1H), 5.95 (bs, 1H), 3.34-3.78 (m, 2H), 1.32-2.80 (m, 11H), 0.95 (d, 3H).

Production Example 24

To a solution of 1.0 g of 4,4,4-trifluoro-3-methoxy-butyl p-toluenesulfonate and 0.8 g of methyl (3,3,3-trifluoropropylsulfonyl)acetate in 50 ml of dimethyl sulfoxide was added 0.4 g of potassium carbonate at room temperature, and the stirred at room temperature for 4 days. The reaction mixture was heated to 60° C., stirred at the same temperature for 20 hours, and then allowed to stand to cool to nearly room temperature. To the reaction mixture was added 10% hydrochloric acid, and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 0.62 g of methyl 6,6,6-trifluoro-5-methoxy-2-(3,3,3-trifluoropropylsulfonyl)hexanoate (hereinafter referred to as the present compound (24)).

The present compound (24):

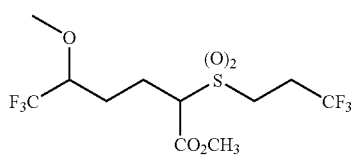

(24)

$^1$H-NMR (CDCl$_3$, TMS): δ (ppm) 3.89 (s, 1.5H), 3.88 (s, 1.5H), 3.84-3.95 (m, 1H), 3.30-3.63 (m, 6H), 1.63-2.82 (m, 6H).

Production Example 25

To a solution of 0.8 g of the present compound (24) in 30 ml of tetrahydrofuran was added 0.1 g of sodium hydride (60% in oil) at room temperature. The reaction mixture was stirred at the same temperature for 0.5 hours. To the reaction mixture was added 0.3 g of N-chlorosuccinimide at room temperature, and then stirred for 1 hour. Thereto was added 10% hydrochloric acid and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 0.50 g of methyl 2-chloro-6,6,6-trifluoro-5-methoxy-2-(3,3,3-trifluoropropylsulfonyl)hexanoate (hereinafter referred to as the present compound (25)).

The present compound (25):

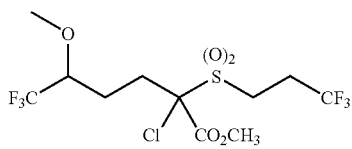

(25)

¹H-NMR (CDCl₃, TMS): δ (ppm) 3.95 (s, 3H), 3.49-3.89 (m, 3H), 3.56 (s, 3H), 1.78-2.91 (m, 6H).

Production Example 26

To a solution of 0.4 g of the present compound (25) in 20 ml of methanol was added 0.4 ml of ammonia (7M methanol solution) at room temperature, and then stirred at the same temperature for 2 days. The reaction mixture was concentrated under reduced pressure. The obtained residue was subjected to silica gel chromatography to obtain 0.28 g of 2-chloro-6,6,6-trifluoro-5-methoxy-2-(3,3,3-trifluoropropylsulfonyl)hexanamide (hereinafter referred to as the present compound (26)).
The present compound (26):

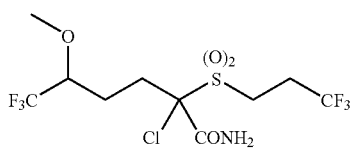

(26)

¹H-NMR (CDCl₃, TMS): δ (ppm) 6.88 (bs, 1H), 5.98 (bs, 1H), 3.37-3.80 (m, 3H), 3.58 (s, 3H), 1.66-2.86 (m, 6H).

Production Example 27

To a solution of 5.0 g of 4,4,4-trifluoro-3-methylthio-butyl methanesulfonate and 4.6 g of methyl (3,3,3-trifluoropropylsulfonyl)acetate in 50 ml of dimethyl sulfoxide was added 0.8 g of sodium hydride (60% in oil) at room temperature. The reaction mixture was heated to 60° C., stirred at the same temperature for 5 days, and then allowed to stand to cool to nearly room temperature. To the reaction mixture was added 10% hydrochloric acid, and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 2.00 g of methyl 6,6,6-trifluoro-5-methylthio-2-(3,3,3-trifluoropropylsulfonyl)hexanoate (hereinafter referred to as the present compound (27)).
The present compound (27):

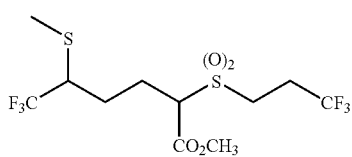

(27)

¹H-NMR (CDCl₃, TMS): δ (ppm) 3.89 (s, 3H), 3.81-3.93 (m, 1H), 3.30-3.52 (m, 2H), 2.13-3.00 (m, 5H), 2.23 (s, 1.5H), 2.22 (s, 1.5H), 1.58-2.08 (m, 2H).

Production Example 28

To a solution of 1.0 g of the present compound (27) in 30 ml of tetrahydrofuran was added 0.1 g of sodium hydride (60% in oil) at room temperature. The reaction mixture was stirred at the same temperature for 0.5 hours. To the reaction mixture was added 0.3 g of N-chlorosuccinimide at room temperature, and then stirred for 2 hours. Thereto was added 10% hydrochloric acid and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 0.80 g of methyl 2-chloro-6,6,6-trifluoro-5-methylthio-2-(3,3,3-trifluoropropylsulfonyl)hexanoate (hereinafter referred to as the present compound (28)).
The present compound (28):

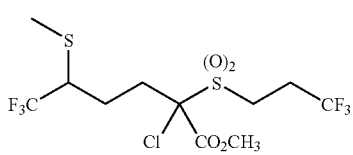

(28)

¹H-NMR (CDCl₃, TMS): δ (ppm) 3.97 (s, 1.5H), 3.96 (s, 1.5H), 3.50-3.85 (m, 2H), 1.70-3.10 (m, 7H), 2.23 (s, 1.5H), 2.22 (s, 1.5H).

Production Example 29

To a solution of 0.7 g of the present compound (28) in 20 ml of methanol was added 0.7 ml of ammonia (7M methanol solution) at room temperature, and then stirred at the same temperature for 16 hours. The reaction mixture was concentrated under reduced pressure. The obtained residue was subjected to silica gel chromatography to obtain 0.42 g of 2-chloro-6,6,6-trifluoro-5-methylthio-2-(3,3,3-trifluoropropylsulfonyl)hexanamide (hereinafter referred to as the present compound (29)).
The present compound (29):

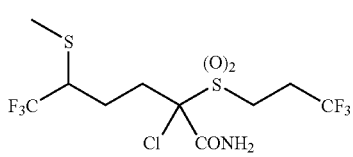

(29)

¹H-NMR (CDCl₃, TMS): δ (ppm) 6.87 (bs, 1H), 5.87 (bs, 1H), 3.38-3.78 (m, 2H), 2.22 (s, 3H), 1.50-3.08 (m, 7H).

Production Example 30

To a solution of 1.0 g of 4,4,4-trifluoro-3-methylthio-butyl methanesulfonate and 0.8 g of (3,3,3-trifluoropropylsulfonyl)acetonitrile in 30 ml of dimethyl sulfoxide was added 0.5 g of potassium carbonate at room temperature, heated to 60° C. and then stirred at the same temperature for 2 days. The reaction mixture was allowed to stand to cool to nearly room temperature. To the reaction mixture was added 10% hydrochloric acid, and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 0.49 g of 6,6,6-trifluoro-5-methylthio-2-(3,3,3-trifluoropropylsulfonyl)hexanenitrile (hereinafter referred to as the present compound (30)).
The present compound (30):

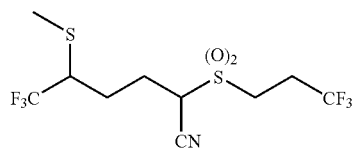
(30)

$^1$H-NMR (CDCl$_3$, TMS): δ (ppm) 3.99-4.13 (m, 1H), 3.40-3.64 (m, 2H), 1.66-3.64 (m, 10H).

Production Example 31

To a solution of 2.0 g of 4,4,5,5,5-pentafluoro-3-methylpentyl methanesulfonate and 1.7 g of methyl (3,3,3-trifluoropropylsulfonyl)acetate in 50 ml of dimethyl sulfoxide was added 1.0 g of potassium carbonate at room temperature, heated to 60° C. and then stirred at the same temperature for 7 days. The reaction mixture was allowed to stand to cool to nearly room temperature. To the reaction mixture was added 10% hydrochloric acid, and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 0.5 g of methyl 6,6,7,7,7-pentafluoro-5-methyl-2-(3,3,3-trifluoropropylsulfonyl)heptanoate, which was dissolved in 20 ml of tetrahydrofuran. To the solution was added 0.1 g of sodium hydride (60% in oil) at room temperature. The reaction mixture was stirred at the same temperature for 0.5 hours. To the reaction mixture was added 0.2 g of N-chlorosuccinimide at room temperature, and then stirred for 2 hours. Thereto was added 10% hydrochloric acid and then extracted with ethyl acetate. The organic layer was washed with a saturated sodium chloride aqueous solution, dried over anhydrous magnesium sulfate, and then concentrated under reduced pressure. The obtained residue was dissolved in 20 ml of methanol. To the solution was added 0.5 ml of ammonia (7M methanol solution) at room temperature, and then stirred at the same temperature for 30 hours. The reaction mixture was concentrated under reduced pressure. The obtained residue was subjected to silica gel chromatography to obtain 0.22 g of 2-chloro-6,6,7,7,7-pentafluoro-5-methyl-2-(3,3,3-trifluoropropylsulfonyl)heptanamide (hereinafter referred to as the present compound (31)).
The present compound (31):

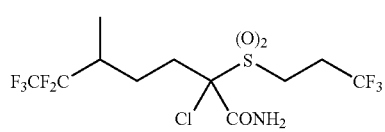
(31)

$^1$H-NMR (CDCl$_3$, TMS): δ (ppm) 6.97 (bs, 1H), 6.51 (bs, 1H), 3.35-3.80 (m, 2H), 1.35-2.83 (m, 7H), 1.19 (d, 3H).

Next, specific examples of the compound of the compound of the present invention are shown.

A compound represented by the formula (I-A):

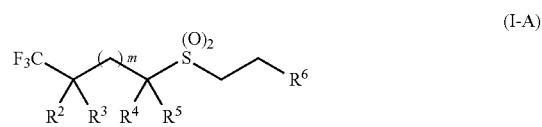
(I-A)

wherein $R^2$, $R^3$, $R^4$, $R^5$, $R^6$ and m represent combinations shown in the following Table 1 to Table 30.

TABLE 1

| $R^2$ | $R^3$ | $R^4$ | $R^5$ | $R^6$ | m |
|---|---|---|---|---|---|
| CH$_3$ | H | CN | H | CF$_3$ | 2 |
| CH$_3$ | H | CN | H | CF$_2$CF$_3$ | 2 |
| CH$_3$ | H | CN | H | CF$_2$CF$_2$CF$_3$ | 2 |
| CH$_3$ | H | CN | F | CF$_3$ | 2 |
| CH$_3$ | H | CN | F | CF$_2$CF$_3$ | 2 |
| CH$_3$ | H | CN | F | CF$_2$CF$_2$CF$_3$ | 2 |
| CH$_3$ | H | CN | Cl | CF$_3$ | 2 |
| CH$_3$ | H | CN | Cl | CF$_2$CF$_3$ | 2 |
| CH$_3$ | H | CN | Cl | CF$_2$CF$_2$CF$_3$ | 2 |
| CH$_3$ | H | CN | CH$_3$ | CF$_3$ | 2 |
| CH$_3$ | H | CN | CH$_3$ | CF$_2$CF$_3$ | 2 |
| CH$_3$ | H | CN | CH$_3$ | CF$_2$CF$_2$CF$_3$ | 2 |
| CH$_3$ | H | CO$_2$CH$_3$ | H | CF$_3$ | 2 |
| CH$_3$ | H | CO$_2$CH$_3$ | H | CF$_2$CF$_3$ | 2 |
| CH$_3$ | H | CO$_2$CH$_3$ | H | CF$_2$CF$_2$CF$_3$ | 2 |
| CH$_3$ | H | CO$_2$CH$_3$ | F | CF$_3$ | 2 |
| CH$_3$ | H | CO$_2$CH$_3$ | F | CF$_2$CF$_3$ | 2 |
| CH$_3$ | H | CO$_2$CH$_3$ | F | CF$_2$CF$_2$CF$_3$ | 2 |
| CH$_3$ | H | CO$_2$CH$_3$ | Cl | CF$_3$ | 2 |
| CH$_3$ | H | CO$_2$CH$_3$ | Cl | CF$_2$CF$_3$ | 2 |
| CH$_3$ | H | CO$_2$CH$_3$ | Cl | CF$_2$CF$_2$CF$_3$ | 2 |
| CH$_3$ | H | CO$_2$CH$_3$ | CH$_3$ | CF$_3$ | 2 |
| CH$_3$ | H | CO$_2$CH$_3$ | CH$_3$ | CF$_2$CF$_3$ | 2 |
| CH$_3$ | H | CO$_2$CH$_3$ | CH$_3$ | CF$_2$CF$_2$CF$_3$ | 2 |

TABLE 2

| $R^2$ | $R^3$ | $R^4$ | $R^5$ | $R^6$ | m |
|---|---|---|---|---|---|
| CH$_3$ | H | CONH$_2$ | H | CF$_3$ | 2 |
| CH$_3$ | H | CONH$_2$ | H | CF$_2$CF$_3$ | 2 |
| CH$_3$ | H | CONH$_2$ | H | CF$_2$CF$_2$CF$_3$ | 2 |
| CH$_3$ | H | CONH$_2$ | F | CF$_3$ | 2 |
| CH$_3$ | H | CONH$_2$ | F | CF$_2$CF$_3$ | 2 |
| CH$_3$ | H | CONH$_2$ | F | CF$_2$CF$_2$CF$_3$ | 2 |
| CH$_3$ | H | CONH$_2$ | Cl | CF$_3$ | 2 |
| CH$_3$ | H | CONH$_2$ | Cl | CF$_2$CF$_3$ | 2 |
| CH$_3$ | H | CONH$_2$ | Cl | CF$_2$CF$_2$CF$_3$ | 2 |
| CH$_3$ | H | CONH$_2$ | CH$_3$ | CF$_3$ | 2 |
| CH$_3$ | H | CONH$_2$ | CH$_3$ | CF$_2$CF$_3$ | 2 |
| CH$_3$ | H | CONH$_2$ | CH$_3$ | CF$_2$CF$_2$CF$_3$ | 2 |
| CH$_3$ | H | C(S)NH$_2$ | H | CF$_3$ | 2 |
| CH$_3$ | H | C(S)NH$_2$ | H | CF$_2$CF$_3$ | 2 |
| CH$_3$ | H | C(S)NH$_2$ | H | CF$_2$CF$_2$CF$_3$ | 2 |
| CH$_3$ | H | C(S)NH$_2$ | F | CF$_3$ | 2 |
| CH$_3$ | H | C(S)NH$_2$ | F | CF$_2$CF$_3$ | 2 |
| CH$_3$ | H | C(S)NH$_2$ | F | CF$_2$CF$_2$CF$_3$ | 2 |
| CH$_3$ | H | C(S)NH$_2$ | Cl | CF$_3$ | 2 |
| CH$_3$ | H | C(S)NH$_2$ | Cl | CF$_2$CF$_3$ | 2 |
| CH$_3$ | H | C(S)NH$_2$ | Cl | CF$_2$CF$_2$CF$_3$ | 2 |
| CH$_3$ | H | C(S)NH$_2$ | CH$_3$ | CF$_3$ | 2 |
| CH$_3$ | H | C(S)NH$_2$ | CH$_3$ | CF$_2$CF$_3$ | 2 |
| CH$_3$ | H | C(S)NH$_2$ | CH$_3$ | CF$_2$CF$_2$CF$_3$ | 2 |

TABLE 3

| R² | R³ | R⁴ | R⁵ | R⁶ | m |
|---|---|---|---|---|---|
| CH₃ | CH₃ | CN | H | CF₃ | 2 |
| CH₃ | CH₃ | CN | H | CF₂CF₃ | 2 |
| CH₃ | CH₃ | CN | H | CF₂CF₂CF₃ | 2 |
| CH₃ | CH₃ | CN | F | CF₃ | 2 |
| CH₃ | CH₃ | CN | F | CF₂CF₃ | 2 |
| CH₃ | CH₃ | CN | F | CF₂CF₂CF₃ | 2 |
| CH₃ | CH₃ | CN | Cl | CF₃ | 2 |
| CH₃ | CH₃ | CN | Cl | CF₂CF₃ | 2 |
| CH₃ | CH₃ | CN | Cl | CF₂CF₂CF₃ | 2 |
| CH₃ | CH₃ | CN | CH₃ | CF₃ | 2 |
| CH₃ | CH₃ | CN | CH₃ | CF₂CF₃ | 2 |
| CH₃ | CH₃ | CN | CH₃ | CF₂CF₂CF₃ | 2 |
| CH₃ | CH₃ | CO₂CH₃ | H | CF₃ | 2 |
| CH₃ | CH₃ | CO₂CH₃ | H | CF₂CF₃ | 2 |
| CH₃ | CH₃ | CO₂CH₃ | H | CF₂CF₂CF₃ | 2 |
| CH₃ | CH₃ | CO₂CH₃ | F | CF₃ | 2 |
| CH₃ | CH₃ | CO₂CH₃ | F | CF₂CF₃ | 2 |
| CH₃ | CH₃ | CO₂CH₃ | F | CF₂CF₂CF₃ | 2 |
| CH₃ | CH₃ | CO₂CH₃ | Cl | CF₃ | 2 |
| CH₃ | CH₃ | CO₂CH₃ | Cl | CF₂CF₃ | 2 |
| CH₃ | CH₃ | CO₂CH₃ | Cl | CF₂CF₂CF₃ | 2 |
| CH₃ | CH₃ | CO₂CH₃ | CH₃ | CF₃ | 2 |
| CH₃ | CH₃ | CO₂CH₃ | CH₃ | CF₂CF₃ | 2 |
| CH₃ | CH₃ | CO₂CH₃ | CH₃ | CF₂CF₂CF₃ | 2 |

TABLE 4

| R² | R³ | R⁴ | R⁵ | R⁶ | m |
|---|---|---|---|---|---|
| CH₃ | CH₃ | CONH₂ | H | CF₃ | 2 |
| CH₃ | CH₃ | CONH₂ | H | CF₂CF₃ | 2 |
| CH₃ | CH₃ | CONH₂ | H | CF₂CF₂CF₃ | 2 |
| CH₃ | CH₃ | CONH₂ | F | CF₃ | 2 |
| CH₃ | CH₃ | CONH₂ | F | CF₂CF₃ | 2 |
| CH₃ | CH₃ | CONH₂ | F | CF₂CF₂CF₃ | 2 |
| CH₃ | CH₃ | CONH₂ | Cl | CF₃ | 2 |
| CH₃ | CH₃ | CONH₂ | Cl | CF₂CF₃ | 2 |
| CH₃ | CH₃ | CONH₂ | Cl | CF₂CF₂CF₃ | 2 |
| CH₃ | CH₃ | CONH₂ | CH₃ | CF₃ | 2 |
| CH₃ | CH₃ | CONH₂ | CH₃ | CF₂CF₃ | 2 |
| CH₃ | CH₃ | CONH₂ | CH₃ | CF₂CF₂CF₃ | 2 |
| CH₃ | CH₃ | C(S)NH₂ | H | CF₃ | 2 |
| CH₃ | CH₃ | C(S)NH₂ | H | CF₂CF₃ | 2 |
| CH₃ | CH₃ | C(S)NH₂ | H | CF₂CF₂CF₃ | 2 |
| CH₃ | CH₃ | C(S)NH₂ | F | CF₃ | 2 |
| CH₃ | CH₃ | C(S)NH₂ | F | CF₂CF₃ | 2 |
| CH₃ | CH₃ | C(S)NH₂ | F | CF₂CF₂CF₃ | 2 |
| CH₃ | CH₃ | C(S)NH₂ | Cl | CF₃ | 2 |
| CH₃ | CH₃ | C(S)NH₂ | Cl | CF₂CF₃ | 2 |
| CH₃ | CH₃ | C(S)NH₂ | Cl | CF₂CF₂CF₃ | 2 |
| CH₃ | CH₃ | C(S)NH₂ | CH₃ | CF₃ | 2 |
| CH₃ | CH₃ | C(S)NH₂ | CH₃ | CF₂CF₃ | 2 |
| CH₃ | CH₃ | C(S)NH₂ | CH₃ | CF₂CF₂CF₃ | 2 |

TABLE 5

| R² | R³ | R⁴ | R⁵ | R⁶ | m |
|---|---|---|---|---|---|
| CH₂CH₃ | H | CN | H | CF₃ | 2 |
| CH₂CH₃ | H | CN | H | CF₂CF₃ | 2 |
| CH₂CH₃ | H | CN | H | CF₂CF₂CF₃ | 2 |
| CH₂CH₃ | H | CN | F | CF₃ | 2 |
| CH₂CH₃ | H | CN | F | CF₂CF₃ | 2 |
| CH₂CH₃ | H | CN | F | CF₂CF₂CF₃ | 2 |
| CH₂CH₃ | H | CN | Cl | CF₃ | 2 |
| CH₂CH₃ | H | CN | Cl | CF₂CF₃ | 2 |
| CH₂CH₃ | H | CN | Cl | CF₂CF₂CF₃ | 2 |
| CH₂CH₃ | H | CN | CH₃ | CF₃ | 2 |
| CH₂CH₃ | H | CN | CH₃ | CF₂CF₃ | 2 |
| CH₂CH₃ | H | CN | CH₃ | CF₂CF₂CF₃ | 2 |
| CH₂CH₃ | H | CO₂CH₃ | H | CF₃ | 2 |
| CH₂CH₃ | H | CO₂CH₃ | H | CF₂CF₃ | 2 |
| CH₂CH₃ | H | CO₂CH₃ | H | CF₂CF₂CF₃ | 2 |
| CH₂CH₃ | H | CO₂CH₃ | F | CF₃ | 2 |
| CH₂CH₃ | H | CO₂CH₃ | F | CF₂CF₃ | 2 |
| CH₂CH₃ | H | CO₂CH₃ | F | CF₂CF₂CF₃ | 2 |
| CH₂CH₃ | H | CO₂CH₃ | Cl | CF₃ | 2 |
| CH₂CH₃ | H | CO₂CH₃ | Cl | CF₂CF₃ | 2 |
| CH₂CH₃ | H | CO₂CH₃ | Cl | CF₂CF₂CF₃ | 2 |
| CH₂CH₃ | H | CO₂CH₃ | CH₃ | CF₃ | 2 |
| CH₂CH₃ | H | CO₂CH₃ | CH₃ | CF₂CF₃ | 2 |
| CH₂CH₃ | H | CO₂CH₃ | CH₃ | CF₂CF₂CF₃ | 2 |

TABLE 6

| R² | R³ | R⁴ | R⁵ | R⁶ | m |
|---|---|---|---|---|---|
| CH₂CH₃ | H | CONH₂ | H | CF₃ | 2 |
| CH₂CH₃ | H | CONH₂ | H | CF₂CF₃ | 2 |
| CH₂CH₃ | H | CONH₂ | H | CF₂CF₂CF₃ | 2 |
| CH₂CH₃ | H | CONH₂ | F | CF₃ | 2 |
| CH₂CH₃ | H | CONH₂ | F | CF₂CF₃ | 2 |
| CH₂CH₃ | H | CONH₂ | F | CF₂CF₂CF₃ | 2 |
| CH₂CH₃ | H | CONH₂ | Cl | CF₃ | 2 |
| CH₂CH₃ | H | CONH₂ | Cl | CF₂CF₃ | 2 |
| CH₂CH₃ | H | CONH₂ | Cl | CF₂CF₂CF₃ | 2 |
| CH₂CH₃ | H | CONH₂ | CH₃ | CF₃ | 2 |
| CH₂CH₃ | H | CONH₂ | CH₃ | CF₂CF₃ | 2 |
| CH₂CH₃ | H | CONH₂ | CH₃ | CF₂CF₂CF₃ | 2 |
| CH₂CH₃ | H | C(S)NH₂ | H | CF₃ | 2 |
| CH₂CH₃ | H | C(S)NH₂ | H | CF₂CF₃ | 2 |
| CH₂CH₃ | H | C(S)NH₂ | H | CF₂CF₂CF₃ | 2 |
| CH₂CH₃ | H | C(S)NH₂ | F | CF₃ | 2 |
| CH₂CH₃ | H | C(S)NH₂ | F | CF₂CF₃ | 2 |
| CH₂CH₃ | H | C(S)NH₂ | F | CF₂CF₂CF₃ | 2 |
| CH₂CH₃ | H | C(S)NH₂ | Cl | CF₃ | 2 |
| CH₂CH₃ | H | C(S)NH₂ | Cl | CF₂CF₃ | 2 |
| CH₂CH₃ | H | C(S)NH₂ | Cl | CF₂CF₂CF₃ | 2 |
| CH₂CH₃ | H | C(S)NH₂ | CH₃ | CF₃ | 2 |
| CH₂CH₃ | H | C(S)NH₂ | CH₃ | CF₂CF₃ | 2 |
| CH₂CH₃ | H | C(S)NH₂ | CH₃ | CF₂CF₂CF₃ | 2 |

TABLE 7

| R² | R³ | R⁴ | R⁵ | R⁶ | m |
|---|---|---|---|---|---|
| CH₂CH₃ | CH₃ | CN | H | CF₃ | 2 |
| CH₂CH₃ | CH₃ | CN | H | CF₂CF₃ | 2 |
| CH₂CH₃ | CH₃ | CN | H | CF₂CF₂CF₃ | 2 |
| CH₂CH₃ | CH₃ | CN | F | CF₃ | 2 |
| CH₂CH₃ | CH₃ | CN | F | CF₂CF₃ | 2 |
| CH₂CH₃ | CH₃ | CN | F | CF₂CF₂CF₃ | 2 |
| CH₂CH₃ | CH₃ | CN | Cl | CF₃ | 2 |
| CH₂CH₃ | CH₃ | CN | Cl | CF₂CF₃ | 2 |
| CH₂CH₃ | CH₃ | CN | Cl | CF₂CF₂CF₃ | 2 |
| CH₂CH₃ | CH₃ | CN | CH₃ | CF₃ | 2 |
| CH₂CH₃ | CH₃ | CN | CH₃ | CF₂CF₃ | 2 |
| CH₂CH₃ | CH₃ | CN | CH₃ | CF₂CF₂CF₃ | 2 |
| CH₂CH₃ | CH₃ | CO₂CH₃ | H | CF₃ | 2 |
| CH₂CH₃ | CH₃ | CO₂CH₃ | H | CF₂CF₃ | 2 |
| CH₂CH₃ | CH₃ | CO₂CH₃ | H | CF₂CF₂CF₃ | 2 |
| CH₂CH₃ | CH₃ | CO₂CH₃ | F | CF₃ | 2 |
| CH₂CH₃ | CH₃ | CO₂CH₃ | F | CF₂CF₃ | 2 |
| CH₂CH₃ | CH₃ | CO₂CH₃ | F | CF₂CF₂CF₃ | 2 |
| CH₂CH₃ | CH₃ | CO₂CH₃ | Cl | CF₃ | 2 |
| CH₂CH₃ | CH₃ | CO₂CH₃ | Cl | CF₂CF₃ | 2 |
| CH₂CH₃ | CH₃ | CO₂CH₃ | Cl | CF₂CF₂CF₃ | 2 |
| CH₂CH₃ | CH₃ | CO₂CH₃ | CH₃ | CF₃ | 2 |
| CH₂CH₃ | CH₃ | CO₂CH₃ | CH₃ | CF₂CF₃ | 2 |
| CH₂CH₃ | CH₃ | CO₂CH₃ | CH₃ | CF₂CF₂CF₃ | 2 |

TABLE 8

| R² | R³ | R⁴ | R⁵ | R⁶ | m |
|---|---|---|---|---|---|
| CH₂CH₃ | CH₃ | CONH₂ | H | CF₃ | 2 |
| CH₂CH₃ | CH₃ | CONH₂ | H | CF₂CF₃ | 2 |
| CH₂CH₃ | CH₃ | CONH₂ | H | CF₂CF₂CF₃ | 2 |
| CH₂CH₃ | CH₃ | CONH₂ | F | CF₃ | 2 |
| CH₂CH₃ | CH₃ | CONH₂ | F | CF₂CF₃ | 2 |
| CH₂CH₃ | CH₃ | CONH₂ | F | CF₂CF₂CF₃ | 2 |
| CH₂CH₃ | CH₃ | CONH₂ | Cl | CF₃ | 2 |
| CH₂CH₃ | CH₃ | CONH₂ | Cl | CF₂CF₃ | 2 |
| CH₂CH₃ | CH₃ | CONH₂ | Cl | CF₂CF₂CF₃ | 2 |
| CH₂CH₃ | CH₃ | CONH₂ | CH₃ | CF₃ | 2 |
| CH₂CH₃ | CH₃ | CONH₂ | CH₃ | CF₂CF₃ | 2 |
| CH₂CH₃ | CH₃ | CONH₂ | CH₃ | CF₂CF₂CF₃ | 2 |
| CH₂CH₃ | CH₃ | C(S)NH₂ | H | CF₃ | 2 |
| CH₂CH₃ | CH₃ | C(S)NH₂ | H | CF₂CF₃ | 2 |
| CH₂CH₃ | CH₃ | C(S)NH₂ | H | CF₂CF₂CF₃ | 2 |
| CH₂CH₃ | CH₃ | C(S)NH₂ | F | CF₃ | 2 |
| CH₂CH₃ | CH₃ | C(S)NH₂ | F | CF₂CF₃ | 2 |
| CH₂CH₃ | CH₃ | C(S)NH₂ | F | CF₂CF₂CF₃ | 2 |
| CH₂CH₃ | CH₃ | C(S)NH₂ | Cl | CF₃ | 2 |
| CH₂CH₃ | CH₃ | C(S)NH₂ | Cl | CF₂CF₃ | 2 |
| CH₂CH₃ | CH₃ | C(S)NH₂ | Cl | CF₂CF₂CF₃ | 2 |
| CH₂CH₃ | CH₃ | C(S)NH₂ | CH₃ | CF₃ | 2 |
| CH₂CH₃ | CH₃ | C(S)NH₂ | CH₃ | CF₂CF₃ | 2 |
| CH₂CH₃ | CH₃ | C(S)NH₂ | CH₃ | CF₂CF₂CF₃ | 2 |

TABLE 9

| R² | R³ | R⁴ | R⁵ | R⁶ | m |
|---|---|---|---|---|---|
| CH(CH₃)₂ | H | CN | H | CF₃ | 2 |
| CH(CH₃)₂ | H | CN | H | CF₂CF₃ | 2 |
| CH(CH₃)₂ | H | CN | H | CF₂CF₂CF₃ | 2 |
| CH(CH₃)₂ | H | CN | F | CF₃ | 2 |
| CH(CH₃)₂ | H | CN | F | CF₂CF₃ | 2 |
| CH(CH₃)₂ | H | CN | F | CF₂CF₂CF₃ | 2 |
| CH(CH₃)₂ | H | CN | Cl | CF₃ | 2 |
| CH(CH₃)₂ | H | CN | Cl | CF₂CF₃ | 2 |
| CH(CH₃)₂ | H | CN | Cl | CF₂CF₂CF₃ | 2 |
| CH(CH₃)₂ | H | CN | CH₃ | CF₃ | 2 |
| CH(CH₃)₂ | H | CN | CH₃ | CF₂CF₃ | 2 |
| CH(CH₃)₂ | H | CN | CH₃ | CF₂CF₂CF₃ | 2 |
| CH(CH₃)₂ | H | CO₂CH₃ | H | CF₃ | 2 |
| CH(CH₃)₂ | H | CO₂CH₃ | H | CF₂CF₃ | 2 |
| CH(CH₃)₂ | H | CO₂CH₃ | H | CF₂CF₂CF₃ | 2 |
| CH(CH₃)₂ | H | CO₂CH₃ | F | CF₃ | 2 |
| CH(CH₃)₂ | H | CO₂CH₃ | F | CF₂CF₃ | 2 |
| CH(CH₃)₂ | H | CO₂CH₃ | F | CF₂CF₂CF₃ | 2 |
| CH(CH₃)₂ | H | CO₂CH₃ | Cl | CF₃ | 2 |
| CH(CH₃)₂ | H | CO₂CH₃ | Cl | CF₂CF₃ | 2 |
| CH(CH₃)₂ | H | CO₂CH₃ | Cl | CF₂CF₂CF₃ | 2 |
| CH(CH₃)₂ | H | CO₂CH₃ | CH₃ | CF₃ | 2 |
| CH(CH₃)₂ | H | CO₂CH₃ | CH₃ | CF₂CF₃ | 2 |
| CH(CH₃)₂ | H | CO₂CH₃ | CH₃ | CF₂CF₂CF₃ | 2 |

TABLE 10

| R² | R³ | R⁴ | R⁵ | R⁶ | m |
|---|---|---|---|---|---|
| CH(CH₃)₂ | H | CONH₂ | H | CF₃ | 2 |
| CH(CH₃)₂ | H | CONH₂ | H | CF₂CF₃ | 2 |
| CH(CH₃)₂ | H | CONH₂ | H | CF₂CF₂CF₃ | 2 |
| CH(CH₃)₂ | H | CONH₂ | F | CF₃ | 2 |
| CH(CH₃)₂ | H | CONH₂ | F | CF₂CF₃ | 2 |
| CH(CH₃)₂ | H | CONH₂ | F | CF₂CF₂CF₃ | 2 |
| CH(CH₃)₂ | H | CONH₂ | Cl | CF₃ | 2 |
| CH(CH₃)₂ | H | CONH₂ | Cl | CF₂CF₃ | 2 |
| CH(CH₃)₂ | H | CONH₂ | Cl | CF₂CF₂CF₃ | 2 |
| CH(CH₃)₂ | H | CONH₂ | CH₃ | CF₃ | 2 |
| CH(CH₃)₂ | H | CONH₂ | CH₃ | CF₂CF₃ | 2 |
| CH(CH₃)₂ | H | CONH₂ | CH₃ | CF₂CF₂CF₃ | 2 |
| CH(CH₃)₂ | H | C(S)NH₂ | H | CF₃ | 2 |
| CH(CH₃)₂ | H | C(S)NH₂ | H | CF₂CF₃ | 2 |
| CH(CH₃)₂ | H | C(S)NH₂ | H | CF₂CF₂CF₃ | 2 |
| CH(CH₃)₂ | H | C(S)NH₂ | F | CF₃ | 2 |
| CH(CH₃)₂ | H | C(S)NH₂ | F | CF₂CF₃ | 2 |
| CH(CH₃)₂ | H | C(S)NH₂ | F | CF₂CF₂CF₃ | 2 |
| CH(CH₃)₂ | H | C(S)NH₂ | Cl | CF₃ | 2 |
| CH(CH₃)₂ | H | C(S)NH₂ | Cl | CF₂CF₃ | 2 |
| CH(CH₃)₂ | H | C(S)NH₂ | Cl | CF₂CF₂CF₃ | 2 |
| CH(CH₃)₂ | H | C(S)NH₂ | CH₃ | CF₃ | 2 |
| CH(CH₃)₂ | H | C(S)NH₂ | CH₃ | CF₂CF₃ | 2 |
| CH(CH₃)₂ | H | C(S)NH₂ | CH₃ | CF₂CF₂CF₃ | 2 |

TABLE 11

| R² | R³ | R⁴ | R⁵ | R⁶ | m |
|---|---|---|---|---|---|
| CH(CH₃)₂ | CH₃ | CN | H | CF₃ | 2 |
| CH(CH₃)₂ | CH₃ | CN | H | CF₂CF₃ | 2 |
| CH(CH₃)₂ | CH₃ | CN | H | CF₂CF₂CF₃ | 2 |
| CH(CH₃)₂ | CH₃ | CN | F | CF₃ | 2 |
| CH(CH₃)₂ | CH₃ | CN | F | CF₂CF₃ | 2 |
| CH(CH₃)₂ | CH₃ | CN | F | CF₂CF₂CF₃ | 2 |
| CH(CH₃)₂ | CH₃ | CN | Cl | CF₃ | 2 |
| CH(CH₃)₂ | CH₃ | CN | Cl | CF₂CF₃ | 2 |
| CH(CH₃)₂ | CH₃ | CN | Cl | CF₂CF₂CF₃ | 2 |
| CH(CH₃)₂ | CH₃ | CN | CH₃ | CF₃ | 2 |
| CH(CH₃)₂ | CH₃ | CN | CH₃ | CF₂CF₃ | 2 |
| CH(CH₃)₂ | CH₃ | CN | CH₃ | CF₂CF₂CF₃ | 2 |
| CH(CH₃)₂ | CH₃ | CO₂CH₃ | H | CF₃ | 2 |
| CH(CH₃)₂ | CH₃ | CO₂CH₃ | H | CF₂CF₂CF₃ | 2 |
| CH(CH₃)₂ | CH₃ | CO₂CH₃ | F | CF₃ | 2 |
| CH(CH₃)₂ | CH₃ | CO₂CH₃ | F | CF₂CF₃ | 2 |
| CH(CH₃)₂ | CH₃ | CO₂CH₃ | F | CF₂CF₂CF₃ | 2 |
| CH(CH₃)₂ | CH₃ | CO₂CH₃ | Cl | CF₃ | 2 |
| CH(CH₃)₂ | CH₃ | CO₂CH₃ | Cl | CF₂CF₃ | 2 |
| CH(CH₃)₂ | CH₃ | CO₂CH₃ | Cl | CF₂CF₂CF₃ | 2 |
| CH(CH₃)₂ | CH₃ | CO₂CH₃ | CH₃ | CF₃ | 2 |
| CH(CH₃)₂ | CH₃ | CO₂CH₃ | CH₃ | CF₂CF₃ | 2 |
| CH(CH₃)₂ | CH₃ | CO₂CH₃ | CH₃ | CF₂CF₂CF₃ | 2 |

TABLE 12

| R² | R³ | R⁴ | R⁵ | R⁶ | m |
|---|---|---|---|---|---|
| CH(CH₃)₂ | CH₃ | CONH₂ | H | CF₃ | 2 |
| CH(CH₃)₂ | CH₃ | CONH₂ | H | CF₂CF₃ | 2 |
| CH(CH₃)₂ | CH₃ | CONH₂ | H | CF₂CF₂CF₃ | 2 |
| CH(CH₃)₂ | CH₃ | CONH₂ | F | CF₃ | 2 |
| CH(CH₃)₂ | CH₃ | CONH₂ | F | CF₂CF₃ | 2 |
| CH(CH₃)₂ | CH₃ | CONH₂ | F | CF₂CF₂CF₃ | 2 |
| CH(CH₃)₂ | CH₃ | CONH₂ | Cl | CF₃ | 2 |
| CH(CH₃)₂ | CH₃ | CONH₂ | Cl | CF₂CF₃ | 2 |
| CH(CH₃)₂ | CH₃ | CONH₂ | Cl | CF₂CF₂CF₃ | 2 |
| CH(CH₃)₂ | CH₃ | CONH₂ | CH₃ | CF₃ | 2 |
| CH(CH₃)₂ | CH₃ | CONH₂ | CH₃ | CF₂CF₃ | 2 |
| CH(CH₃)₂ | CH₃ | CONH₂ | CH₃ | CF₂CF₂CF₃ | 2 |
| CH(CH₃)₂ | CH₃ | C(S)NH₂ | H | CF₃ | 2 |
| CH(CH₃)₂ | CH₃ | C(S)NH₂ | H | CF₂CF₃ | 2 |
| CH(CH₃)₂ | CH₃ | C(S)NH₂ | H | CF₂CF₂CF₃ | 2 |
| CH(CH₃)₂ | CH₃ | C(S)NH₂ | F | CF₃ | 2 |
| CH(CH₃)₂ | CH₃ | C(S)NH₂ | F | CF₂CF₃ | 2 |
| CH(CH₃)₂ | CH₃ | C(S)NH₂ | F | CF₂CF₂CF₃ | 2 |
| CH(CH₃)₂ | CH₃ | C(S)NH₂ | Cl | CF₃ | 2 |
| CH(CH₃)₂ | CH₃ | C(S)NH₂ | Cl | CF₂CF₃ | 2 |
| CH(CH₃)₂ | CH₃ | C(S)NH₂ | Cl | CF₂CF₂CF₃ | 2 |
| CH(CH₃)₂ | CH₃ | C(S)NH₂ | CH₃ | CF₃ | 2 |
| CH(CH₃)₂ | CH₃ | C(S)NH₂ | CH₃ | CF₂CF₃ | 2 |
| CH(CH₃)₂ | CH₃ | C(S)NH₂ | CH₃ | CF₂CF₂CF₃ | 2 |

TABLE 13

| $R^2$ | $R^3$ | $R^4$ | $R^5$ | $R^6$ | m |
|---|---|---|---|---|---|
| $C(CH_3)_3$ | H | CN | H | $CF_3$ | 2 |
| $C(CH_3)_3$ | H | CN | H | $CF_2CF_3$ | 2 |
| $C(CH_3)_3$ | H | CN | H | $CF_2CF_2CF_3$ | 2 |
| $C(CH_3)_3$ | H | CN | F | $CF_3$ | 2 |
| $C(CH_3)_3$ | H | CN | F | $CF_2CF_3$ | 2 |
| $C(CH_3)_3$ | H | CN | F | $CF_2CF_2CF_3$ | 2 |
| $C(CH_3)_3$ | H | CN | Cl | $CF_3$ | 2 |
| $C(CH_3)_3$ | H | CN | Cl | $CF_2CF_3$ | 2 |
| $C(CH_3)_3$ | H | CN | Cl | $CF_2CF_2CF_3$ | 2 |
| $C(CH_3)_3$ | H | CN | $CH_3$ | $CF_3$ | 2 |
| $C(CH_3)_3$ | H | CN | $CH_3$ | $CF_2CF_3$ | 2 |
| $C(CH_3)_3$ | H | CN | $CH_3$ | $CF_2CF_2CF_3$ | 2 |
| $C(CH_3)_3$ | H | $CO_2CH_3$ | H | $CF_3$ | 2 |
| $C(CH_3)_3$ | H | $CO_2CH_3$ | H | $CF_2CF_3$ | 2 |
| $C(CH_3)_3$ | H | $CO_2CH_3$ | H | $CF_2CF_2CF_3$ | 2 |
| $C(CH_3)_3$ | H | $CO_2CH_3$ | F | $CF_3$ | 2 |
| $C(CH_3)_3$ | H | $CO_2CH_3$ | F | $CF_2CF_3$ | 2 |
| $C(CH_3)_3$ | H | $CO_2CH_3$ | F | $CF_2CF_2CF_3$ | 2 |
| $C(CH_3)_3$ | H | $CO_2CH_3$ | Cl | $CF_3$ | 2 |
| $C(CH_3)_3$ | H | $CO_2CH_3$ | Cl | $CF_2CF_3$ | 2 |
| $C(CH_3)_3$ | H | $CO_2CH_3$ | Cl | $CF_2CF_2CF_3$ | 2 |
| $C(CH_3)_3$ | H | $CO_2CH_3$ | $CH_3$ | $CF_3$ | 2 |
| $C(CH_3)_3$ | H | $CO_2CH_3$ | $CH_3$ | $CF_2CF_3$ | 2 |
| $C(CH_3)_3$ | H | $CO_2CH_3$ | $CH_3$ | $CF_2CF_2CF_3$ | 2 |

TABLE 14

| $R^2$ | $R^3$ | $R^4$ | $R^5$ | $R^6$ | m |
|---|---|---|---|---|---|
| $C(CH_3)_3$ | H | $CONH_2$ | H | $CF_3$ | 2 |
| $C(CH_3)_3$ | H | $CONH_2$ | H | $CF_2CF_3$ | 2 |
| $C(CH_3)_3$ | H | $CONH_2$ | H | $CF_2CF_2CF_3$ | 2 |
| $C(CH_3)_3$ | H | $CONH_2$ | F | $CF_3$ | 2 |
| $C(CH_3)_3$ | H | $CONH_2$ | F | $CF_2CF_3$ | 2 |
| $C(CH_3)_3$ | H | $CONH_2$ | F | $CF_2CF_2CF_3$ | 2 |
| $C(CH_3)_3$ | H | $CONH_2$ | Cl | $CF_3$ | 2 |
| $C(CH_3)_3$ | H | $CONH_2$ | Cl | $CF_2CF_3$ | 2 |
| $C(CH_3)_3$ | H | $CONH_2$ | Cl | $CF_2CF_2CF_3$ | 2 |
| $C(CH_3)_3$ | H | $CONH_2$ | $CH_3$ | $CF_3$ | 2 |
| $C(CH_3)_3$ | H | $CONH_2$ | $CH_3$ | $CF_2CF_3$ | 2 |
| $C(CH_3)_3$ | H | $CONH_2$ | $CH_3$ | $CF_2CF_2CF_3$ | 2 |
| $C(CH_3)_3$ | H | $C(S)NH_2$ | H | $CF_3$ | 2 |
| $C(CH_3)_3$ | H | $C(S)NH_2$ | H | $CF_2CF_3$ | 2 |
| $C(CH_3)_3$ | H | $C(S)NH_2$ | H | $CF_2CF_2CF_3$ | 2 |
| $C(CH_3)_3$ | H | $C(S)NH_2$ | F | $CF_3$ | 2 |
| $C(CH_3)_3$ | H | $C(S)NH_2$ | F | $CF_2CF_3$ | 2 |
| $C(CH_3)_3$ | H | $C(S)NH_2$ | F | $CF_2CF_2CF_3$ | 2 |
| $C(CH_3)_3$ | H | $C(S)NH_2$ | Cl | $CF_3$ | 2 |
| $C(CH_3)_3$ | H | $C(S)NH_2$ | Cl | $CF_2CF_3$ | 2 |
| $C(CH_3)_3$ | H | $C(S)NH_2$ | Cl | $CF_2CF_2CF_3$ | 2 |
| $C(CH_3)_3$ | H | $C(S)NH_2$ | $CH_3$ | $CF_3$ | 2 |
| $C(CH_3)_3$ | H | $C(S)NH_2$ | $CH_3$ | $CF_2CF_3$ | 2 |
| $C(CH_3)_3$ | H | $C(S)NH_2$ | $CH_3$ | $CF_2CF_2CF_3$ | 2 |

TABLE 15

| $R^2$ | $R^3$ | $R^4$ | $R^5$ | $R^6$ | m |
|---|---|---|---|---|---|
| $C(CH_3)_3$ | $CH_3$ | CN | H | $CF_3$ | 2 |
| $C(CH_3)_3$ | $CH_3$ | CN | H | $CF_2CF_3$ | 2 |
| $C(CH_3)_3$ | $CH_3$ | CN | H | $CF_2CF_2CF_3$ | 2 |
| $C(CH_3)_3$ | $CH_3$ | CN | F | $CF_3$ | 2 |
| $C(CH_3)_3$ | $CH_3$ | CN | F | $CF_2CF_3$ | 2 |
| $C(CH_3)_3$ | $CH_3$ | CN | F | $CF_2CF_2CF_3$ | 2 |
| $C(CH_3)_3$ | $CH_3$ | CN | Cl | $CF_3$ | 2 |
| $C(CH_3)_3$ | $CH_3$ | CN | Cl | $CF_2CF_3$ | 2 |
| $C(CH_3)_3$ | $CH_3$ | CN | Cl | $CF_2CF_2CF_3$ | 2 |
| $C(CH_3)_3$ | $CH_3$ | CN | $CH_3$ | $CF_3$ | 2 |
| $C(CH_3)_3$ | $CH_3$ | CN | $CH_3$ | $CF_2CF_3$ | 2 |
| $C(CH_3)_3$ | $CH_3$ | CN | $CH_3$ | $CF_2CF_2CF_3$ | 2 |
| $C(CH_3)_3$ | $CH_3$ | $CO_2CH_3$ | H | $CF_3$ | 2 |
| $C(CH_3)_3$ | $CH_3$ | $CO_2CH_3$ | H | $CF_2CF_3$ | 2 |
| $C(CH_3)_3$ | $CH_3$ | $CO_2CH_3$ | H | $CF_2CF_2CF_3$ | 2 |
| $C(CH_3)_3$ | $CH_3$ | $CO_2CH_3$ | F | $CF_3$ | 2 |
| $C(CH_3)_3$ | $CH_3$ | $CO_2CH_3$ | F | $CF_2CF_3$ | 2 |
| $C(CH_3)_3$ | $CH_3$ | $CO_2CH_3$ | F | $CF_2CF_2CF_3$ | 2 |
| $C(CH_3)_3$ | $CH_3$ | $CO_2CH_3$ | Cl | $CF_3$ | 2 |
| $C(CH_3)_3$ | $CH_3$ | $CO_2CH_3$ | Cl | $CF_2CF_3$ | 2 |
| $C(CH_3)_3$ | $CH_3$ | $CO_2CH_3$ | Cl | $CF_2CF_2CF_3$ | 2 |
| $C(CH_3)_3$ | $CH_3$ | $CO_2CH_3$ | $CH_3$ | $CF_3$ | 2 |
| $C(CH_3)_3$ | $CH_3$ | $CO_2CH_3$ | $CH_3$ | $CF_2CF_3$ | 2 |
| $C(CH_3)_3$ | $CH_3$ | $CO_2CH_3$ | $CH_3$ | $CF_2CF_2CF_3$ | 2 |

TABLE 16

| $R^2$ | $R^3$ | $R^4$ | $R^5$ | $R^6$ | m |
|---|---|---|---|---|---|
| $C(CH_3)_3$ | $CH_3$ | $CONH_2$ | H | $CF_3$ | 2 |
| $C(CH_3)_3$ | $CH_3$ | $CONH_2$ | H | $CF_2CF_3$ | 2 |
| $C(CH_3)_3$ | $CH_3$ | $CONH_2$ | H | $CF_2CF_2CF_3$ | 2 |
| $C(CH_3)_3$ | $CH_3$ | $CONH_2$ | F | $CF_3$ | 2 |
| $C(CH_3)_3$ | $CH_3$ | $CONH_2$ | F | $CF_2CF_3$ | 2 |
| $C(CH_3)_3$ | $CH_3$ | $CONH_2$ | F | $CF_2CF_2CF_3$ | 2 |
| $C(CH_3)_3$ | $CH_3$ | $CONH_2$ | Cl | $CF_3$ | 2 |
| $C(CH_3)_3$ | $CH_3$ | $CONH_2$ | Cl | $CF_2CF_3$ | 2 |
| $C(CH_3)_3$ | $CH_3$ | $CONH_2$ | Cl | $CF_2CF_2CF_3$ | 2 |
| $C(CH_3)_3$ | $CH_3$ | $CONH_2$ | $CH_3$ | $CF_3$ | 2 |
| $C(CH_3)_3$ | $CH_3$ | $CONH_2$ | $CH_3$ | $CF_2CF_3$ | 2 |
| $C(CH_3)_3$ | $CH_3$ | $CONH_2$ | $CH_3$ | $CF_2CF_2CF_3$ | 2 |
| $C(CH_3)_3$ | $CH_3$ | $C(S)NH_2$ | H | $CF_3$ | 2 |
| $C(CH_3)_3$ | $CH_3$ | $C(S)NH_2$ | H | $CF_2CF_3$ | 2 |
| $C(CH_3)_3$ | $CH_3$ | $C(S)NH_2$ | H | $CF_2CF_2CF_3$ | 2 |
| $C(CH_3)_3$ | $CH_3$ | $C(S)NH_2$ | F | $CF_3$ | 2 |
| $C(CH_3)_3$ | $CH_3$ | $C(S)NH_2$ | F | $CF_2CF_3$ | 2 |
| $C(CH_3)_3$ | $CH_3$ | $C(S)NH_2$ | F | $CF_2CF_2CF_3$ | 2 |
| $C(CH_3)_3$ | $CH_3$ | $C(S)NH_2$ | Cl | $CF_3$ | 2 |
| $C(CH_3)_3$ | $CH_3$ | $C(S)NH_2$ | Cl | $CF_2CF_3$ | 2 |
| $C(CH_3)_3$ | $CH_3$ | $C(S)NH_2$ | Cl | $CF_2CF_2CF_3$ | 2 |
| $C(CH_3)_3$ | $CH_3$ | $C(S)NH_2$ | $CH_3$ | $CF_3$ | 2 |
| $C(CH_3)_3$ | $CH_3$ | $C(S)NH_2$ | $CH_3$ | $CF_2CF_3$ | 2 |
| $C(CH_3)_3$ | $CH_3$ | $C(S)NH_2$ | $CH_3$ | $CF_2CF_2CF_3$ | 2 |

TABLE 17

| $R^2$ | $R^3$ | $R^4$ | $R^5$ | $R^6$ | m |
|---|---|---|---|---|---|
| $OCH_3$ | H | CN | H | $CF_3$ | 2 |
| $OCH_3$ | H | CN | H | $CF_2CF_3$ | 2 |
| $OCH_3$ | H | CN | H | $CF_2CF_2CF_3$ | 2 |
| $OCH_3$ | H | CN | F | $CF_3$ | 2 |
| $OCH_3$ | H | CN | F | $CF_2CF_3$ | 2 |
| $OCH_3$ | H | CN | F | $CF_2CF_2CF_3$ | 2 |
| $OCH_3$ | H | CN | Cl | $CF_3$ | 2 |
| $OCH_3$ | H | CN | Cl | $CF_2CF_3$ | 2 |
| $OCH_3$ | H | CN | Cl | $CF_2CF_2CF_3$ | 2 |
| $OCH_3$ | H | CN | $CH_3$ | $CF_3$ | 2 |
| $OCH_3$ | H | CN | $CH_3$ | $CF_2CF_3$ | 2 |
| $OCH_3$ | H | CN | $CH_3$ | $CF_2CF_2CF_3$ | 2 |
| $OCH_3$ | H | $CO_2CH_3$ | H | $CF_3$ | 2 |
| $OCH_3$ | H | $CO_2CH_3$ | H | $CF_2CF_3$ | 2 |
| $OCH_3$ | H | $CO_2CH_3$ | H | $CF_2CF_2CF_3$ | 2 |
| $OCH_3$ | H | $CO_2CH_3$ | F | $CF_3$ | 2 |
| $OCH_3$ | H | $CO_2CH_3$ | F | $CF_2CF_3$ | 2 |
| $OCH_3$ | H | $CO_2CH_3$ | F | $CF_2CF_2CF_3$ | 2 |
| $OCH_3$ | H | $CO_2CH_3$ | Cl | $CF_3$ | 2 |
| $OCH_3$ | H | $CO_2CH_3$ | Cl | $CF_2CF_3$ | 2 |
| $OCH_3$ | H | $CO_2CH_3$ | Cl | $CF_2CF_2CF_3$ | 2 |
| $OCH_3$ | H | $CO_2CH_3$ | $CH_3$ | $CF_3$ | 2 |
| $OCH_3$ | H | $CO_2CH_3$ | $CH_3$ | $CF_2CF_3$ | 2 |
| $OCH_3$ | H | $CO_2CH_3$ | $CH_3$ | $CF_2CF_2CF_3$ | 2 |

TABLE 18

| R² | R³ | R⁴ | R⁵ | R⁶ | m |
|---|---|---|---|---|---|
| OCH₃ | H | CONH₂ | H | CF₃ | 2 |
| OCH₃ | H | CONH₂ | H | CF₂CF₃ | 2 |
| OCH₃ | H | CONH₂ | H | CF₂CF₂CF₃ | 2 |
| OCH₃ | H | CONH₂ | F | CF₃ | 2 |
| OCH₃ | H | CONH₂ | F | CF₂CF₃ | 2 |
| OCH₃ | H | CONH₂ | F | CF₂CF₂CF₃ | 2 |
| OCH₃ | H | CONH₂ | Cl | CF₃ | 2 |
| OCH₃ | H | CONH₂ | Cl | CF₂CF₃ | 2 |
| OCH₃ | H | CONH₂ | Cl | CF₂CF₂CF₃ | 2 |
| OCH₃ | H | CONH₂ | CH₃ | CF₃ | 2 |
| OCH₃ | H | CONH₂ | CH₃ | CF₂CF₃ | 2 |
| OCH₃ | H | CONH₂ | CH₃ | CF₂CF₂CF₃ | 2 |
| OCH₃ | H | C(S)NH₂ | H | CF₃ | 2 |
| OCH₃ | H | C(S)NH₂ | H | CF₂CF₃ | 2 |
| OCH₃ | H | C(S)NH₂ | H | CF₂CF₂CF₃ | 2 |
| OCH₃ | H | C(S)NH₂ | F | CF₃ | 2 |
| OCH₃ | H | C(S)NH₂ | F | CF₂CF₃ | 2 |
| OCH₃ | H | C(S)NH₂ | F | CF₂CF₂CF₃ | 2 |
| OCH₃ | H | C(S)NH₂ | Cl | CF₃ | 2 |
| OCH₃ | H | C(S)NH₂ | Cl | CF₂CF₃ | 2 |
| OCH₃ | H | C(S)NH₂ | Cl | CF₂CF₂CF₃ | 2 |
| OCH₃ | H | C(S)NH₂ | CH₃ | CF₃ | 2 |
| OCH₃ | H | C(S)NH₂ | CH₃ | CF₂CF₃ | 2 |
| OCH₃ | H | C(S)NH₂ | CH₃ | CF₂CF₂CF₃ | 2 |

TABLE 19

| R² | R³ | R⁴ | R⁵ | R⁶ | m |
|---|---|---|---|---|---|
| OCH₃ | CH₃ | CN | H | CF₃ | 2 |
| OCH₃ | CH₃ | CN | H | CF₂CF₃ | 2 |
| OCH₃ | CH₃ | CN | H | CF₂CF₂CF₃ | 2 |
| OCH₃ | CH₃ | CN | F | CF₃ | 2 |
| OCH₃ | CH₃ | CN | F | CF₂CF₃ | 2 |
| OCH₃ | CH₃ | CN | F | CF₂CF₂CF₃ | 2 |
| OCH₃ | CH₃ | CN | Cl | CF₃ | 2 |
| OCH₃ | CH₃ | CN | Cl | CF₂CF₃ | 2 |
| OCH₃ | CH₃ | CN | Cl | CF₂CF₂CF₃ | 2 |
| OCH₃ | CH₃ | CN | CH₃ | CF₃ | 2 |
| OCH₃ | CH₃ | CN | CH₃ | CF₂CF₃ | 2 |
| OCH₃ | CH₃ | CN | CH₃ | CF₂CF₂CF₃ | 2 |
| OCH₃ | CH₃ | CO₂CH₃ | H | CF₃ | 2 |
| OCH₃ | CH₃ | CO₂CH₃ | H | CF₂CF₃ | 2 |
| OCH₃ | CH₃ | CO₂CH₃ | H | CF₂CF₂CF₃ | 2 |
| OCH₃ | CH₃ | CO₂CH₃ | F | CF₃ | 2 |
| OCH₃ | CH₃ | CO₂CH₃ | F | CF₂CF₃ | 2 |
| OCH₃ | CH₃ | CO₂CH₃ | F | CF₂CF₂CF₃ | 2 |
| OCH₃ | CH₃ | CO₂CH₃ | Cl | CF₃ | 2 |
| OCH₃ | CH₃ | CO₂CH₃ | Cl | CF₂CF₃ | 2 |
| OCH₃ | CH₃ | CO₂CH₃ | Cl | CF₂CF₂CF₃ | 2 |
| OCH₃ | CH₃ | CO₂CH₃ | CH₃ | CF₃ | 2 |
| OCH₃ | CH₃ | CO₂CH₃ | CH₃ | CF₂CF₃ | 2 |
| OCH₃ | CH₃ | CO₂CH₃ | CH₃ | CF₂CF₂CF₃ | 2 |

TABLE 20

| R² | R³ | R⁴ | R⁵ | R⁶ | m |
|---|---|---|---|---|---|
| OCH₃ | CH₃ | CONH₂ | H | CF₃ | 2 |
| OCH₃ | CH₃ | CONH₂ | H | CF₂CF₃ | 2 |
| OCH₃ | CH₃ | CONH₂ | H | CF₂CF₂CF₃ | 2 |
| OCH₃ | CH₃ | CONH₂ | F | CF₃ | 2 |
| OCH₃ | CH₃ | CONH₂ | F | CF₂CF₃ | 2 |
| OCH₃ | CH₃ | CONH₂ | F | CF₂CF₂CF₃ | 2 |
| OCH₃ | CH₃ | CONH₂ | Cl | CF₃ | 2 |
| OCH₃ | CH₃ | CONH₂ | Cl | CF₂CF₃ | 2 |
| OCH₃ | CH₃ | CONH₂ | Cl | CF₂CF₂CF₃ | 2 |
| OCH₃ | CH₃ | CONH₂ | CH₃ | CF₃ | 2 |
| OCH₃ | CH₃ | CONH₂ | CH₃ | CF₂CF₃ | 2 |
| OCH₃ | CH₃ | CONH₂ | CH₃ | CF₂CF₂CF₃ | 2 |
| OCH₃ | CH₃ | C(S)NH₂ | H | CF₃ | 2 |
| OCH₃ | CH₃ | C(S)NH₂ | H | CF₂CF₃ | 2 |
| OCH₃ | CH₃ | C(S)NH₂ | H | CF₂CF₂CF₃ | 2 |
| OCH₃ | CH₃ | C(S)NH₂ | F | CF₃ | 2 |
| OCH₃ | CH₃ | C(S)NH₂ | F | CF₂CF₃ | 2 |
| OCH₃ | CH₃ | C(S)NH₂ | F | CF₂CF₂CF₃ | 2 |
| OCH₃ | CH₃ | C(S)NH₂ | Cl | CF₃ | 2 |
| OCH₃ | CH₃ | C(S)NH₂ | Cl | CF₂CF₃ | 2 |
| OCH₃ | CH₃ | C(S)NH₂ | Cl | CF₂CF₂CF₃ | 2 |
| OCH₃ | CH₃ | C(S)NH₂ | CH₃ | CF₃ | 2 |
| OCH₃ | CH₃ | C(S)NH₂ | CH₃ | CF₂CF₃ | 2 |
| OCH₃ | CH₃ | C(S)NH₂ | CH₃ | CF₂CF₂CF₃ | 2 |

TABLE 21

| R² | R³ | R⁴ | R⁵ | R⁶ | m |
|---|---|---|---|---|---|
| SCH₃ | H | CN | H | CF₃ | 2 |
| SCH₃ | H | CN | H | CF₂CF₃ | 2 |
| SCH₃ | H | CN | H | CF₂CF₂CF₃ | 2 |
| SCH₃ | H | CN | F | CF₃ | 2 |
| SCH₃ | H | CN | F | CF₂CF₃ | 2 |
| SCH₃ | H | CN | F | CF₂CF₂CF₃ | 2 |
| SCH₃ | H | CN | Cl | CF₃ | 2 |
| SCH₃ | H | CN | Cl | CF₂CF₃ | 2 |
| SCH₃ | H | CN | Cl | CF₂CF₂CF₃ | 2 |
| SCH₃ | H | CN | CH₃ | CF₃ | 2 |
| SCH₃ | H | CN | CH₃ | CF₂CF₃ | 2 |
| SCH₃ | H | CN | CH₃ | CF₂CF₂CF₃ | 2 |
| SCH₃ | H | CO₂CH₃ | H | CF₃ | 2 |
| SCH₃ | H | CO₂CH₃ | H | CF₂CF₃ | 2 |
| SCH₃ | H | CO₂CH₃ | H | CF₂CF₂CF₃ | 2 |
| SCH₃ | H | CO₂CH₃ | F | CF₃ | 2 |
| SCH₃ | H | CO₂CH₃ | F | CF₂CF₃ | 2 |
| SCH₃ | H | CO₂CH₃ | F | CF₂CF₂CF₃ | 2 |
| SCH₃ | H | CO₂CH₃ | Cl | CF₃ | 2 |
| SCH₃ | H | CO₂CH₃ | Cl | CF₂CF₃ | 2 |
| SCH₃ | H | CO₂CH₃ | Cl | CF₂CF₂CF₃ | 2 |
| SCH₃ | H | CO₂CH₃ | CH₃ | CF₃ | 2 |
| SCH₃ | H | CO₂CH₃ | CH₃ | CF₂CF₃ | 2 |
| SCH₃ | H | CO₂CH₃ | CH₃ | CF₂CF₂CF₃ | 2 |

TABLE 22

| R² | R³ | R⁴ | R⁵ | R⁶ | m |
|---|---|---|---|---|---|
| SCH₃ | H | CONH₂ | H | CF₃ | 2 |
| SCH₃ | H | CONH₂ | H | CF₂CF₃ | 2 |
| SCH₃ | H | CONH₂ | H | CF₂CF₂CF₃ | 2 |
| SCH₃ | H | CONH₂ | F | CF₃ | 2 |
| SCH₃ | H | CONH₂ | F | CF₂CF₃ | 2 |
| SCH₃ | H | CONH₂ | F | CF₂CF₂CF₃ | 2 |
| SCH₃ | H | CONH₂ | Cl | CF₃ | 2 |
| SCH₃ | H | CONH₂ | Cl | CF₂CF₃ | 2 |
| SCH₃ | H | CONH₂ | Cl | CF₂CF₂CF₃ | 2 |
| SCH₃ | H | CONH₂ | CH₃ | CF₃ | 2 |
| SCH₃ | H | CONH₂ | CH₃ | CF₂CF₃ | 2 |
| SCH₃ | H | CONH₂ | CH₃ | CF₂CF₂CF₃ | 2 |
| SCH₃ | H | C(S)NH₂ | H | CF₃ | 2 |
| SCH₃ | H | C(S)NH₂ | H | CF₂CF₃ | 2 |
| SCH₃ | H | C(S)NH₂ | H | CF₂CF₂CF₃ | 2 |
| SCH₃ | H | C(S)NH₂ | F | CF₃ | 2 |
| SCH₃ | H | C(S)NH₂ | F | CF₂CF₃ | 2 |
| SCH₃ | H | C(S)NH₂ | F | CF₂CF₂CF₃ | 2 |
| SCH₃ | H | C(S)NH₂ | Cl | CF₃ | 2 |
| SCH₃ | H | C(S)NH₂ | Cl | CF₂CF₃ | 2 |
| SCH₃ | H | C(S)NH₂ | Cl | CF₂CF₂CF₃ | 2 |
| SCH₃ | H | C(S)NH₂ | CH₃ | CF₃ | 2 |
| SCH₃ | H | C(S)NH₂ | CH₃ | CF₂CF₃ | 2 |
| SCH₃ | H | C(S)NH₂ | CH₃ | CF₂CF₂CF₃ | 2 |

TABLE 23

| $R^2$ | $R^3$ | $R^4$ | $R^5$ | $R^6$ | m |
|---|---|---|---|---|---|
| $SCH_3$ | $CH_3$ | CN | H | $CF_3$ | 2 |
| $SCH_3$ | $CH_3$ | CN | H | $CF_2CF_3$ | 2 |
| $SCH_3$ | $CH_3$ | CN | H | $CF_2CF_2CF_3$ | 2 |
| $SCH_3$ | $CH_3$ | CN | F | $CF_3$ | 2 |
| $SCH_3$ | $CH_3$ | CN | F | $CF_2CF_3$ | 2 |
| $SCH_3$ | $CH_3$ | CN | F | $CF_2CF_2CF_3$ | 2 |
| $SCH_3$ | $CH_3$ | CN | Cl | $CF_3$ | 2 |
| $SCH_3$ | $CH_3$ | CN | Cl | $CF_2CF_3$ | 2 |
| $SCH_3$ | $CH_3$ | CN | Cl | $CF_2CF_2CF_3$ | 2 |
| $SCH_3$ | $CH_3$ | CN | $CH_3$ | $CF_3$ | 2 |
| $SCH_3$ | $CH_3$ | CN | $CH_3$ | $CF_2CF_3$ | 2 |
| $SCH_3$ | $CH_3$ | CN | $CH_3$ | $CF_2CF_2CF_3$ | 2 |
| $SCH_3$ | $CH_3$ | $CO_2CH_3$ | H | $CF_3$ | 2 |
| $SCH_3$ | $CH_3$ | $CO_2CH_3$ | H | $CF_2CF_3$ | 2 |
| $SCH_3$ | $CH_3$ | $CO_2CH_3$ | H | $CF_2CF_2CF_3$ | 2 |
| $SCH_3$ | $CH_3$ | $CO_2CH_3$ | F | $CF_3$ | 2 |
| $SCH_3$ | $CH_3$ | $CO_2CH_3$ | F | $CF_2CF_3$ | 2 |
| $SCH_3$ | $CH_3$ | $CO_2CH_3$ | F | $CF_2CF_2CF_3$ | 2 |
| $SCH_3$ | $CH_3$ | $CO_2CH_3$ | Cl | $CF_3$ | 2 |
| $SCH_3$ | $CH_3$ | $CO_2CH_3$ | Cl | $CF_2CF_3$ | 2 |
| $SCH_3$ | $CH_3$ | $CO_2CH_3$ | Cl | $CF_2CF_2CF_3$ | 2 |
| $SCH_3$ | $CH_3$ | $CO_2CH_3$ | $CH_3$ | $CF_3$ | 2 |
| $SCH_3$ | $CH_3$ | $CO_2CH_3$ | $CH_3$ | $CF_2CF_3$ | 2 |
| $SCH_3$ | $CH_3$ | $CO_2CH_3$ | $CH_3$ | $CF_2CF_2CF_3$ | 2 |

TABLE 24

| $R^2$ | $R^3$ | $R^4$ | $R^5$ | $R^6$ | m |
|---|---|---|---|---|---|
| $SCH_3$ | $CH_3$ | $CONH_2$ | H | $CF_3$ | 2 |
| $SCH_3$ | $CH_3$ | $CONH_2$ | H | $CF_2CF_3$ | 2 |
| $SCH_3$ | $CH_3$ | $CONH_2$ | H | $CF_2CF_2CF_3$ | 2 |
| $SCH_3$ | $CH_3$ | $CONH_2$ | F | $CF_3$ | 2 |
| $SCH_3$ | $CH_3$ | $CONH_2$ | F | $CF_2CF_3$ | 2 |
| $SCH_3$ | $CH_3$ | $CONH_2$ | F | $CF_2CF_2CF_3$ | 2 |
| $SCH_3$ | $CH_3$ | $CONH_2$ | Cl | $CF_3$ | 2 |
| $SCH_3$ | $CH_3$ | $CONH_2$ | Cl | $CF_2CF_3$ | 2 |
| $SCH_3$ | $CH_3$ | $CONH_2$ | Cl | $CF_2CF_2CF_3$ | 2 |
| $SCH_3$ | $CH_3$ | $CONH_2$ | $CH_3$ | $CF_3$ | 2 |
| $SCH_3$ | $CH_3$ | $CONH_2$ | $CH_3$ | $CF_2CF_3$ | 2 |
| $SCH_3$ | $CH_3$ | $CONH_2$ | $CH_3$ | $CF_2CF_2CF_3$ | 2 |
| $SCH_3$ | $CH_3$ | $C(S)NH_2$ | H | $CF_3$ | 2 |
| $SCH_3$ | $CH_3$ | $C(S)NH_2$ | H | $CF_2CF_3$ | 2 |
| $SCH_3$ | $CH_3$ | $C(S)NH_2$ | H | $CF_2CF_2CF_3$ | 2 |
| $SCH_3$ | $CH_3$ | $C(S)NH_2$ | F | $CF_3$ | 2 |
| $SCH_3$ | $CH_3$ | $C(S)NH_2$ | F | $CF_2CF_3$ | 2 |
| $SCH_3$ | $CH_3$ | $C(S)NH_2$ | F | $CF_2CF_2CF_3$ | 2 |
| $SCH_3$ | $CH_3$ | $C(S)NH_2$ | Cl | $CF_3$ | 2 |
| $SCH_3$ | $CH_3$ | $C(S)NH_2$ | Cl | $CF_2CF_3$ | 2 |
| $SCH_3$ | $CH_3$ | $C(S)NH_2$ | Cl | $CF_2CF_2CF_3$ | 2 |
| $SCH_3$ | $CH_3$ | $C(S)NH_2$ | $CH_3$ | $CF_3$ | 2 |
| $SCH_3$ | $CH_3$ | $C(S)NH_2$ | $CH_3$ | $CF_2CF_3$ | 2 |
| $SCH_3$ | $CH_3$ | $C(S)NH_2$ | $CH_3$ | $CF_2CF_2CF_3$ | 2 |

TABLE 25

| $R^2$ | $R^3$ | $R^4$ | $R^5$ | $R^6$ | m |
|---|---|---|---|---|---|
| $CH_2CH_2CH_3$ | H | CN | H | $CF_3$ | 2 |
| $CH_2CH_2CH_3$ | H | CN | H | $CF_2CF_3$ | 2 |
| $CH_2CH_2CH_3$ | H | CN | H | $CF_2CF_2CF_3$ | 2 |
| $CH_2CH_2CH_3$ | H | CN | F | $CF_3$ | 2 |
| $CH_2CH_2CH_3$ | H | CN | F | $CF_2CF_3$ | 2 |
| $CH_2CH_2CH_3$ | H | CN | F | $CF_2CF_2CF_3$ | 2 |
| $CH_2CH_2CH_3$ | H | CN | Cl | $CF_3$ | 2 |
| $CH_2CH_2CH_3$ | H | CN | Cl | $CF_2CF_3$ | 2 |
| $CH_2CH_2CH_3$ | H | CN | Cl | $CF_2CF_2CF_3$ | 2 |
| $CH_2CH_2CH_3$ | H | CN | $CH_3$ | $CF_3$ | 2 |
| $CH_2CH_2CH_3$ | H | CN | $CH_3$ | $CF_2CF_3$ | 2 |
| $CH_2CH_2CH_3$ | H | CN | $CH_3$ | $CF_2CF_2CF_3$ | 2 |
| $CH_2CH_2CH_3$ | H | $CO_2CH_3$ | H | $CF_3$ | 2 |
| $CH_2CH_2CH_3$ | H | $CO_2CH_3$ | H | $CF_2CF_3$ | 2 |
| $CH_2CH_2CH_3$ | H | $CO_2CH_3$ | H | $CF_2CF_2CF_3$ | 2 |
| $CH_2CH_2CH_3$ | H | $CO_2CH_3$ | F | $CF_3$ | 2 |
| $CH_2CH_2CH_3$ | H | $CO_2CH_3$ | F | $CF_2CF_3$ | 2 |
| $CH_2CH_2CH_3$ | H | $CO_2CH_3$ | F | $CF_2CF_2CF_3$ | 2 |
| $CH_2CH_2CH_3$ | H | $CO_2CH_3$ | Cl | $CF_3$ | 2 |
| $CH_2CH_2CH_3$ | H | $CO_2CH_3$ | Cl | $CF_2CF_3$ | 2 |
| $CH_2CH_2CH_3$ | H | $CO_2CH_3$ | Cl | $CF_2CF_2CF_3$ | 2 |
| $CH_2CH_2CH_3$ | H | $CO_2CH_3$ | $CH_3$ | $CF_3$ | 2 |
| $CH_2CH_2CH_3$ | H | $CO_2CH_3$ | $CH_3$ | $CF_2CF_3$ | 2 |
| $CH_2CH_2CH_3$ | H | $CO_2CH_3$ | $CH_3$ | $CF_2CF_2CF_3$ | 2 |

TABLE 26

| $R^2$ | $R^3$ | $R^4$ | $R^5$ | $R^6$ | m |
|---|---|---|---|---|---|
| $CH_2CH_2CH_3$ | H | $CONH_2$ | H | $CF_3$ | 2 |
| $CH_2CH_2CH_3$ | H | $CONH_2$ | H | $CF_2CF_3$ | 2 |
| $CH_2CH_2CH_3$ | H | $CONH_2$ | H | $CF_2CF_2CF_3$ | 2 |
| $CH_2CH_2CH_3$ | H | $CONH_2$ | F | $CF_3$ | 2 |
| $CH_2CH_2CH_3$ | H | $CONH_2$ | F | $CF_2CF_3$ | 2 |
| $CH_2CH_2CH_3$ | H | $CONH_2$ | F | $CF_2CF_2CF_3$ | 2 |
| $CH_2CH_2CH_3$ | H | $CONH_2$ | Cl | $CF_3$ | 2 |
| $CH_2CH_2CH_3$ | H | $CONH_2$ | Cl | $CF_2CF_3$ | 2 |
| $CH_2CH_2CH_3$ | H | $CONH_2$ | Cl | $CF_2CF_2CF_3$ | 2 |
| $CH_2CH_2CH_3$ | H | $CONH_2$ | $CH_3$ | $CF_3$ | 2 |
| $CH_2CH_2CH_3$ | H | $CONH_2$ | $CH_3$ | $CF_2CF_3$ | 2 |
| $CH_2CH_2CH_3$ | H | $CONH_2$ | $CH_3$ | $CF_2CF_2CF_3$ | 2 |
| $CH_2CH_2CH_3$ | H | $C(S)NH_2$ | H | $CF_3$ | 2 |
| $CH_2CH_2CH_3$ | H | $C(S)NH_2$ | H | $CF_2CF_3$ | 2 |
| $CH_2CH_2CH_3$ | H | $C(S)NH_2$ | F | $CF_3$ | 2 |
| $CH_2CH_2CH_3$ | H | $C(S)NH_2$ | F | $CF_2CF_3$ | 2 |
| $CH_2CH_2CH_3$ | H | $C(S)NH_2$ | Cl | $CF_3$ | 2 |
| $CH_2CH_2CH_3$ | H | $C(S)NH_2$ | Cl | $CF_2CF_3$ | 2 |
| $CH_2CH_2CH_3$ | H | $C(S)NH_2$ | Cl | $CF_2CF_2CF_3$ | 2 |
| $CH_2CH_2CH_3$ | H | $C(S)NH_2$ | $CH_3$ | $CF_3$ | 2 |
| $CH_2CH_2CH_3$ | H | $C(S)NH_2$ | $CH_3$ | $CF_2CF_3$ | 2 |
| $CH_2CH_2CH_3$ | H | $C(S)NH_2$ | $CH_3$ | $CF_2CF_2CF_3$ | 2 |

TABLE 27

| $R^2$ | $R^3$ | $R^4$ | $R^5$ | $R^6$ | m |
|---|---|---|---|---|---|
| $CH_2CH_2CH_3$ | $CH_3$ | CN | H | $CF_3$ | 2 |
| $CH_2CH_2CH_3$ | $CH_3$ | CN | H | $CF_2CF_3$ | 2 |
| $CH_2CH_2CH_3$ | $CH_3$ | CN | H | $CF_2CF_2CF_3$ | 2 |
| $CH_2CH_2CH_3$ | $CH_3$ | CN | F | $CF_3$ | 2 |
| $CH_2CH_2CH_3$ | $CH_3$ | CN | F | $CF_2CF_3$ | 2 |
| $CH_2CH_2CH_3$ | $CH_3$ | CN | F | $CF_2CF_2CF_3$ | 2 |
| $CH_2CH_2CH_3$ | $CH_3$ | CN | Cl | $CF_3$ | 2 |
| $CH_2CH_2CH_3$ | $CH_3$ | CN | Cl | $CF_2CF_3$ | 2 |
| $CH_2CH_2CH_3$ | $CH_3$ | CN | Cl | $CF_2CF_2CF_3$ | 2 |
| $CH_2CH_2CH_3$ | $CH_3$ | CN | $CH_3$ | $CF_3$ | 2 |
| $CH_2CH_2CH_3$ | $CH_3$ | CN | $CH_3$ | $CF_2CF_3$ | 2 |
| $CH_2CH_2CH_3$ | $CH_3$ | CN | $CH_3$ | $CF_2CF_2CF_3$ | 2 |
| $CH_2CH_2CH_3$ | $CH_3$ | $CO_2CH_3$ | H | $CF_3$ | 2 |
| $CH_2CH_2CH_3$ | $CH_3$ | $CO_2CH_3$ | H | $CF_2CF_3$ | 2 |
| $CH_2CH_2CH_3$ | $CH_3$ | $CO_2CH_3$ | H | $CF_2CF_2CF_3$ | 2 |
| $CH_2CH_2CH_3$ | $CH_3$ | $CO_2CH_3$ | F | $CF_3$ | 2 |
| $CH_2CH_2CH_3$ | $CH_3$ | $CO_2CH_3$ | F | $CF_2CF_3$ | 2 |
| $CH_2CH_2CH_3$ | $CH_3$ | $CO_2CH_3$ | F | $CF_2CF_2CF_3$ | 2 |
| $CH_2CH_2CH_3$ | $CH_3$ | $CO_2CH_3$ | Cl | $CF_3$ | 2 |
| $CH_2CH_2CH_3$ | $CH_3$ | $CO_2CH_3$ | Cl | $CF_2CF_3$ | 2 |
| $CH_2CH_2CH_3$ | $CH_3$ | $CO_2CH_3$ | Cl | $CF_2CF_2CF_3$ | 2 |
| $CH_2CH_2CH_3$ | $CH_3$ | $CO_2CH_3$ | $CH_3$ | $CF_3$ | 2 |
| $CH_2CH_2CH_3$ | $CH_3$ | $CO_2CH_3$ | $CH_3$ | $CF_2CF_3$ | 2 |
| $CH_2CH_2CH_3$ | $CH_3$ | $CO_2CH_3$ | $CH_3$ | $CF_2CF_2CF_3$ | 2 |

TABLE 28

| R² | R³ | R⁴ | R⁵ | R⁶ | m |
|---|---|---|---|---|---|
| CH₂CH₂CH₃ | CH₃ | CONH₂ | H | CF₃ | 2 |
| CH₂CH₂CH₃ | CH₃ | CONH₂ | H | CF₂CF₃ | 2 |
| CH₂CH₂CH₃ | CH₃ | CONH₂ | H | CF₂CF₂CF₃ | 2 |
| CH₂CH₂CH₃ | CH₃ | CONH₂ | F | CF₃ | 2 |
| CH₂CH₂CH₃ | CH₃ | CONH₂ | F | CF₂CF₃ | 2 |
| CH₂CH₂CH₃ | CH₃ | CONH₂ | F | CF₂CF₂CF₃ | 2 |
| CH₂CH₂CH₃ | CH₃ | CONH₂ | Cl | CF₃ | 2 |
| CH₂CH₂CH₃ | CH₃ | CONH₂ | Cl | CF₂CF₃ | 2 |
| CH₂CH₂CH₃ | CH₃ | CONH₂ | Cl | CF₂CF₂CF₃ | 2 |
| CH₂CH₂CH₃ | CH₃ | CONH₂ | CH₃ | CF₃ | 2 |
| CH₂CH₂CH₃ | CH₃ | CONH₂ | CH₃ | CF₂CF₃ | 2 |
| CH₂CH₂CH₃ | CH₃ | CONH₂ | CH₃ | CF₂CF₂CF₃ | 2 |
| CH₂CH₂CH₃ | CH₃ | C(S)NH₂ | H | CF₃ | 2 |
| CH₂CH₂CH₃ | CH₃ | C(S)NH₂ | H | CF₂CF₃ | 2 |
| CH₂CH₂CH₃ | CH₃ | C(S)NH₂ | H | CF₂CF₂CF₃ | 2 |
| CH₂CH₂CH₃ | CH₃ | C(S)NH₂ | F | CF₃ | 2 |
| CH₂CH₂CH₃ | CH₃ | C(S)NH₂ | F | CF₂CF₃ | 2 |
| CH₂CH₂CH₃ | CH₃ | C(S)NH₂ | F | CF₂CF₂CF₃ | 2 |
| CH₂CH₂CH₃ | CH₃ | C(S)NH₂ | Cl | CF₃ | 2 |
| CH₂CH₂CH₃ | CH₃ | C(S)NH₂ | Cl | CF₂CF₃ | 2 |
| CH₂CH₂CH₃ | CH₃ | C(S)NH₂ | Cl | CF₂CF₂CF₃ | 2 |
| CH₂CH₂CH₃ | CH₃ | C(S)NH₂ | CH₃ | CF₃ | 2 |
| CH₂CH₂CH₃ | CH₃ | C(S)NH₂ | CH₃ | CF₂CF₃ | 2 |
| CH₂CH₂CH₃ | CH₃ | C(S)NH₂ | CH₃ | CF₂CF₂CF₃ | 2 |

TABLE 29

| R² | R³ | R⁴ | R⁵ | R⁶ | m |
|---|---|---|---|---|---|
| CH₃ | H | CO₂CH₂CH₃ | H | CF₃ | 2 |
| CH₃ | H | CO₂CH₂CH₃ | F | CF₃ | 2 |
| CH₃ | H | CO₂CH₂CH₃ | Cl | CF₃ | 2 |
| CH₃ | H | CO₂CH₂CH₃ | CH₃ | CF₃ | 2 |
| CH₃ | CH₃ | CO₂CH₂CH₃ | H | CF₃ | 2 |
| CH₃ | CH₃ | CO₂CH₂CH₃ | F | CF₃ | 2 |
| CH₃ | CH₃ | CO₂CH₂CH₃ | Cl | CF₃ | 2 |
| CH₃ | CH₃ | CO₂CH₂CH₃ | CH₃ | CF₃ | 2 |
| CH₂CH₃ | H | CO₂CH₂CH₃ | H | CF₃ | 2 |
| CH₂CH₃ | H | CO₂CH₂CH₃ | F | CF₃ | 2 |
| CH₂CH₃ | H | CO₂CH₂CH₃ | Cl | CF₃ | 2 |
| CH₂CH₃ | H | CO₂CH₂CH₃ | CH₃ | CF₃ | 2 |
| CH₂CH₃ | CH₃ | CO₂CH₂CH₃ | H | CF₃ | 2 |
| CH₂CH₃ | CH₃ | CO₂CH₂CH₃ | F | CF₃ | 2 |
| CH₂CH₃ | CH₃ | CO₂CH₂CH₃ | Cl | CF₃ | 2 |
| CH₂CH₃ | CH₃ | CO₂CH₂CH₃ | CH₃ | CF₃ | 2 |
| CH(CH₃)₂ | H | CO₂CH₂CH₃ | H | CF₃ | 2 |
| CH(CH₃)₂ | H | CO₂CH₂CH₃ | F | CF₃ | 2 |
| CH(CH₃)₂ | H | CO₂CH₂CH₃ | Cl | CF₃ | 2 |
| CH(CH₃)₂ | H | CO₂CH₂CH₃ | CH₃ | CF₃ | 2 |
| CH(CH₃)₂ | CH₃ | CO₂CH₂CH₃ | H | CF₃ | 2 |
| CH(CH₃)₂ | CH₃ | CO₂CH₂CH₃ | F | CF₃ | 2 |
| CH(CH₃)₂ | CH₃ | CO₂CH₂CH₃ | Cl | CF₃ | 2 |
| CH(CH₃)₂ | CH₃ | CO₂CH₂CH₃ | CH₃ | CF₃ | 2 |
| C(CH₃)₃ | H | CO₂CH₂CH₃ | H | CF₃ | 2 |
| C(CH₃)₃ | H | CO₂CH₂CH₃ | F | CF₃ | 2 |
| C(CH₃)₃ | H | CO₂CH₂CH₃ | Cl | CF₃ | 2 |
| C(CH₃)₃ | H | CO₂CH₂CH₃ | CH₃ | CF₃ | 2 |
| C(CH₃)₃ | CH₃ | CO₂CH₂CH₃ | H | CF₃ | 2 |
| C(CH₃)₃ | CH₃ | CO₂CH₂CH₃ | F | CF₃ | 2 |
| C(CH₃)₃ | CH₃ | CO₂CH₂CH₃ | Cl | CF₃ | 2 |
| C(CH₃)₃ | CH₃ | CO₂CH₂CH₃ | CH₃ | CF₃ | 2 |

TABLE 30

| R² | R³ | R⁴ | R⁵ | R⁶ | m |
|---|---|---|---|---|---|
| OCH₃ | H | CO₂CH₂CH₃ | H | CF₃ | 2 |
| OCH₃ | H | CO₂CH₂CH₃ | F | CF₃ | 2 |
| OCH₃ | H | CO₂CH₂CH₃ | Cl | CF₃ | 2 |
| OCH₃ | H | CO₂CH₂CH₃ | CH₃ | CF₃ | 2 |
| OCH₃ | CH₃ | CO₂CH₂CH₃ | H | CF₃ | 2 |
| OCH₃ | CH₃ | CO₂CH₂CH₃ | F | CF₃ | 2 |
| OCH₃ | CH₃ | CO₂CH₂CH₃ | Cl | CF₃ | 2 |
| OCH₃ | CH₃ | CO₂CH₂CH₃ | CH₃ | CF₃ | 2 |
| SCH₃ | H | CO₂CH₂CH₃ | H | CF₃ | 2 |
| SCH₃ | H | CO₂CH₂CH₃ | F | CF₃ | 2 |
| SCH₃ | H | CO₂CH₂CH₃ | Cl | CF₃ | 2 |
| SCH₃ | H | CO₂CH₂CH₃ | CH₃ | CF₃ | 2 |
| SCH₃ | CH₃ | CO₂CH₂CH₃ | H | CF₃ | 2 |
| SCH₃ | CH₃ | CO₂CH₂CH₃ | F | CF₃ | 2 |
| SCH₃ | CH₃ | CO₂CH₂CH₃ | Cl | CF₃ | 2 |
| SCH₃ | CH₃ | CO₂CH₂CH₃ | CH₃ | CF₃ | 2 |
| CH₂CH₂CH₃ | H | CO₂CH₂CH₃ | H | CF₃ | 2 |
| CH₂CH₂CH₃ | H | CO₂CH₂CH₃ | F | CF₃ | 2 |
| CH₂CH₂CH₃ | H | CO₂CH₂CH₃ | Cl | CF₃ | 2 |
| CH₂CH₂CH₃ | H | CO₂CH₂CH₃ | CH₃ | CF₃ | 2 |
| CH₂CH₂CH₃ | CH₃ | CO₂CH₂CH₃ | H | CF₃ | 2 |
| CH₂CH₂CH₃ | CH₃ | CO₂CH₂CH₃ | F | CF₃ | 2 |
| CH₂CH₂CH₃ | CH₃ | CO₂CH₂CH₃ | Cl | CF₃ | 2 |
| CH₂CH₂CH₃ | CH₃ | CO₂CH₂CH₃ | CH₃ | CF₃ | 2 |

A compound represented by the formula (I-B):

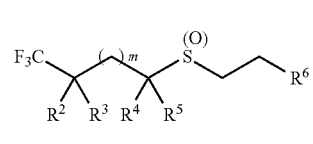

(I-B)

wherein $R^2$, $R^3$, $R^4$, $R^5$, $R^6$ and m represent combinations shown in the above Table 1 to Table 30.

A compound represented by the formula (I-C):

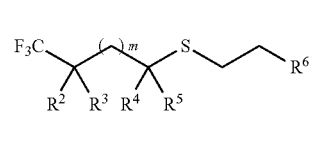

(I-C)

wherein $R^2$, $R^3$, $R^4$, $R^5$, $R^6$ and m represent combinations shown in the above Table 1 to Table 30.

A compound represented by the formula (I-D):

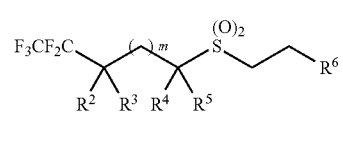

(I-D)

wherein $R^2$, $R^3$, $R^4$, $R^5$, $R^6$ and m represent combinations shown in the following Table 1 to Table 30.

A compound represented by the formula (I-E):

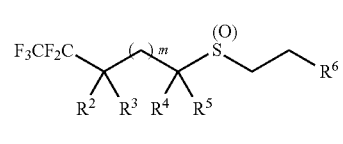

(I-E)

wherein $R^2$, $R^3$, $R^4$, $R^5$, $R^6$ and m represent combinations shown in the above Table 1 to Table 30.

A compound represented by the formula (I-F):

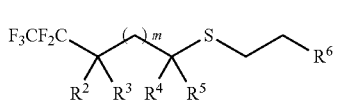

(I-F)

wherein $R^2$, $R^3$, $R^4$, $R^5$, $R^6$ and m represent combinations shown in the above Table 1 to Table 30.

Next, production examples of intermediates for producing the compound of the present invention are shown as Reference Production Examples.

Reference Production Example 1

To a solution of 10 g of methyl thioglycolate and 21 g of 1-iodo-3,3,3-trifluoropropane in 200 ml of N,N-dimethylformamide, 13 g of potassium carbonate was added under ice-cooling, and then stirred at room temperature for 20 hours. To the reaction mixture, 10% hydrochloric acid was added, followed by extraction with ethyl acetate. The organic layer was washed sequentially with 10% hydrochloric acid and a saturated sodium chloride aqueous solution, dried over anhydrous magnesium sulfate, and then concentrated under reduced pressure to obtain a crude product comprising methyl (3,3,3-trifluoropropylthio)acetate. The obtained crude product was dissolved in 100 ml of glacial acetic acid, and 50 ml of peracetic acid (32% (w/w) acetic acid solution) was added thereto under ice-cooling. The mixture was stirred at 60° C. for 16 hours. In the middle of the reaction, the formation of a compound that was presumed to be in a sulfoxide form was confirmed by TLC (thin layer chromathgraphy) analysis. The reaction mixture was allowed to stand to cool to nearly room temperature, poured into water and then extracted with ethyl acetate. The organic layer was washed sequentially with a saturated sodium hydrogen carbonate aqueous solution and a saturated sodium chloride aqueous solution, dried over anhydrous magnesium sulfate, and then concentrated under reduced pressure. The obtained residue was subjected to silica gel chromatography to obtain 14.1 g of methyl (3,3,3-trifluoropropylsulfonyl)acetate.

Methyl (3,3,3-trifluoropropylsulfonyl)acetate

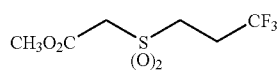

$^1$H-NMR (CDCl$_3$, TMS): δ (ppm) 4.05 (s, 2H), 3.84 (s, 3H), 3.49-3.57 (m, 2H), 2.66-2.79 (m, 2H).

Ethyl (3,3,3-trifluoropropylsulfonyl)acetate can be obtained according to the same procedure except using ethyl thioglycolate in place of methyl thioglycolate.

Reference Production Example 2

To a solution of 9.6 g of 1-bromo-3,3,3-trifluoropropane and 5 g of thiobenzoic acid in 30 ml of N,N-dimethylformamide, 1.45 g of sodium hydride (60% in oil) was added under ice-cooling, and then stirred at room temperature for 12 hours. To the reaction mixture, 10% hydrochloric acid was added, followed by extraction with ethyl acetate. The organic layer was washed sequentially with 10% hydrochloric acid and a saturated sodium chloride aqueous solution, dried over anhydrous magnesium sulfate, and then concentrated under reduced pressure. The obtained residue was subjected to silica gel chromatography to obtain 6.90 g of S-(3,3,3-trifluoropropyl)benzenethioate. S-(3,3,3-trifluoropropyl)benzenethioate:

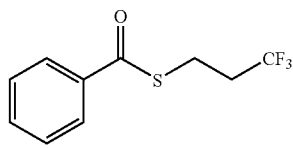

$^1$H-NMR (CDCl$_3$, TMS): δ (ppm) 7.97 (d, 2H), 7.58-7.62 (m, 1H), 7.47 (dd, 2H), 3.24 (t, 2H), 2.44-2.56 (m, 2H).

Reference Production Example 3

To a solution of 10 g of S-(3,3,3-trifluoropropyl)benzenethioate in 50 ml of tetrahydrofuran, 8.4 ml of sodium methoxide (28% (w/w) methanol solution) was added under ice-cooling, and then 5.1 g of bromoacetonitrile was added dropwise at the same temperature. The mixture was stirred at room temperature for 2 hours. To the reaction mixture, 10% hydrochloric acid was added, followed by extraction with ethyl acetate. The organic layer was washed sequentially with 10% hydrochloric acid and a saturated sodium chloride aqueous solution, dried over anhydrous magnesium sulfate, and then concentrated under reduced pressure. The obtained residue was dissolved in 40 ml of glacial acetic acid, and 20 ml of peracetic acid (32% (w/w) acetic acid solution) was added thereto under ice-cooling. The mixture was stirred at 60° C. for 10 hours. The reaction mixture was allowed to stand near room temperature, poured into water, and then extracted with ethyl acetate. The organic layer was washed sequentially with a saturated sodium hydrogen carbonate aqueous solution and a saturated sodium chloride aqueous solution, dried over anhydrous magnesium sulfate, and then concentrated under reduced pressure. The obtained residue was subjected to silica gel chromatography to obtain 7.04 g of (3,3,3-trifluoropropylsulfonyl)acetonitrile.

(3,3,3-Trifluoropropylsulfonyl)acetonitrile

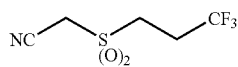

$^1$H-NMR (CDCl$_3$, TMS): δ (ppm) 4.06 (s, 2H), 3.48-3.55 (m, 2H), 2.72-2.84 (m, 2H).

Reference Production Example 4

Step 1

To a solution of ethyl magnesium bromide in diethyl ether prepared from 18.4 g of bromoethane, 4.3 g of magnesium and 150 ml of diethyl ether was added dropwise 20 g of ethyl trifluoroacetate under cooling at −78° C. The mixture was stirred at the same temperature for 1 hour, and then warmed to nearly room temperature. To the reaction mixture was added 10% hydrochloric acid, and then extracted with diethyl ether. The organic layer was dried over anhydrous magnesium sulfate and then filtered to obtain a solution of 1,1,1-trifluoro-2-butanone in diethyl ether.

Step 2

To a suspension of 5.6 g of sodium hydride (60% in oil) in 500 ml of tetrahydrofuran was added dropwise 31.6 g of ethyl diethylphosphonoacetate under ice-cooling. After the mixture was stirred at the same temperature for 10 minutes, the a solution of 1,1,1-trifluoro-2-butanone in diethyl ether obtained in Step 1 was added dropwise thereto. The mixture was stirred at the same temperature for 1 hour, and then warmed to nearly room temperature. To the reaction mixture was added 10% hydrochloric acid, and then extracted with ethyl acetate. The organic layer was dried over anhydrous magnesium sulfate and then concentrated under reduced pressure to obtain crude ethyl 3-trifluoromethyl-2-pentenoate.

Step 3

To a solution of the crude ethyl 3-trifluoromethyl-2-pentenoate obtained in Step 2 in 300 ml of methanol was added 2 g of 10% palladium-carbon at room temperature. Then, hydrogen was passed through the mixture under normal pressure until no hydrogen absorption was observed. After completion of reaction, the inside of the system was substituted with nitrogen, and the reaction mixture was filtered under reduced pressure. The filtrate was concentrated under reduced pressure to obtain a crude mixture of methyl 3-(trifluoromethyl)pentanoate and ethyl 3-(trifluoromethyl)pentanoate.

Step 4

To a suspension of 5.3 g of lithium aluminum hydride in 300 ml of diethyl ether was added dropwise a solution of the crude mixture obtained in Step 3 in 50 ml of diethyl ether under ice-cooling, and then stirred at the same temperature for 2 hours. To the reaction mixture was added 10% hydrochloric acid, and then extracted with diethyl ether. The organic layer was dried over anhydrous magnesium sulfate and then filtered to obtain a solution of 3-(trifluoromethyl)-1-pentanol in diethyl ether.

Step 5

The solution of 3-(trifluoromethyl)-1-pentanol in diethyl ether obtained in Step 4 and 26.8 g of p-toluenesulfonyl chloride were dissolved in 300 ml of tetrahydrofuran. To the solution was added dropwise 20 ml of triethylamine at room temperature, and stirred at the same temperature for 4 days. To the reaction mixture was added 10% hydrochloric acid, and then extracted with ethyl acetate. The organic layer was sequentially washed with 10% hydrochloric acid and a saturated sodium chloride aqueous solution, dried over anhydrous magnesium sulfate, and then concentrated under reduced pressure. The residue was subjected to silica gel chromatography to obtain 18.4 g of 3-trifluoromethyl-pentyl p-toluenesulfonate.

3-Trifluoromethyl-pentyl p-toluenesulfonate

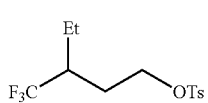

$^1$H-NMR (CDCl$_3$, TMS): δ (ppm) 7.79 (d, 2H), 7.36 (d, 2H), 4.02-4.18 (m, 2H), 2.46 (s, 3H), 1.35-2.18 (m, 5H), 0.94 (t, 3H).

Reference Production Example 5

According to Reference production example 4 except that t-butyl lithium was used instead of ethyl magnesium bromide, 4,4-dimethyl-3-trifluoromethyl-pentyl p-toluenesulfonate was prepared.

4,4-Dimethyl-3-trifluoromethyl-pentyl p-toluenesulfonate

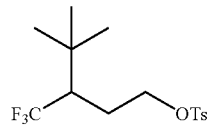

$^1$H-NMR (CDCl$_3$, TMS): δ (ppm) 7.79 (d, 2H), 7.36 (d, 2H), 4.00-4.20 (m, 2H), 2.46 (s, 3H), 1.75-2.00 (m, 3H), 0.99 (s, 9H).

Reference Production Example 6

3-(Trifluoromethyl)pentyl methanesulfonate was obtained according to the Reference Production Example 4 except that methanesulfonyl chloride was used instead of p-toluenesulfonyl chloride.

3-(Trifluoromethyl)pentyl methanesulfonate

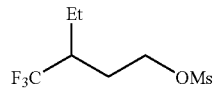

$^1$H-NMR (CDCl$_3$, TMS): δ (ppm) 4.25-4.36 (m, 2H), 3.03 (s, 3H), 1.43-2.28 (m, 5H), 1.02 (dt, 3H).

Reference Production Example 7

4-Methyl-3-(trifluoromethyl)pentyl methanesulfonate was obtained according to the Reference Production Example 4 except that isopropylmagnesium bromide and methanesulfonyl chloride were used instead of ethylmagnesium bromide and p-toluenesulfonyl chloride, respectively.

4-Methyl-3-(trifluoromethyl)pentyl methanesulfonate

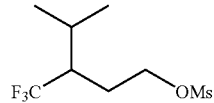

¹H-NMR (CDCl₃, TMS): δ (ppm) 4.19-4.40 (m, 2H), 3.03 (s, 3H), 1.85-2.25 (m, 4H), 1.00 (dd, 6H).

Reference Production Example 8

3-(Trifluoromethyl)hexyl methanesulfonate was obtained according to the Reference Production Example 4 except that propylmagnesium bromide and methanesulfonyl chloride were used instead of ethylmagnesium bromide and p-toluenesulfonyl chloride, respectively.

3-(Trifluoromethyl)hexyl methanesulfonate

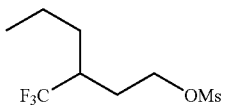

¹H-NMR (CDCl₃, TMS): δ (ppm) 4.24-4.35 (m, 2H), 3.03 (s, 3H), 2.19-2.33 (m, 1H), 1.85-2.10 (m, 2H), 1.30-1.70 (m, 4H), 0.94 (t, 3H).

Reference Production Example 9

(Step 1)

To a solution of 3 g of ethyl 4,4,4-trifluoro-2-butenoate in 30 ml of methanol was added dropwise 5.3 ml of sodium methoxide (28% solution in methanol) at room temperature, and then stirred at the same temperature for 24 hours. To the reaction mixture was added 10% hydrochloric acid and then extracted with diethyl ether. The organic layer was dried over anhydrous magnesium sulfate, and then concentrated under reduced pressure to obtain a crude product comprising methyl 4,4,4-trifluoro-3-methoxybutanoate and ethyl 4,4,4-trifluoro-3-methoxybutanoate.

(Step 2)

To a suspension of 0.7 g of lithium aluminum hydride in 30 ml of diethyl ether, a solution of the crude product obtained in the step 1 in 5 ml of diethyl ether was added dropwise under ice-cooling. The mixture was stirred at the same temperature for 1 hour. To the reaction mixture was added 10% hydrochloric acid and then extracted with diethyl ether. The organic layer was dried over anhydrous magnesium sulfate, and then concentrated under reduced pressure to obtain crude 4,4,4-trifluoro-3-methoxy-1-butanol.

(Step 3)

The crude product obtained in the step 2 and 3.4 g of p-toluenesulfonyl chloride were dissolved in 30 ml of tetrahydrofuran. To the solution was added dropwise 2.5 ml of triethylamine at room temperature. The mixture was stirred at the same temperature for 5 days. To the reaction mixture was added 10% hydrochloric acid and then extracted with ethyl acetate. The organic layer was washed sequentially with 10% hydrochloric acid and a saturated sodium chloride aqueous solution, dried over anhydrous magnesium sulfate, and then concentrated under reduced pressure. The residue was subjected to silica gel column chromatography to obtain 4.20 g of 4,4,4-trifluoro-3-(methoxy)butyl p-toluenesulfonate.

4,4,4-Trifluoro-3-(methoxy)butyl p-toluenesulfonate

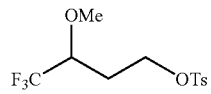

¹H-NMR (CDCl₃, TMS): δ (ppm) 7.81 (dd, 2H), 7.37 (dd, 2H), 4.05-4.28 (m, 2H), 3.58-3.72 (m, 1H), 3.47 (s, 3H), 2.46 (s, 3H), 1.73-2.10 (m, 2H).

Reference Production Example 10

(Step 1)

To a solution of 3 g of ethyl 4,4,4-trifluoro-2-butenoate in 30 ml of methanol was added 8.3 g of sodium thiomethoxide (15% aqueous solution) at room temperature, and then stirred at the same temperature for 2 days. To the reaction mixture was added 10% hydrochloric acid and then extracted with ethyl acetate. The organic layer was dried over anhydrous magnesium sulfate, and then concentrated under reduced pressure to obtain a crude product comprising methyl 4,4,4-trifluoro-3-methylthiobutanoate, ethyl 4,4,4-trifluoro-3-methylthiobutanoate and 4,4,4-trifluoro-3-methylthiobutanoic acid.

(Step 2)

To a suspension of 0.7 g of lithium aluminum hydride in 30 ml of diethyl ether, a solution of the crude product obtained in the step 1 in 5 ml of diethyl ether was added dropwise under ice-cooling. The mixture was stirred at the same temperature for 2 hours. To the reaction mixture was added 10% hydrochloric acid and then extracted with diethyl ether. The organic layer was dried over anhydrous magnesium sulfate, and then concentrated under reduced pressure to obtain crude 4,4,4-trifluoro-3-methylthio-1-butanol.

(Step 3)

The crude product obtained in the step 2 and 3.3 g of p-toluenesulfonyl chloride were dissolved in 30 ml of tetrahydrofuran. To the solution was added dropwise 2.4 ml of triethylamine at room temperature. The mixture was stirred at the same temperature for 3 days. To the reaction mixture was added 10% hydrochloric acid and then extracted with ethyl acetate. The organic layer was washed sequentially with 10% hydrochloric acid and a saturated sodium chloride aqueous solution, dried over anhydrous magnesium sulfate, and then concentrated under reduced pressure. The residue was subjected to silica gel column chromatography to obtain 4.10 g of 4,4,4-trifluoro-3-(methylthio)butyl p-toluenesulfonate.

4,4,4-Trifluoro-3-(methylthio)butyl p-toluenesulfonate

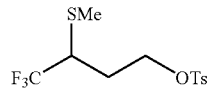

¹H-NMR (CDCl₃, TMS): δ (ppm) 7.81 (dd, 2H), 7.37 (dd, 2H), 4.15-4.42 (m, 2H), 3.00-3.14 (m, 1H), 2.46 (s, 3H), 2.19-2.31 (m, 1H), 2.15 (s, 3H), 1.65-1.75 (m, 1H).

Reference Production Example 11

4,4,4-Trifluoro-3-(methylthio)butyl methanesulfonate was obtained according to the Reference Production Example 10 except that methanesulfonyl chloride was used instead of p-toluenesulfonyl chloride.

4,4,4-Trifluoro-3-(methylthio)butyl methanesulfonate

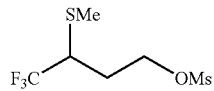

¹H-NMR (CDCl₃, TMS): δ (ppm) 4.35-4.61 (m, 2H), 3.11-3.24 (m, 1H), 3.06 (s, 3H), 2.31-2.45 (m, 1H), 2.25 (s, 3H), 1.78-1.90 (m, 1H).

Reference Production Example 12

4,4,5,5,5-Pentafluoro-3-methylpentyl methanesulfonate was obtained according to the Reference Production Example 4 except that methyl pentafluoropropionate, methylmagnesium bromide and methanesulfonyl chloride were used instead of ethyl trifluoroacetate, ethylmagnesium bromide and p-toluenesulfonyl chloride, respectively.

4,4,5,5,5-Pentafluoro-3-methylpentyl methanesulfonate

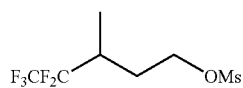

¹H-NMR (CDCl₃, TMS): δ (ppm) 4.26-4.40 (m, 2H), 3.04 (s, 3H), 2.18-2.55 (m, 2H), 1.68-1.79 (m, 1H), 1.19 (d, 3H).

Next, Formulation Examples are shown. The term "part(s)" means part(s) by weight.

Formulation Example 1

Nine parts of any one of the present compounds (1) to (31) is dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 2

Five parts of the present compound (1) and 4 parts of a compound selected from the following group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

The group [A]:

aluminum phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, cadusafos;

alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb, aldicarb;

acrinathrin, allethrin, benfluthrin, beta-cyfluthrin, bifenthrin, cycloprothrin, cyfluthrin, cyhalothrin, empenthrin, deltamethrin, esfenvalerate, ethofenprox, fenvalerate, flucythrinate, flufenoprox, flumethrin, fluvalinate, halfenprox, imiprothrin, prallethrin, pyrethrins, resmethrin, sigma-cypermethrin, silafluofen, tefluthrin, tralomethrin, transfluthrin, tetramethrin, lambda-cyhalothrin, gamma-cyhalothrin, furamethrin, tau-fluvalinate, 2,3,5,6-tetrafluoro-4-methylbenzyl 2,2-dimethyl-3-(1-propenyl)cyclopropanecarboxylate, 2,3,5,6-tetrafluoro-4-(methoxymethyl)benzyl 2,2-dimethyl-3-(2-methyl-1-propenyl)cyclopropanecarboxylate, 2,3,5,6-tetrafluoro-4-(methoxymethyl)benzyl 2,2-dimethyl-3-(2-cyano-1-propenyl)cyclopropanecarboxylate, 2,3,5,6-tetrafluoro-4-(methoxymethyl)benzyl 2,2,3,3-tetramethylcyclopropanecarboxylate;

cartap, bensultap, thiocyclam, monosultap, bisultap; imidacloprid, nitenpyram, acetamiprid, thiamethoxam, thiacloprid;

chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, triazuron;

acetoprole, fipronil, vaniliprole, pyriprole, pyrafluprole, and the like;

chromafenozide, halofenozide, methoxyfenozide, tebufenozide;

aldrin, dieldrin, dienochlor, endosulfan, methoxychlor; nicotine sulfate;

avermectin-B, bromopropylate, buprofezin, chlrphenapyr, cyromazine, D-D (1,3-dichloropropene), emamectin-benzoate, fenazaquin, flupyrazofos, hydroprene, methoprene, indoxacarb, metoxadiazone, milbemycin-A, pymetrozine, pyridalyl, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, potassium oleate, protrifenbute, spiromesifen, sulfur, metaflumizone, spirotetramat, pyrifluquinazone, chlorantraniliprole, tralopyril, a compound represented by the following formula (A):

(A)

wherein $X^{a1}$ represents methyl, chlorine, bromine or fluorine, $X^{a2}$ represents fluorine; chlorine, bromine, C1-C4 haloalkyl or C1-C4 haloalkoxy, $X^{a3}$ represents fluorine, chlorine or bromine, $X^{a4}$ represents optionally substituted C1-C4 alkyl, optionally substituted C3-C4 alkenyl, optionally substituted C3-C4 alkynyl, optionally substituted C3-C5 cycloalkyl or hydrogen, $X^{a5}$ represents hydrogen or methyl, $X^{a6}$ represents hydrogen, fluorine or chlorine, and $X^{a7}$ represents hydrogen, fluorine or chlorine;
a compound represented by the following formula (B):

(B)

wherein $X^{b1}$ represents $X^{b2}$—NH—C(=O), $X^{b2}$—C(=O)—NH, $X^{b3}$—S(O), optionally substituted pyrrol-1-yl, optionally substituted imidazol-1-yl, optionally substituted pyrazol-1-yl, or optionally substituted 1,2,4-triazol-1-yl, $X^{b2}$ represents optionally substituted C1-C4 haloalkyl such as 2,2,2-trifluoroethyl or optionally substituted C3-C6 cycloalkyl such as cyclopropyl, and $X^{b3}$ represents optionally substituted C1-C4 alkyl such as methyl;
a compound represented by the following formula (C):

(C)

wherein $X^{c1}$ represents optionally substituted C1-C4 alkyl such as 3,3,3-trifluoropropyl, optionally substituted C1-C4 alkoxy such as 2,2,2-trichloroethoxy or optionally substituted phenyl such as phenyl, $X^{c2}$ represents methyl or trifluoromethylthio, and $X^{c3}$ represents methyl or halogen; acequinocyl, amitraz, benzoximate, bifenaate, bromopropylate, chinomethionat, chlorobenzilate, CPCBS (chlorfenson), clofentezine, cyflumetofen, kelthane (dicofol), fenbutatin oxide, fenothiocarb, fenpyroximate, fluacrypyrim, fluproxyfen, hexythiazox, propargite (BPPS), pyridaben, pyrimidifen, tebufenpyrad, tetradifon, spirodiclofen, spiromesifen, spirotetramat, amidoflumet, and cyenopyrafen.

Formulation Example 3

Five parts of the present compound (2) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 4

Five parts of the present compound (3) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 5

Five parts of the present compound (4) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 6

Five parts of the present compound (5) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 7

Five parts of the present compound (6) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 8

Five parts of the present compound (7) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 9

Five parts of the present compound (8) and 4 parts of a compound selected from the group [A] are dissolved in 37.5 parts of xylene and 37.5 parts of N,N-dimethylformamide. Thereto 10 parts of polyoxyethylene styryl phenyl ether and 6

Formulation Example 10

Five parts of the present compound (9) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 11

Five parts of the present compound (10) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 12

Five parts of the present compound (11) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 13

Five parts of the present compound (12) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 14

Five parts of the present compound (13) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 15

Five parts of the present compound (14) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 16

Five parts of the present compound (15) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 17

Five parts of the present compound (16) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 18

Five parts of the present compound (17) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 19

Five parts of the present compound (18) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 20

Five parts of the present compound (19) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 21

Five parts of the present compound (20) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 22

Five parts of the present compound (21) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 23

Five parts of the present compound (22) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 24

Five parts of the present compound (23) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 25

Five parts of the present compound (24) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 26

Five parts of the present compound (25) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 27

Five parts of the present compound (26) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 28

Five parts of the present compound (27) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 29

Five parts of the present compound (28) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 30

Five parts of the present compound (29) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 31

Five parts of the present compound (30) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 32

Five parts of the present compound (31) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 33

Five parts of SORPOL 5060 (registered trade name for TOHO Chemical Industry Co., LTD.) is added to 40 parts of any one of the present compounds (1) to (31) and mixed thoroughly. Then, 32 parts of CARPLEX #80 (registered trade name for Shionogi & Co., Ltd., synthetic anhydrous silicon oxide fine powder) and 23 parts of 300 mesh diatomaceous earth are added thereto and mixed with a juice mixer to obtain a wettable powder.

Formulation Example 34

Three parts of any one of the present compounds (1) to (31), 5 parts of synthetic hydrous silicon oxide fine powder, 5 parts of sodium dodecylbenzenesulfonate, 30 parts of bentonite and 57 parts of clay are mixed by stirring thoroughly. To this mixture an appropriate amount of water is added. The mixture is further stirred, granulated with a granulator, and then air-dried to obtain a granule.

Formulation Example 35

Four point five parts of any one of the present compounds (1) to (31), 1 part of synthetic hydrous silicon oxide fine powder, 1 part of Dorires B (manufactured by Sankyo) as a flocculant, and 7 parts of clay are mixed thoroughly with a mortar and then by stirring with a juice mixer. To the resultant mixture 86.5 parts of cut clay is added and mixed by stirring thoroughly to obtain a powder.

Formulation Example 36

Ten parts of any one of the present compounds (1) to (31), 35 parts of white carbon containing 50 parts of polyoxyethylene alkylether sulfate ammonium salt, and 55 parts of water are mixed and then finely-divided by a wet grinding method to obtain a preparation.

Formulation Example 37

Zero point five part of any one of the present compounds (1) to (31) is dissolved in 10 parts of dichloromethane. This solution is mixed with 89.5 parts of Isopar M (isoparaffin: registered trade name for Exxon Chemical) to obtain an oil.

Formulation Example 38

Zero point one part of any one of the present compounds (1) to (31) and 49.9 parts of NEO-THIOZOL (Chuo Kasei Co., Ltd.) are placed in an aerosol can. An aerosol valve is fitted to the can and the can is then charged with 25 parts of dimethyl ether and 25 parts of LPG. An actuator is fitted to the can to obtain an oily aerosol.

Formulation Example 39

An aerosol container is charged with 0.6 parts of any one of the present compounds (1) to (31), 0.01 part of BHT, 5 parts of xylene, a mixture of 3.39 parts of a deodorized kerosine and 1 part of an emulsifying agent [Atmos 300 (registered trade name for Atmos Chemical Ltd.)] and 50 parts of distilled water. A valve part is attached to the container and the container is then charged with 40 parts of a propellant (LPG) through the valve under increased pressure to obtain an aqueous aerosol.

Formulation Example 40

Five parts of any one of the present compounds (1) to (31) is dissolved in 80 parts of diethylene glycol monoethyl ether. Thereto 15 parts of propylene carbonate is mixed to obtain a spot-on liquid formulation.

Formulation Example 41

Ten parts of any one of the present compounds (1) to (31) is dissolved in 70 parts of diethylene glycol monoethyl ether. Thereto 20 parts of 2-octyldodecanol is mixed to obtain a pour-on liquid formulation.

Formulation Example 42

To 0.5 parts of any one of the present compounds (1) to (31) are added 60 parts of NIKKOL TEALS-42 (a 42% aqueous solution of triethanolamine lauryl sulfate, Nikko Chemicals) and 20 parts of propylene glycol. The mixture is stirred well to obtain a homogeneous solution. Thereto 19.5 parts of water is added and mixed by stirring thoroughly to obtain a homogeneous shampoo formulation.

Formulation Example 43

A porous ceramic plate with a length of 4.0 cm, a width of 0.4 cm and a thickness of 1.2 cm is impregnated with a solution of 0.1 g of any one of the present compounds (1) to (31) in 2 ml of propylene glycol to obtain a heating-type smoking agent.

Formulation Example 44

Five parts of any one of the present compounds (1) to (31) and 95 parts of an ethylene-methyl methacrylate copolymer (the proportion of methyl methacrylate in the copolymer: 10% by weight, ACRYFT WD301, Sumitomo Chemical) are melted and kneaded in a sealed pressure kneader (Moriyama Manufacturing Co., Ltd.). The obtained kneaded product is extruded through a molding die using an extruder to obtain a molded bar with a length of 15 cm and a diameter of 3 mm.

Formulation Example 45

Five parts of any one of the present compounds (1) to (31) and 95 parts of a flexible polyvinyl chloride resin are melted and kneaded in a sealed pressure kneader (Moriyama Manufacturing Co., Ltd.). The obtained kneaded product is extruded through a molding die using an extruder to obtain a molded bar with a length of 15 cm and a diameter of 3 mm.

Next, effectiveness of the compound of the present invention as the active ingredient of a pesticidal composition will be shown by Test Examples.

Test Example 1

Preparations of the present compounds (2), (3), (5), (6), (8), (9), (10), (11), (12), (14), (15), (16), (17), (19), (20), (23), (24), (25), (26), (28), (29) and (31) obtained according to Formulation Example 36 were diluted so that the active ingredient concentration was 55.6 ppm to obtain test solutions.

At the same time, 50 g of culture soil, Bonsol No. 2 (manufactured by Sumitomo Chemical Co., Ltd.) was put into a polyethylene cup with five holes of 5 mm diameter at the bottom, and 10 to 15 seeds of rice were planted therein. The rice plants were grown until the second foliage leaf was developed, and then treated with 45 ml of the test solution by allowing the plants to absorb the test solution from the bottom of the cup. The rice plants were placed in a greenhouse at 25° C. for 6 days and then cut into the same height of 5 cm. Thirty first-instar larvae of *Nilaparvata lugens* were released into the greenhouse at 25° C. and left for 6 days. Then, the number of parasitic *Nilaparvata lugens* on the rice plants was examined.

As a result, on the plants treated with the present compounds (2), (3), (5), (6), (8), (9), (10), (11), (12), (14), (15), (16), (17), (19), (20), (23), (24), (25), (26), (28), (29) and (31), the number of the parasitic pests was 3 or smaller.

Test Example 2

Preparations of the present compounds (2), (3), (5), (6), (9), (10), (11), (12), (13), (14), (15), (16), (17), (19), (20), (24), (25), (26), (28), (29), (30) and (31) obtained according to Formulation Example 36 were diluted so that the active ingredient concentration was 500 ppm to obtain test solutions.

A filter paper having a diameter of 5.5 cm was spread on the bottom of a polyethylene cup having a diameter of 5.5 cm and 0.7 ml of the test solution was added dropwise onto the filter paper. As a bait 30 mg of sucrose was uniformly placed on the filter paper. Into the polyethylene cup, 10 female imagoes of *Musca domestica* were released and the cup was sealed with a lid. After 24 hours, the number of surviving *Musca domestica* was examined and the death rate of the pest was calculated.

As a result, in treatments with the present compounds (2), (3), (5), (6), (9), (10), (11), (12), (13), (14), (15), (16), (17), (19), (20), (24), (25), (26), (28), (29), (30) and (31), the death rate of the pest was 70% or more.

Test Example 3

Preparations of the present compounds (2), (3), (5), (6), (10), (11), (12), (14), (15), (16), (17), (19), (20), (24), (25), (26), (29), (30) and (31) obtained according to Formulation Example 36 were diluted so that the active ingredient concentration was 500 ppm to obtain test solutions.

A filter paper having a diameter of 5.5 cm was spread on the bottom of a polyethylene cup having a diameter of 5.5 cm and 0.7 ml of the test solution was added dropwise onto the filter paper. As a bait 30 mg of sucrose was uniformly placed on the filter paper. Into the polyethylene cup, 2 male imagoes of *Blattalla germanica* were released and the cup was sealed with a lid. After 6 days, the number of surviving *Blattalla germanica* was examined and the death rate of the pest was calculated.

As a result, in treatments with the present compounds (2), (3), (5), (6), (10), (11), (12), (14), (15), (16), (17), (19), (20), (24), (25), (26), (29), (30) and (31), the death rate of the pest was 100%.

Test Example 4

Preparations of the present compounds (1), (2), (3), (4), (5), (6), (9), (10), (11), (12), (14), (15), (16), (17), (19), (20), (22), (23), (24), (26), (27), (28), (29), (30) and (31) obtained according to Formulation Example 36 were diluted so that the active ingredient concentration was 500 ppm to obtain test solutions.

To 100 mL of ion-exchanged water, 0.7 ml of the test solution was added (active ingredient concentration: 3.5 ppm). Into the solution, 20 last-instar larvae of *Culex pipiens pallens* were released. After one day, the number of surviving *Culex pipiens pallens* was examined and the death rate of the pest was calculated.

As a result, in treatments with the present compounds (1), (2), (3), (4), (5), (6), (9), (10), (11), (12), (14), (15), (16), (17), (19), (20), (22), (23), (24), (26), (27), (28), (29), (30) and (31), the death rate of the pest was 90% or more.

Test Example 5

Five milligrams of any one of the present compounds (3), (10), (14), (15), (16) and (17) was dissolved in 10 mL of acetone. One milliliter of the acetone solution was uniformly applied on one side of a filter paper (TOYO No. 2; 5×10 cm), so that the filter paper was treated with 100 mg/m² of the present compound. After drying, the filter paper was folded in two and its edges were clipped to make a pouch. Non-blood-sucking nymphal ticks (*Haemaphysalis longicornis*, 10 ticks/group) were put into the pouch, and the pouch was sealed with clips. After 2 days, the number of surviving ticks was examined and the death rate was calculated.

As a result, in treatments with the present compounds (3), (10), (14), (15), (16) and (17), the death rate of the tick was 90%.

Industrial Applicability

The compound of the present invention has an excellent controlling effect on harmful arthropods, and thus, it is useful as an active ingredient for a pesticidal composition.

The invention claimed is:

1. An organic sulfur compound represented by the formula (I):

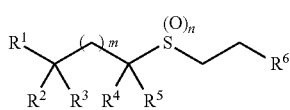

(I)

wherein,
$R^1$ represents a C1-C5 haloalkyl group having at least one fluorine atom,
$R^2$ represents a C1-C4 alkyl group optionally substituted with at least one halogen atom, a C1-C4 alkoxy group optionally substituted with at least one halogen atom, or a C1-C4 alkylthio group optionally substituted with at least one halogen atom,
$R^3$ represents a hydrogen atom, a halogen atom or a C1-C4 alkyl group,
$R^4$ represents a cyano group, $C(=Q)OR^7$ or $C(=Q)N(R^8)_2$,
$R^5$ represents a hydrogen atom, a halogen atom or a C1-C4 alkyl group,
$R^6$ represents a C1-C5 fluoroalkyl group,
Q represents an oxygen atom or a sulfur atom,
$R^7$ represents a C1-C4 alkyl group,
$R^8$'s each independently represent a hydrogen atom or a C1-C4 alkyl group, or two $R^8$'s are bonded to each other at their terminals to form a C2-C7 alkylene group,
m represents an integer of 1 to 4, and
n represents 0, 1 or 2.

2. The organic sulfur compound according to claim 1, wherein n is 2.

3. The organic sulfur compound according to claim 1 or 2, wherein Q is an oxygen atom.

4. The organic sulfur compound according to claim 1 or 2, wherein $R^4$ is a cyano group.

5. The organic sulfur compound according to claim 1 or 2, wherein $R^4$ is $C(=Q)N(R^8)_2$, and $R^8$'s are each independently a hydrogen atom or a C1-C4 alkyl group.

6. The organic sulfur compound according to claim 1 or 2, wherein $R^4$ is $C(=Q)N(R^8)_2$ and $R^8$ is a hydrogen atom.

7. The organic sulfur compound according to claim 1, wherein $R^5$ is a halogen atom.

8. The organic sulfur compound according to claim 1, wherein m is 2.

9. A pesticidal composition comprising the organic sulfur compound according to claim 1 as an active ingredient.

10. A method for controlling harmful arthropods comprising applying an effective amount of the organic sulfur compound according to claim 1 to harmful arthropods or a place where harmful arthropods inhabit.

* * * * *